US012458088B2

(12) United States Patent
Ramirez

(10) Patent No.: US 12,458,088 B2
(45) **Date of Patent: *Nov. 4, 2025**

(54) FINGER COTS AND SPORTS SLEEVES

(71) Applicant: John Ramirez, Redlands, CA (US)

(72) Inventor: John C. Ramirez, Redlands, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/144,192

(22) Filed: May 6, 2023

(65) Prior Publication Data

US 2024/0023653 A1 Jan. 25, 2024

Related U.S. Application Data

(60) Continuation-in-part of application No. 17/347,604, filed on Jun. 15, 2021, now abandoned, which is a division of application No. 16/236,294, filed on Dec. 28, 2018, now Pat. No. 11,064,748, which is a division of application No. 14/121,908, filed on Oct. 31, 2014, now Pat. No. 10,219,555, which is a continuation-in-part of application No. 13/374,538, filed on Jan. 3, 2012.

(51) Int. Cl.

| | |
|---|---|
| ***A41D 13/08*** | (2006.01) |
| ***A41D 13/00*** | (2006.01) |
| ***A41D 31/12*** | (2019.01) |
| ***A41D 31/18*** | (2019.01) |
| ***A61F 13/10*** | (2006.01) |
| *A41D 27/12* | (2006.01) |

(52) U.S. Cl.

CPC ......... *A41D 31/18* (2019.02); *A41D 13/0015* (2013.01); *A41D 13/08* (2013.01); *A41D 13/087* (2013.01); *A41D 31/12* (2019.02); *A61F 13/105* (2013.01); *A41D 27/12* (2013.01); *A41D 2400/80* (2013.01); *A41D 2600/10* (2013.01)

(58) Field of Classification Search

CPC .................................................... A41D 13/087
USPC .................................................. 2/16, 20, 21
See application file for complete search history.

(56) References Cited

U.S. PATENT DOCUMENTS

| | | | | |
|---|---|---|---|---|
| 9,022,873 | B2 * | 5/2015 | Ramirez | A63B 71/141 2/161.1 |
| 10,219,555 | B2 * | 3/2019 | Ramirez | A61F 13/105 |
| 11,064,748 | B2 * | 7/2021 | Ramirez | A41D 31/12 |
| 2006/0230487 | A1 * | 10/2006 | Salomon | D05B 91/04 2/21 |
| 2010/0011484 | A1 * | 1/2010 | Williams | A41D 19/01564 2/163 |
| 2013/0111642 | A1 * | 5/2013 | Eugene | A41D 13/087 2/21 |

* cited by examiner

*Primary Examiner* — Katherine M Moran

(57) ABSTRACT

According to the various features, characteristics and embodiments of the present invention which will become apparent as the description thereof proceeds, the present invention provides reusable grip enhancing tubular members for the arm area, in particular sports sleeves for the arm and forearm, and reusable grip enhancing tubular members for the hand, in particular sports finger cots for the hand, and the uses thereof, and methods thereof, intended to increase the performance in arm and/or hand task activities.

20 Claims, 26 Drawing Sheets

FINGER COTS AND SPORTS SLEEVES

This is a Continuation-in-part to application Ser. No. 17/347,604, now abandoned, which is a Divisional to application Ser. No. 16/236,294, which is a Divisional to application Ser. No. 14/121,908, now U.S. Pat. No. 10,219,255 which is a Continuation-In-Part to application Ser. No. 13/374,538, now abandoned, in its entirety.

BACKGROUND OF THE INVENTION

An important goal in playing sports is to win. Often that means proper play execution, proper form in the sports fundamentals and especially good ball control. Many of these tasks are performed by the hand, but are often also performed, to some degree, with parts of the arm (the wrists, forearm, elbow and bicep areas). Ball control and therefore proper play execution depend on adequately using the parts of the forearm, elbow and/or bicep areas to handle, strike, control or otherwise maintain possession. Inadequate play execution can result in inconsistencies and turnovers, both long standing problems in many sports, and can often determine the outcome of a game.

The Need for Grip Enhancers for the Arm Area

In the sport of football, for example, lack of play execution is often categorized by turnovers, fumbles and incomplete passes. This is of particular concern to those players that have to control the football such as running backs, receivers, tight ends, kick returners, punt returners and even quarterbacks. Athletes that play any of these positions are often asked, in some way, to run, catch, throw or otherwise control a football. A team's ability to successfully minimize fumbles, incompletes and inconsistencies, can often be the determining factor in the outcome of a game. Creating and maintaining a solid and stable overall control of the ball is therefore an essential component in proper play execution and performance. Often this means being able to grip as well as 'feel' a ball or object.

In the sport of football, as in many other sports, controlling a ball is often done not just by using their hands, but by using other parts of the body as well.

A football running back, for instance, might be particularly concerned with not fumbling the ball. A running back's performance is measured not only by his yards per carry but also in his ability to minimize his fumbles. Unfortunately, one need only view the statistics to see that fumbles persist as an insoluble problem, even at the professional level today.

Part of the problem lie in the seemingly inherently unstable and uneven way a player controls and cradles a ball when running. Proper ball handling technique is to grab one end of the football with your hand, and then resting the ball on the forearm of the same arm. As you begin to run with the ball, you may also place the opposite end of the ball (the end that is not being held by the hand) in the inside elbow area, between the forearm and bicep, and the ball is almost always touching the wrist area. Although prior art exists to increase grip around the hand, no art currently exists that will increase ones grip in the forearm area or the wrist.

Football players who catch a football (hereinafter called 'receivers') might be particularly concerned with making a catch and completing a reception, and being able to control a ball with the arm area. Enough skill and precision must take place in order to get the ball from the quarterback to a receiver; timing, stable footing, and protecting the ball just to name a few. When a receiver first catches a ball, he usually brings the ball into the arm, thus holding the ball with the hand, as well as the wrist and forearm area. Providing art that enhances the grip around the wrist or forearm area would certainly enhance the receiver's ability to complete the pass reception successfully, often an important aspect in determining who wins the game, since passing the football is a significant part of the sport of football, sometimes throwing as much as 103 times in a game (Seattle vs. San Diego, 2002). Thus, developing a solution to enhance one's ability of better controlling a catch and completing a pass reception would substantially impact the sport. Additionally, inconsistencies or incompletes often arise when a 'stress factor' is introduced once a receiver first touches and places the ball on their arm area. This problem is so pronounced that many instant replay situations revolve around seeing whether the ball moves even slightly in the receivers arm—including the forearm. As such, an unrecognized problem currently exists because it is very difficult to grip a ball with parts of the arm.

Clearly, maintaining good ball control is important. In football, unstable or weak ball control can, among other things, increase fumbles, increase incompletes and thereby increase turnovers and decrease performance.

There have been some attempts through the years to solve the problems of inconsistencies and turnovers in the sport of football. For example, changes have been made to the actual football in order to make the ball easier to handle. Changes to the shape and size, as well as the addition of grip enhancing materials to the ball—such as the addition of PVC (Poly Vinyl Chloride) dots—have made it possible to make the ball more grippable. The ability of the player to maintain control of the football was still problematic because of the lack of any grip enhancing device for the player to use; devices that could be placed on the arm such that the player could now more significantly control a ball with his arm, thereby creating a better overall grip of the football throughout the football. As a result of this unmet need, inconsistencies and turnovers were still high in the sport.

The introduction and subsequent proliferation in the use of football gloves found some success but even with these advancements, however, fumbles and incompletes still persist today. For one, whereas a running back who uses a grip enhancing glove will be better able to properly grip a football by using his hands, his hand, and therefore the grip enhancing device, only cover the front part of the ball, leaving the rest of the ball, and therefore the overall grip, still significantly unstable. One need only add a stress factor and this currently unstable hold on the ball can easily result in a fumble.

Good ball control is so important in football that inventions were created and widely used to enhance the gripping abilities of an individual's hand. Improvements have lacked in the areas of helping the rest of the arm better grip a ball.

No improvements have been developed that could provide enhanced gripping support around the wrist area, an area that almost always touches the ball when cradling the ball. Improvements have lacked in offering a player the ability to achieve an enhanced grip capability around the forearm area, thus providing a higher static coefficient of friction than that of the skin of the user, an area that plays a major role in maintaining control of a ball when a receiver is completing a reception. Advances have lacked in increasing one's grip around the wrist area, or in increasing ball control around the elbow or bicep areas.

Providing such a device would certainly allow a player to have a much stronger grip throughout and around the ball, to create a more stable overall handle on the ball, and therefore to significantly advance arm task performance and play execution. Not only would new art offer benefits to running backs, receivers, tight ends and quarterbacks, but they could also increase the performances of kick returners and punt returners, who have to run with the football.

In addition, no art currently exists that offers a grip enhancing device as a covering for one's sports arm pads. For example, if a running back has a forearm pad for protection but also wants to add a grip enhancer to it, he currently cannot purchase a grip enhancer cover that he could temporarily place over his existing arm pad. Grip enhancing covers would be well received in this sport and would offer significant and substantial benefits.

Because no such art exists, it is no surprise that there were a total of 731 fumbles, and the highest quarterback completion rating was less than 70 percent, in the 2010 NFL Season (Official Stat Book of the NFL, 2011). Given the fact that fumbles persist at the professional level and therefore certainly at the collegiate and amateur levels, one can see that past attempts to solve these problems have had limited success.

An example of another sport in need of grip enhancers for the forearm and wrist area is Volleyball. Here too, ball control is crucial to play performance. Play execution often depends on one's ability to control a ball with multiple parts of your arm, but especially your forearm. Although there are forearm, elbow and even bicep devices that could be used for protection, or simply for aesthetic purposes, no prior art exists that would enhance ball control in said areas for volleyball.

When an opponent strikes a volleyball to the other team's side of the net, the first player to normally touch the ball—when the ball isn't blocked at the net—generally controls the ball with her or his forearms. With that first touch contact, one must be able to stabilize the ball, and then usually pass the ball to a teammate.

Unfortunately, this current method of passing a volleyball can provide inconsistent results. First, the initial contact control is generally with the forearm skin of the player, and without any grip enhancing device, it can become very difficult to redirect a volleyball with consistent precision either because of the generally low grip capabilities that the human skin provides or because the player's forearm has perspiration or moisture. Although the initial contact happens very fast, a control enhancing mechanism for the arm area would have a significant impact on the sport. Additionally, a more general reason for inconsistencies is in one's inability to grip with one's forearm due to its generally low coefficient of friction. Without providing the forearm with some way to better grip a volleyball, inconsistencies in the sport of volleyball will continue to be a long-standing problem.

Additionally, any type of grip enhancers for the wrist area would provide similar benefits as mentioned above.

The Need for Sport Grip Enhancers for the Fingers

Not only are there significant needs for grip enhancing devices and grip enhancing covers for the arm area—in particular the wrist, forearm elbow and bicep areas—but there is also a significant need for better grip enhancing devices for the hands as well. Although offering some advantages, using prior art creates disadvantages that often forces an individual to choose not to use any grip enhancing device at all.

One particular area where prior art poses significant disadvantages is in any sport where a player's success depends on her ability to both grip as well as feel a ball or object. These players often have to choose between wearing a glove thereby enhancing grip but losing significant feel, or going without a glove thereby maintaining maximum feel but missing the opportunity to enhance one's grip.

In football for example, gloves can be used to enhance performance. The use of gloves in football is so widespread that nearly every football player uses them, with the notable exception of football quarterbacks. You rarely see a quarterback wear gloves, even if just to keep warm. Most quarterbacks choose to play football without gloves. This is largely because prior art consists of generic full-fingered gloves which are uncomfortable and burdensome on a quarterback's dominant (throwing) hand, particularly on those fingers a quarterback places over the football laces. In addition, the full-fingered gloves prevent a quarterback to have much 'feel' of the ball.

Playing the position of quarterback without the help of gloves, however, can also be an inferior choice. The website Wikihow.com, provides a good description of the conventional way to hold and throw a football. "Throwing the football is simple. Put your non-throwing side foot in front of you. Have your Pinkie, Ring and Middle fingers around the laces with your Index [Forefinger] finger on the strap. Put the other hand up on the ball. Put the ball up by your ear. Twist your hips toward the front foot. Throw the ball at the receiver." Whereas, the fingers over the laces have a solid grip on the ball—primarily due to the football laces on the ball—the two fingers off the laces (forefinger and thumb) are virtually unsupported and therefore have a relatively weaker grip, creating a weak overall grip on the football.

This weak overall grip becomes more pronounced when added stress is placed on the thumb or forefinger. When a quarterback, intending to pass the football, for example, suddenly has to scramble, or if the quarterback 'pumps' the ball (goes through all the motions and speed of throwing the ball but doesn't actually release the ball), the grip strength of the thumb and forefinger can determine whether or not a quarterback fumbles the ball. Also, if one performs a simple test and wets his/her dominant hand, and then grabs and pumps a football, the forefinger and thumb will often move or slip. On a wet football field, during extreme weather conditions (hot or cold), that weaker or looser grip makes for a much more difficult completed pass, less success at throwing a spiral, and inconsistency and inaccuracy in passing.

Under the 'tips' section of Wikihow.com, it further describes proper football throwing form: "A proper throw will feel like it's only utilizing the Thumb, Index [Forefinger], and Middle finger. Good release will 'roll' off of your Index and Middle finger, to impart more spin; you may snap your wrist through as you follow through to the hip. The other three fingers on your hand stabilize the ball as its being flung. They should not be used to impart spin on the ball. The most important finger to throwing a spiral is the Index finger; it is the finger that holds the most leverage in putting spin on the ball."

This need to 'feel' a ball with a hand has therefore resulted in quarterbacks having a difficult choice. Although clearly these players would benefit from added grip enhancements on the throwing hand, prior art (in the form of gloves) force a quarterback to choose between all feel and no feel. Virtually all quarterbacks have chosen to maintain feel and sacrifice the ability to better grip the football, and therefore not wear gloves. It is no surprise that quarterback fumbles remain a significant problem in football, even at the highest performance levels and currently remains an insoluble problem in the sport for amateurs and professionals alike.

Individuals who play basketball also have to both 'feel' and grip a ball to perform properly, and although they too could significantly enhance performance in controlling a ball; prior art forces them to choose all feel as well, and go without any type of grip enhancers. This insoluble problem therefore also exists in playing the sport of basketball, and these players would substantially benefit from developing a way to maintain feel while increasing grip capabilities in select areas of the hand. More specifically, new art is needed that could offer grip enhancers in certain locations of the hand while leaving others areas of the hand uncovered and therefore better able to maintain necessary feel.

In the field of Golf, to be sure, there exists much prior art in the form of golf gloves for a golfer's weak (non-dominant) hand. In fact most active golf players wear a gloves on their weak hand, and go without a glove for their strong hand (if one were to go to any major store to buy golf gloves, they would be sold and packaged in singles—one glove—not sold in pairs). Gloves are prevalent in golf largely because of the role that hand grip and control play in a golfer's overall performance.

Although there exist many types of full-fingered gloves for a golfer's weak-hand, they all attempt to maximize a golfer's weak-hand grip without regard to a golfer's weak-hand feel, and hand coordination needs. It is no surprise, therefore, that prior art consists of full-fingered (all fingers are covered), closed palm (entire palm is essentially all covered) gloves. As a result, a typical golfer must rely on her weak-hand to provide most of the grip support, and on her strong-hand to provide all of the 'feel' in her golf swing. The current solution to this insoluble problem has been for virtually all golfers to use one and only one glove. This glove is always placed on the weak hand, leaving the strong hand without a glove. There is, therefore, an opportunity to invent a device or method that could offer some 'feel' ability for the weak-hand, without significantly diminishing that enhanced grip ability that gloves offer. This would increase overall hand control of a golfer's club swing, and therefore, result in greater success in competition.

Whereas weak-hand support products seem to be crowded in the sport of Golf, there is a long existing need for a device that could offer added support for a golfer's strong-hand without significantly diminishing one's ability to adequately feel the golf club. Inventing a solution to this problem could, among other things, allow for greater overall golf swing control and consistency, and create an entirely new market because golfers currently do not use grip enhancers on their dominant hand, thereby changing the way that golf is played.

In Golf magazine's April 2005 article titled "Fix your grip. The wrong grip can cripple your swing—Here's the cure," golf instructor Charlie King provides an overview of how to grip a golf club. "Good golf starts with your grip. The proper hold on the club helps you do three crucial things: Hinge your wrists, control the clubface at impact and support the club throughout the swing. Here are three simple grip tips." As King continues, his third tip is "both hands; solid at the top. An effective grip sets the face square at the top, with the shaft parallel to the target line. You should feel most of the club's weight in your left thumb and right forefinger. Now you're ready to turn it loose." Although prior art seems to be crowded in offering a glove for the weak-hand, to support and better control the club weight placed on the thumb of the weak-hand, there remains an unmet need for added support on or around the forefinger of the strong-hand. Additionally, constant swinging of a golf club at real swing speeds often results in soreness on and between the thumb and forefinger of a golfer's strong hand (wearing no glove). This soreness can often also come from the rubbing or slipping, between the club handle and the strong-hand, suggesting a need to find a way to increase the grip—as well as protection—of a golfer's strong hand. This is especially important in the sport of golf because even the smallest of slipping—during the golf swing or upon impact of the golf ball—can create enormous inconsistencies and inaccuracies, critical issues in determining overall performance.

Consequently, there are clear indications that an entirely new market exists for targeted grip enhancers that could be placed only on select areas of the strong hand—such as only on a couple of fingers—leaving other parts of the strong hand free to feel. In particular there remains an unrecognized problem and an unmet need for new art that can provide multiple benefits, such as increase overall grip, improve coordination with both hands, as well as possibly provide some protection from any constant grip slipping, during the practice or play of golf, and in various other sports activities.

In the sport of Basketball, there exists no prior art when it comes to grip enhancers to enhance the performance of over 100 million individuals who play the sport. Although there are several multisport gloves in the market today, virtually no one uses gloves when playing basketball. A primary reason why basketball players choose not to use gloves, as mentioned briefly above, is just like with football quarterbacks, basketball players often need to be able to both grip and feel the ball. Although many hand tasks require a good grip, no art currently exists that would adequately provide these players with enhanced grip capabilities, or enhanced protection, without having to sacrifice the critical ability of being able to properly feel the basketball as well.

One clear hand task in basketball is in shooting the basketball with the intention of making a score or basket. Conventional jump-shot shooting form requires, among other things, that the player hold the basketball largely with the fingertips of both hands, and creating a small opening—or a shooter's gap—between the ball and the palm area of the player's strong-hand. No prior art exists that would increase the gripping abilities of a players fingertips and leave the rest of the hand uncovered and thus free to feel if the basketball is touching the palm area (indications that would mean that the player is improperly shooting the basketball).

Prior art is lacking that would provide an athlete with the ability to have enhanced control when dribbling a basketball. Proper dribbling form is to rarely, if ever, look at the ball while dribbling said ball—thus one of the critical reasons why one needs to be able to maintain high 'feel' ability. Without any extra grip enhancers however, it can become difficult to maintain stable control of the basketball.

A typical game—even a professional game—often can have as many as 30 turnovers (combined), so offering art that could increase ball control while dribbling, passing or even catching a basketball could significantly enhance performance by, among other things, minimizing turnovers. For example, minimizing turnovers by offering a finger cot adapted for basketball play would dramatically enhance a player's performance in the sport. Those players playing the position of Guard may benefit from added grip support especially because they may need to dribble, at least briefly, with their strong hand as well as with their weak hand. Whereas many players would benefit from control enhancers for their strong (dominant) hand, most guards would certainly benefit from control enhancers for their weak hand.

Although athletes playing the position of Forward or Center would also benefit by enhanced dribbling abilities, most of the turnovers caused by Forwards and Centers are often the result of dropping passes thrown to them, or from making a bad pass. Offering art that would enhance the ability to better pass or catch a basketball could therefore also enhance overall performance for anyone playing the sport of basketball.

Other general hand task challenges that are in need of a better solution have to do with basketball players who injure, in some way, their hand. In this situation the player has to tape her hand, especially when injuring a finger. The result again is a decrease in ball control and limited protection. To protect the injury, most players will choose to tape the finger and try to adjust. Loss of dribbling control can often result, as will loss of ball control when preparing to shoot the ball (and it slips out of the players hand and flies aimlessly in to the air).

There are several non-sport hand tasks that would benefit from new art, including:

- Massage therapists who may want limited protection on a select number of fingers but would seem as very inappropriate if they chose to wear a tubular member.
- Elderly who use walkers and want only a modest increase in control
- Activities such as basic yard work that don't require much hand protection

DETAIL DESCRIPTIONS OF THE INVENTION

The present invention provides tubular members in the form of sports finger cot embodiments, as well as tubular members in the form of sports sleeves for the forearm and arm area, configured to meet the unique needs of users playing various sports, including football, golf, and basketball.

The finger cot embodiments provide a tubular member, with a first end and a second end opposite the first end. The first end is closed and the second end is open and adapted to allow a user to place his or her finger inside said tubular member, or finger cot. Embodiments can be adapted to fit snugly around a digital segment of a human hand, such as a thumb or finger. The tubular member further comprises of a palmar side and a dorsal side, each of generally the same length and width. The tubular member may be constructed by any standard method, such as by conjoining a palmar portion and a dorsal portion by stitching, but leaving the second end opened, or unstitched. The palmar portion and the dorsal portion may be formed of different materials, and then conjoined. The palmar portion and the dorsal portion may also be formed of the same materials, and therefore may be integrally formed.

The sport sleeve embodiments provide a tubular member, with a first end and a second end opposite the first end. The first end and the second end are open and adapted to allow a user to place his or her arm inside said tubular member, or sport sleeve. The tubular member further comprises of a palmar side and a dorsal side, each of generally the same length and width. The sport sleeve tubular member may be constructed by any standard method, such as by conjoining a palmar portion and a dorsal portion by stitching, but leaving the first end and second end opened, or unstitched. The palmar portion and the dorsal portion may be formed of different materials, and then conjoined. The palmar portion and the dorsal portion may also be formed of the same materials, and therefore may be integrally formed.

The present invention also comprises of a grip enhancing means along the surface of the embodiment, such as, for example, PVC (PolyVinyl Chloride) dots, along the tubular member, such as along portion of the finger cot overlaying a user's distal phalanx.

Accordingly, embodiments provide novel tubular members with added grip-enhancing features that enhance overall control and sports performance compared to simply using the skin of the arm, forearm or fingers to grip something while engaging in sports activities.

In at least one embodiment, the entire outer palmar surface comprises of a grip enhancing means throughout said surface area. The grip enhancing means permits the individual to better grip a ball or an object or device, and can create, for example, a higher coefficient of friction than what the skin of a user might offer. This could give, for example, a football quarterback or a golfer multiple benefits such as increased control of a ball or device thereby enhancing performance and overall success at performing a sports task.

In general, the grip enhancing means of the present invention may be integral to the tubular members or may be permanently affixed to the tubular member surface by, for example, forming a grip enhancing panel and applying the panel onto a portion of the tubular member. The grip-enhancing means of an embodiment could comprise of, for example, a high friction textured surface with a more narrow width, say about 1.5 to three centimeters. This and other embodiments may include a plurality of projections on the surface as the gripping means formed from, for example, one of a vinyl material, a rubber material, or a neoprene material, creating a grip enhancing panel. The material forming the panel could then be permanently applied to said tubular members using any standard bonding methods, such as adhesion or stitching. The projections can preferably be provided, for example, on at least one centimeter by one centimeter of any tubular member. The projections could preferably extend out less than 1/10 of a centimeter, but could range generally from 1/20 of a centimeter to several centimeters.

In general, the panel may preferably be formed from an elastic material or fabric, including but not limited to, a knitted fabric, for example, LYCRA, rayon, neoprene, a rubber material, a vinyl material, or the like. Once the grip-enhancing surface on the panel has been formed, the panel may then be applied to the palmar surface of the tubular member by any standard methods, such as by stitches or adhesives, for example.

In general, the grip enhancing means of the present invention creates a higher coefficient of friction on the tubular member, and can be comprised of various grip-enhancing materials, coatings, and designs, including but not limited to, foams, fabrics, PVC dots, perimeter patching designs, linear and non-linear grooves, or combinations thereof, high friction surfaces, textured surfaces, a plurality of regular or irregular projections, a plurality of regular or irregular depressions, non-slip materials and designs creating coarse surfaces such as Emory cloth for example, as well as pebbled or beaded surfaces, convex or concave bumps, striations, cross-hatches, convex or concave linear and non-linear lines, angled ribs, random structures, convex or concave ridges, crevices, elongated segments, and the like.

Preferably, the depths of the depressions and/or heights of projections would be such that the gap formed by the depressions or projections would allow for some movement of the palmar surfaces thereby increasing the grip capabilities of the user. The height or depth ranges can generally begin at about 100 micrometers to several millimeters or more.

The grip enhancing means may further comprise a plurality of spaced apart stripes or striped projections formed from a high friction material, such as a PVC material, for example. Preferably the stripes comprise raised or projecting stripes and are arranged to extend generally parallel to the axis of any existing finger cots or sports sleeves. Stripes and other forms may be uniformly spaced or spaced at varying intervals. Similarly, stripes and other forms may have varying thicknesses, heights or depths, depending on preference. The thickness ranges generally can begin at about 100 micrometers to several millimeters or more. The grip-enhancing means may create a pattern, may be in rows or randomly placed, and may form circular and non-circular shapes, such as spherical, cylindrical or elongated projections or depressions. Additionally, they may be individually separated or interconnected.

In general, a dorsal surface of an embodiment can have a variety of finishes, one portion of the surface can have a smooth finish, for example, and the other portion can have a textured surface. The textured portion could create a coefficient of friction, or grip enhancer, on the surface.

The grip enhancing means may also comprise of coatings that enhance grip capabilities, including a latex coating, a neoprene coating or a PVC coating, for example, or non-metallic fibers.

The grip enhancing means can be formed on the tubular members by any standard method, for example, by embossing, stamping or molding a portion of the tubular member to create the gripping enhancing means. For example, the grip-enhancing means can comprise of regular projections of say, about 300 micrometers in height, but may vary in height depending on preference. The projections may all be the same height, and may be in rows. They may be embossed elongated shapes that are interconnected, thus creating a high coefficient of friction throughout the entire palmar surface area of the tubular member. Other embodiments could of course offer different heights, non-uniform heights, and have a more random pattern on the palmar portions forming the tubular member.

Alternatively, the grip-enhancing means may be attached, affixed or otherwise placed to select areas of the tubular member by standard methods and forms of attachment such as by overlaying a panel to select areas of the tubular member. This may be accomplished, for example, by creating a textured surface on a silicone-based layer and then hot melting said silicone surface onto the bottom surface of the most proximal end of an embodiment, thus providing a high friction surface on the embodiment. The grip enhancing means may be affixed to the tubular member by any other standard methods of attachment, such as by stitching.

Embodiments of the present invention provide a higher coefficient of friction than what the skin of user's finger, forearm or arm would otherwise provide.

More preferably, embodiments provide a Durometer A Coefficient of Friction of at least 1. Even more preferably, embodiments provide a Durometer A Coefficient of Friction of between 1 and 5.

In another preferred aspect, the present invention also comprises of protective properties to protect a user from injury or to protect an injury. A shock-absorbing member or members, such as a padded layer or layers may be used so that the tubular member can be used to protect an injury or to protect an area from being injured, for example.

The shock-absorbing member or members are generally located on the dorsal segment of the tubular member, where many football injuries occur as a quarterback throws a football and is immediately hit by an opposing player.

The shock-absorbing member may generally be affixed to the outer surface of the tubular member dorsal segment or may be integrally formed on the tubular member. If integrally formed, at least one embodiment may include a liner.

The thickness and dorsal surface locations of the shock absorbing members may vary, of course, depending on preference. In at least one embodiment the entire dorsal segment comprises a shock-absorbing member, and the shock-absorbing member can be one uniform cushion, for example, mirroring the design of the dorsal segment of the tubular member.

The shock-absorbing member can comprise of any material that could provide added protection to a user's thumb, fingers, hand, arm, or combinations thereof. In general, the shock-absorbing member can comprise of conventional materials for dissipating pressure across a surface area, can have varying densities and thicknesses, and can be in the form of a layer or multiple layers.

The shock-absorbing member may be flexible, compressible and/or resilient. The shock-absorbing member can comprise of, for example, any foam or cotton-based fabrics, cloth paddings, such as a cushion, foams such as a polyurethane foam pad, and flexible plastics, and the like, to absorb impact received from opposing players or from hitting the ground. It can comprise foam-filled segments, such as polyethylene foam pads, or it can be of cotton or cloth, or gels. For example, the shock-absorbing member may comprise of a unitary pad or pad segments, and may comprise any open cell or closed cell foam, such as BOLLARD foam, polyolefin foam and the like. The shock-absorbing member may also be made of any common materials used in providing tubular member padding, including natural or synthetic rubber, natural or synthetic rubber foams, gels, polyester fiber, or cotton or other natural or synthetic wadding materials. Additionally, it may comprise of foam possessing a substantially uniform cell distribution or polyvinyl chloride foam plastic.

The shock-absorbing member may comprise of cushions or pads which can be implemented as any of a variety of conventional padding material, such as foam rubber of varying densities and thicknesses, layers of fabric of various types and thicknesses, conventional gel or plastic material, liquid-holding compartments, or other types of conventional materials. The shock-absorbing member may also be fabricated from more rigid materials such as plastics or fiberglass materials. It will be apparent to one of ordinary skill in the art that many other implementations of the shock-absorbing member are possible.

The shock-absorbing member need not be very thick but can be, beginning generally from about 600 micrometers or so to several inches. The thickness may vary according to location, such as along the distal phalanx versus middle phalanx areas, and degree of desired protection, and is composed of a material which is compressible and bendable to protect a user from injury or to protect an injury.

The thickness of these embodiments may vary depending on several factors, such as for example, user preference. In other words, embodiments may be configured to absorb more or less by the thickness of the shock absorbing member. The embodiment can thus create a cushioning effect to, for example, protect an injury. For example, quarterbacks who rarely rush with the football may only require a thinner pad, say 0.25 inch or less, as opposed to quarterbacks who more often need to rush with the ball.

The shock-absorbing member is primarily located on the dorsal portion of the tubular member. Within that parameter, preferably, the shock-absorbing member can overlay any portion of any thumb and/or finger cot where a thumb and finger cot exists, and/or any portion of embodiments overlaying a user's forearm. In at least one embodiment, the entire dorsal segment comprises a shock-absorbing member, thereby generally mirroring the dorsal segment's design or structure of the tubular member.

Preferably, sport sleeve embodiments can also have a shock-absorbing member along the dorsal surface overlaying any portion of the wrist area including any of the carpometacarpal joints or the carpal bones, provided a segment overlaying the wrist exists. The shock-absorbing member overlaying the carpals on the wrist area may extend to also cover up to about five inches, and may do so as separate padding segments, for example, to allow for significant wrist flexibility, or may be configured as one pad.

The shock-absorbing member can be constructed on the tubular member using standard techniques placing paddings on tubular members, such as by stitching for example, or may alternatively be integrally formed on the tubular member. For example, the shock-absorbing member may be encased in a compartment or compartments that are then attached to select areas of the dorsal surface area of the tubular member. Alternatively, said compartments may be integrally formed on the tubular member and the shock-absorbing member could be interposed in the tubular member, with the compartment or plurality of discreet shock-absorbing protective protrusions projecting out from the tubular member.

The construction of these compartments may comprise of any flexible material, such as rubber, or may be of the same materials that form the tubular member. Said compartment or compartments could house and allow said shock-absorbing members to project out to provide protection in desired areas along generally the dorsal surface of the tubular member, or may be stitched onto the dorsal surface area of the tubular member.

By way of example, if the shock-absorbing member is placed onto the outer surface of the dorsal segment, it is envisioned that the pad could be sewn, bonded or otherwise attached atop the dorsal segment of the tubular member. A shock-absorbing member could include an outer layer of material which encapsulates the pad and enables the outer periphery of the pad to be positioned without damaging the pad. For example, it is envisioned that the pad may include an outer layer made of the same material as the rest of the tubular member, or may be a heavier, thicker material, such as synthetic leather. The shock-absorbing member, in this case a pad, is then inserted into the compartment. The compartment can then be sewn, adhered to or otherwise secured on the tubular member, such as deposed adjacent the dorsal segment of a thumb finger cot.

The shock-absorbing member may also be integrally formed on the tubular member. For example, the shock-absorbing member may be located between the inner surface of the dorsal segment of the tubular member, and a liner.

The liner material would therefore be positioned between the shock-absorbing member and a user's skin. The liner could be attached to the tubular member by standard methods, such as by conventional stitching about the perimeter of the dorsal segment, whereby the padded layer would be inserted and then sealed.

A similar method if the shock absorbing member is integrally formed on the sports tubular member comprises a flexible, preferably integrally molded dorsal member which has a tougher outer protective surface and a smooth skin contacting inner material, such as a liner, being connected together around the peripheral edge of the molded member. The outer member may have a plurality of discrete shock-absorbing protective protrusions whereby the shock-absorbing members could be housed. The protrusions may be in a variety of heights and shapes, and of sufficient dimensions to house each shock-absorbing member.

The lining material may be comprised of standard lining materials, such as a smooth, flexible knitted fabric. The liner may also comprise of flexible and elastomeric material such as spandex or LYCRA. Other possible materials include a knit of polyester or simply the same material forming the tubular member. A soft cellular plastic could also be preferred. Additionally, the liner may provide added features to offer warmth and comfort such as by comprising of a fleece material, for example, especially useful when competing in the rain or snow.

These novel features will give a quarterback added protection from the abrasion of hitting a user's fingers against the helmet of an opponent, for example, or while wrapping his throwing hand around the football when rushing. The shock-absorbing member sections of the present invention offer the unique ability of being able to protect an injury while maintaining grip capabilities in select areas by offering padded layer or layers, a significant and substantial advancement to prior art, such as bandages, thus providing a solution to a long-felt need of being able to protect a quarterback's throwing hand.

Some embodiments, of course, will not have a shock-absorbing member on any part of the tubular member. These embodiments that are absent of any shock-absorbing member will be useful and significantly beneficial to football quarterbacks but also especially to those playing the sport of golf, primarily because the unique configurations of the tubular member allow a user to place grip enhancing capabilities only along certain portions of a hand or arm while leaving the rest of the hand or arm uncovered, and thus maintaining necessary 'feel' competencies.

Accordingly, embodiments can also provide novel tubular members with added protective features that enhance protection of a previously unprotected quarterback's throwing hand, for example, by offering padded finger cots adapted for outdoor football play.

The tubular member may also have an expandable securement opening means at an open end adapted to receive the user's hand. This may comprise of, for example, a strap which mechanically engages a strap/flap capture mechanism to secure the tubular member (e.g., a synthetic hook and loop fastening interface which adheres when pressed together, commonly using VELCRO). In this case the strap could overlay a small slit or opening along the embodiment's dorsal portion to allow the tubular member to widen when a user places the tubular member on to the finger or arm. Alternatively, the opening means may comprise of other standard used mechanisms of allowing a user to apply and disengage the tubular member, such as an elastic band material along the open end of the finger cot or along both open end of the sports sleeve, or combinations therebetween. The securement opening means may alternatively comprise an elastomeric band fixed around the open ends of the embodiments. Embodiments may also have combinations of both a strap capture mechanism and an elastomeric band. The expandable securement opening means may be formed integral with the tubular member or may be attached to the tubular member by standard methods, such as by sewing.

Embodiments may also comprise of micro holes along any portions of the tubular member, generally used on golf tubular members and football tubular members for ventilation or moisture management purposes. These micro holes are generally about 0.120 millimeters or so in diameter.

In general the present invention offers enhanced grip capabilities for a user's finger and in select areas of the arm and/or the hand.

Embodiments can comprise of various weather-resistant and/or perspirant-resistant woven and non-woven materials including but not limited to water-resistant materials or hole designs for moisture management, or combinations thereof.

Some embodiments may additionally or alternatively comprise of a weather-resistant or moisture-resistant coating, such as a synthetic resin or SCOTCH GUARD, applied to the materials forming the embodiment in order to be moisture repellant.

Providing a moisture resistant feature to finger cots, for example, now allows athletes with the ability to use finger cots during active outdoor sports play such as football, basketball and golf.

Furthermore, embodiments could comprise various types of stretch materials and designs, mesh fabrics, recycled and flexible materials, rayon, spandex, fleece, rubbers, plastics, polyester, or combinations thereof. Materials may also comprise of woven materials such as natural, synthetic or blends of natural and synthetic yarns, thermoextruded or thermoset rubbery embodiments such as those made from thermoplastic elastomers. Examples of synthetic yarns include nylon, polyester, and SPANDEX (polyurethane) yarns. Embodiments may also comprise of cottons, leathers and synthetic leathers, non-woven fabrics, cloths, LYCRA, a vinyl material, a neoprene material, or combinations thereof.

When the palmar portion is formed of a more durable material, such as leather or synthetic leather for example, it may be preferable, at times, to form the dorsal portion of a different, more elastic material to allow for greater finger movement capabilities. Alternatively, at times, when the dorsal portion of the embodiment is also formed of a more durable material, it may be preferable to provide an aperture along the dorsal portion of the finger cot whereby a user's finger joint may be exposed, allowing the finger or arm to maneuver more easily. Such as, for example, providing an aperture along the dorsal portion of some embodiments whereby said aperture leaves exposed, for example, a user's entire middle interphalangeal joint.

It is commonly known that wrist bands have been constructed with perspiration absorbing capabilities, allowing an athlete to wipe perspiration away from their face during competition. Where wrist bands are not commonly used, such as in football or golf play, the athlete is currently left deficient in this area. Some embodiments of the present invention provide this capability, by providing a layer of terry cloth, mesh, or other moisture absorbent material such as an absorbent foam, for example, affixed along the dorsal portion of the tubular member.

Construction of the present invention may be accomplished by standard methods of forming tubular members, including finger cots and sport sleeves, such as, for example, by designing the dorsal and palm sections to meet along a conjoining lateral edge to define a pocket for receiving the eminence of a user's finger, forearm or arm.

Tubular Members Embodiments for the Hand-Finger Cots for Sports Wear

The present invention provides tubular members in the form of sports finger cots embodiments, configured to meet the unique needs of users playing various sports, including football, golf, and basketball.

These finger cot embodiments are adapted to overlay up to one digital segment, such as a user's pinkie finger, but does not extend to overlay a second digital segment. For example, embodiments may be configured to overlay the entire forefinger of a user, but would not extend to overlay a second finger, such as the user's middle finger. If a user desired, he or she could use a finger cot embodiment to overlay his forefinger, and then place a second finger cot embodiment over his middle finger. Finger cot embodiments enclose at least essentially the entire distal phalanx and at least a portion of the middle phalanx of a user's digital segment.

As mentioned, one unique feature offered by the present invention comprises a grip enhancing means along the outer surface area of the embodiment. These finger cot embodiments may comprise of a grip enhancing means along, for example, the palmar portion of the finger cot. For example, a finger cot embodiment may comprise of a grip enhancing means along its palmar portion overlaying the distal phalanx of a user's forefinger—or the fingertip. At least one embodiment provides a grip enhancing means along the entire palmar portion of the embodiment.

These finger cot embodiments may also comprise of a grip enhancing means along the dorsal portion of the finger cot. For example, finger cot embodiment may comprise of a grip enhancing means along its dorsal portion overlaying the entire distal phalanx of a user's pinkie finger.

These finger cot embodiments may further comprise of a grip enhancing means along either side, or along both sides, of the finger cot. For example, a finger cot embodiment may comprise of a grip enhancing means along its side overlaying the distal phalanx of a user, adjacent a user's ring finger. At least one embodiment provides a grip enhancing means along both sides of the embodiment, in its entirety.

As discussed, the finger cot embodiments of the present invention provide a higher coefficient of friction than what the skin of user's finger would otherwise provide.

A further feature that these finger cot embodiments may provide comprises of a shock absorbing member, for added protection.

These finger cot embodiments may comprise of a shock absorbing member along the dorsal portion of the finger cot. For example, finger cot embodiment may comprise of a shock absorbing member along its dorsal portion overlaying a user's proximal phalanx. At least one embodiment provides a shock absorbing member along the entire dorsal portion of the embodiment.

These finger cot embodiments may further comprise of a shock absorbing member along the side of the finger cot. For example, a finger cot embodiment may comprise of a shock absorbing member along its side overlaying a user's proximal phalanx. At least one finger cot embodiment provides a shock absorbing member along the entire side of a user's pinkie finger, opposite the user's ring finger.

As mentioned, the present invention may further provide microrecesses along its surface, for moisture management purposes.

For example, a finger cot embodiment may comprise of microrecesses disposed along its dorsal portion overlaying a user's proximal phalanx. Alternatively, or additionally, finger cot embodiments may comprise of a moisture-repellent substance sprayed on its fabric and thereby making the embodiment better equipped for active sports activities, such as football or golf.

Finger cot embodiments may also have an expandable securement opening means along the open end adapted to receive the user's finger, thereby providing a more secure and snug fit.

Finger cot embodiments may further comprise of a liner within the embodiment, adapted to provide some separation between the inside surface of the finger cot and the skin of a user's finger. The liner may provide added features to offer warmth and comfort such as by comprising of a fleece material, for example, especially useful when competing in harsh conditions. A liner feature may also be provided if the finger cot embodiment provides a shock absorbing member within the finger cot, to help house the shock-absorbing member.

Finger cot embodiments may further comprise of a moisture absorbent material along the dorsal surface of the embodiment, allowing an athlete to wipe perspiration away from their face during competition. Where wrist bands are not commonly used, such as in football or golf play, the athlete is currently left deficient in this area. Some embodiments of the present invention provide this capability, by providing a layer of terry cloth, mesh, or moisture absorbent material such as a foam, for example, affixed along the dorsal portion of the tubular member finger cots. For example, finger cot embodiment may provide a terry cloth material along the dorsal portion overlaying a user's proximal phalanx.

One sport where finger cot embodiments of the present invention will clearly enhance performance is in the sport of football. For example, one particular unmet need that embodiments will satisfy will be with football quarterbacks (though receivers could benefit from this also). In the book "coaching football successfully," by Allan Trinkle (2001) "quarterback mechanics and ball-handling skills are vital for offensive success and consistency." One embodiment of the present invention comprises a series of finger cot embodiments that could be used simultaneously. Specifically, for example, grip enhancing finger tubular members—or finger cot—could be used to independently cover two fingers: one over the thumb and the other over the forefinger of a user's hand. These finger cot embodiments would allow a quarterback to increase his ball grip and overall control of a football, while still allowing some vital finger feel of the football as well (by leaving the remaining three fingers uncovered). These embodiments could be made of a natural rubber, having PVC dots throughout the outer surface, and having an opening securement means in the form of an elastic component at the open end of the finger cots, to create a tight, secure fit.

Because football is played outside (or outdoors), these embodiments might be made of moisture-resistant fibers as well, or alternatively may be sprayed with a moisture-repellant substance such as, for example SCOTCH GUARD. The benefits to the user of these embodiments would include: better overall grip and better control in holding and throwing a football, higher throwing accuracy, and less fumbles.

These finger cot embodiments would take into account the benefits of the laces on a football, and give a quarterback the unique ability to grasp a football over the football laces on a football, with the comfort and feel of not having a tubular member or even a glove, while adding the support that a glove might provide, over the thumb and forefinger. No prior art offers this unique type of support and ability for outdoor sports play, such as football. These embodiments would therefore increase grip capability on select fingers, while leaving the rest of the hand uncovered and able to maintain the necessary 'feel' of the ball, something that prior art cannot do. If a quarterback prefers placing only two fingers over the football laces, then the quarterback could add a third finger cot embodiment and place it over the middle finger as well. The present invention therefore allows a quarterback to tailor these grip enhancing finger cots to conform to one's particular football throwing grip preferences. The resulting stronger overall grip should make for a much higher success at throwing a spiral, and generally higher consistency and performance in ball handling and control.

In addition to offering greater throwing accuracy and consistency, these and other embodiments could also help minimize quarterback fumbles by adding gripping support when completing other quarterback tasks, such as when 'pumping' the football, scrambling from being tackled, and even when catching and passing the football, especially when in 'shot gun' formation (when a quarterback has no time to glance at the football and must solely on feel to properly grasp and throw a football).

Another sport where the present invention will meet an unmet need is in the sport of Golf. Many finger cot embodiments can be used in conjunction with each other to uniquely solve problems that have up until now been unsolved. As mentioned, gloves are not used on a golfer's dominant hand because of the structural limitations of prior art. For example, a golfer may want to enhance the grip around some fingers but might also want a couple of fingers uncovered as so to maintain critical feel sensitivities.

New art in the form of grip enhancing finger cots to support a golfer's strong hand would now allow a golfer to select which fingers she wants covered and which she wants to remain uncovered. The benefits of this significant and substantial physical difference in this new art could change the way that golf is played by among other things, offer the golfer a more stable overall grip, better control and enhanced performance.

For example, one solution for a golfer's strong hand comprises using three finger cot embodiments, one that covers each of the strong hands' thumb, forefinger and middle finger, leaving the ring finger and pinkie finger uncovered. The 'feel' and coordination tasks could therefore be maintained with the ring and pinkie fingers by leaving these fingers uncovered, while enhancing the overall grip of the strong hand by covering the strong hand's thumb, forefinger and middle fingers. These finger cot embodiments therefore offer the golfer a much improved method of playing the sport of golf by using grip enhancers not just on the weak hand but also on the strong hand as well, without limiting the feel and coordination requirements in a proper golf swing. These embodiments, for example, could be made of synthetic rubber, having non-linear grooves throughout the embodiments.

Currently, only full-fingered gloves exist for golfers, regardless of one's preferred golf grip. Embodiments of the present invention could offer significant improvements to glove alternatives, by allowing a golfer the ability to select which fingers she wants covered and which ones she doesn't.

One very popular grip, for example, is called the 'interlocking grip.' When one uses this grip, the forefinger of the golfer's weak hand—which is covered by a conventional golf glove—is placed over her strong (dominant) hand—which is not covered by a glove—and interlocked with the strong hand's uncovered pinkie finger. With the present invention, if a user desires to increase her hand coordination, she can now use finger cot embodiments to increase the feel between the two interlocked fingers; if she wants to increase her grip between her two hands, she can now place grip enhancing capabilities on both interlocked fingers.

For example, she could choose to have four individual finger cot embodiments to cover all the fingers on her weak hand, except the forefinger. These embodiments could be made of the same material used to make a typical golf glove, such as rubber or synthetic rubber. Each finger cot embodiment could have a slit on part of the embodiment's top—or dorsal portion so to make it easier to place on each finger. Among the results would be that she could maintain grip on the fingers that actually grip the golf club—the thumb, middle finger, ring finger and pinkie finger—while being able to increase the feel of her weak hand forefinger, the one that's interlocked with the strong hand's pinkie finger, and the benefits could be a more effectively controlled golf swing and greater golf swing consistency.

Alternatively, the golfer may simply prefer to add a finger cot embodiment on just the pinkie finger of her strong (dominant) hand. The result would be that all the fingers would be covered on her weak hand—by the use of a conventional golf glove—and the pinkie finger of her strong hand would be covered by a grip enhancer as well—by a pinkie finger cot embodiment. This general idea clearly also would apply to someone gripping a golf club with the 'overlapping' or 'full-fingered' method (See FIG. 5).

Another possible outcome in the way golf is played may be in how one handles a golf putter. Current proper form is not to use a glove. If one were to watch a professional golf tournament for example, nearly all golfers would use one golf glove (placed on their weak hand) that they would use to grip a club for the tee shot swing, the fairway swing and even the short, approach swings. Once the golfer was ready to use their putter and putt the golf ball, they nearly always take their golf glove off, deciding to grip the putter with both hands uncovered (without any sort of grip enhancer, such as a golf glove). Finger cot embodiments could be used to modestly increase the player's grip while allowing her to maintain heightened finger sensitivities—something that golf gloves cannot offer. These finger embodiments may be made of a softer mesh fabric and perhaps a smoother surface but also with a griping coating or compound, such as PVC coating on the embodiment's palmar portion, and would now allow a golfer to choose, if she prefers, to increase the grip she has on her club, modestly, while maintaining a heightened overall feel of the putter as well.

For example, the golfer could choose to keep her overall feel of the putter very high by not using a golf glove on either hand. However, she could then decide to use a thumb finger cot embodiment on her dominant hand and a pinkie finger cot embodiment on her weak hand, thereby also modestly increasing her grip at both ends of her hand grip along the shaft of the golf club. Even a slight increase in control of a putter can make a very significant and substantial difference in performance, especially if one 'drives for show and putts for dough.' These finger cot embodiments might also have an opening securement means along the embodiment's dorsal portion for easy removal, with VELCRO on both sides of said opening.

Another sport where grip enhancing finger cot embodiments of the present invention would meet unmet needs would be in the sport of basketball.

Individuals who play basketball have to 'feel' as well as control a ball to perform effectively (as mentioned previously), and although they too could significantly enhance performance in controlling a ball by using grip enhancers, prior art forces them to choose between all feel (and therefore, no glove) or no feel, and go without any type of grip enhancers. These players would substantially benefit from developing a way to maintain feel while increasing grip capabilities in select areas of the hand, thereby solving this significant issue. This insoluble problem can now be solved by finger cot embodiments of the present invention.

One solution that would help a player shoot a basketball better comprises of five individual finger cot embodiments. These embodiments would allow the rest of the hand, including the palm area, to remain uncovered. For all basketball players, but especially for those who have trouble shooting free throw shots or shooting outside of the perimeter, the uncovered palm area keeps feel sensitivities high in that area, so as to allow them to feel when they are using bad shooting form, because a basketball should rarely touch the palm area when properly shooting a basketball.

Finger cot embodiments could also satisfy the necessary requirements in dribbling a basketball. According to the book "Basketball for High School Players and Coaches," (1955) Carl Bachman describes proper fundamentals of basketball dribbling: "Certain fundamentals apply to all phases of ball handling: Looseness of finger and wrist action is important, practice spinning the ball on fingertips; a basketball should never touch the heel of the hand and seldom, if ever, touch the palm."

Because proper dribbling form also discourages the ball from touching the palm area, covering the palm area with, say a glove, would not only be relatively useless in basketball, but also a waste of resources. The present invention's finger cot embodiments would allow a player to avoid covering her palm area and instead concentrate her enhanced gripping abilities in the most important area when it comes to shooting; the fingertips. One embodiment of the present invention could comprise of a finger cot embodiment configured to overlay a user's thumb and a finger cot embodiment configured to overlay a user's forefinger, for each hand.

These embodiments could help a dribbler develop and use proper dribbling form, especially on her weak-hand. These finger cot embodiments would more generally help any player, and likely could be used, for example, by those playing the position of Guard while practicing proper dribbling on their strong-hand, as well as Forwards and Centers during actual game play for added support on their weak-hand.

These finger cot embodiments could be designed, for example, with a grip enhancing means— such as PVC dots or horizontal grooves—only on the fingertips, or along the embodiment's palmar portion overlaying a user's distal phalanx. They could be made of a stretch fabric, such as nylon, comprising of its dorsal portion, and a more durable fabric, such as cabretta leather, comprising of its palmar portion. The result would of course be a better overall grip and a significantly superior alternative to the prior art of conventional multisport gloves that cover the hand completely, once again forcing the basketball player to lose much of the critical requirements of being able to feel the ball.

Another finger cot embodiment for enhanced general basketball play could comprise of finger cot embodiments adapted to separately overlay the thumb, forefinger and middle finger of both hands. All six fingers are all individually and separately completely covered or enclosed, including the fingertips. As a result, the palm area would therefore be uncovered. These finger cot embodiments would give a basketball player the ability to better catch a ball, thus eliminating the consistent problem often found in Forwards and Centers losing control of passes. These embodiments would also provide a player with a stronger grip on the ball by providing added grip along these fingers, when passing a ball as well as provide some moisture management control, thus minimizing turnovers often caused by passers, especially in Guards.

A secondary but still important feature is that embodiments may help individuals slamdunk a basketball by helping the player to grip the ball using only one hand, a major benefit to those with smaller hands. This feature would provide added grip support and greater performance in slamdunking.

Although many hand tasks require a good grip, no art currently exists that would provide these players with the ability to maintain some grip capabilities while at the same time trying to protect the hand from injury, or trying to protect an already injured hand. Finger cot embodiments of the present invention would allow a player to be able to apply some sort of protection on select fingers, without having to sacrifice the critical ability of being able to properly grip the basketball.

A very common occurrence when playing the sport of basketball is a player having to tape her hand after, say, injuring a finger. The result again is a decrease in ball control and limited protection. These grip enhancing finger cot embodiments could also allow a player to tape her finger first, and then slipping a finger cot embodiment over the tape. Alternatively, one embodiment could include shock absorbing member in the form of a padded interior, for example, which might result in the player not needing tape to protect an injury. These finger cot embodiments would be substantially superior because they would be able to protect a finger injury (with the padding) while not diminishing grip The shock absorbing member may comprise of any cushiony fabric. These embodiments could offer a lightly padded interior along the dorsal portion for extra protection, while having PVC dots on the palmar portion surface, for increased grip capabilities. The padding could range anywhere from 1/16 inch to 1/3 inch of cotton fabric padding, for example. Among the results would be a better device and method of providing added protection while playing basketball, and not sacrificing ball control.

Other sports which could benefit from embodiments of the present invention include, but are not the limited to, baseball (pitchers might just use a thumb finger cot embodiment to create more control of ball pitches) and volleyball (players might also just use a thumb finger cot embodiment having a grip enhancing means on both sides or the palmar portions outer surface of said embodiments, areas where the thumb make contact with the volleyball), and tennis (where a player may want to use, say a thumb and forefinger finger cot embodiment for increased grip, leaving the other fingers uncovered). Virtually any player in any sport may benefit from the present invention where hand use is involved, but particularly those engaging in outdoor sports play.

Finger cot grip enhancers of the present invention could certainly assist an individual more effectively perform activities outside of sports activities as well. Areas where finger cot grip enhancers would more effectively increase performance include, but are not limited to:

- Indoor activities where a tubular member is often burdensome
- Gripping daily household items like twisting off a tight lid
- Placing on just thumbs and forefingers when doing a manicure
- When gripping a hammer, wrench or other tools
- When players desire better grip capabilities only in select areas of the hand In general, the grip enhancing finger cot embodiments of the present invention can generally be used in conjunction with any type of hand task activity or sports play. As discussed, they offer an individual with the opportunity to increase overall hand task performance. Maintaining or increasing overall control, for example, can provide many benefits to a user of these, and other embodiments.

Among the many benefits of the hand task enhance embodiments are that they:

- Allow an individual to maintain or increase control of a ball or object
- Offer the ability to grip as well as feel a ball and/or device
- Provide the unique solution for players who desire better grip capabilities only in select areas
- Allow a player to protect an injury on a finger without losing significant grip capabilities—disadvantages that using prior art sports tape would create if not used in conjunction with these embodiments
- Give a means for players who want added protection to complete certain activities, such as playing basketball with an injured finger, without losing grip capabilities that the current art sports tape would create.
- Provide a player with the added convenience to select which fingers to cover and which fingers to remain uncovered, simply even just to maximize overall comfort during sports play
- Offer a more stabilizing overall grip of a ball or object, by conveying grip-enhancers to select locations of the hand.
- Improved performance in hand task execution
- Improved overall grip
- Improved stability of overall grip throughout the hands
- Increased control
- Increased consistency
- More hand coordination by adjusting enhancers to match one particular golf swing
- Less hand task control handles, such as basketball turnovers Users of the finger cot embodiments can benefit from:

- A grip enhancing surface along the fingertips of a user
- A grip enhancing surface along the back of a finger
- A grip enhancing surface along the sides of a finger
- A higher coefficient of friction than the skin of a finger provides
- A padded portion along the back of a finger
- A padded portion along the sides of a finger
- Microrecesses for moisture management during active play
- A moisture-repellent substance further wicking away moisture on a finger
- A strap on the back of embodiments, for a secure snug fit on a finger
- A liner for added comfort and support
- A terry cloth along the back of the finger, to easily wipe a face from sweat These are among the unique structural features that are offered by finger cot embodiments of the present invention.

Tubular Member Embodiments for the Forearm and Arm-Sport Sleeves.

The present invention provides tubular members in the form of sport sleeve embodiments, configured to meet the unique needs of users playing various sports, including football, golf, and basketball. These embodiments provide a tubular member, with a first end and a second end opposite the first end. The first end and the second end are both open and adapted to allow a user to place his or her forearm or entire arm inside said tubular member, or sports sleeve.

One sport where the present invention will clearly enhance performance is in the sport of football. For example, one particular unmet need that a grip-enhancing device for the forearm area will satisfy, will be with receivers. One embodiment of the present invention comprises a reusable forearm tubular member—or a sports sleeve for the forearm—that will allow a receiver to increase his overall ball grip and therefore control of a football especially when catching a football and attempting to complete a reception. This forearm tubular member sport sleeve could be designed to minimize movement on impact. This embodiment could also have PVC dots, forming an oval shape for example, along the dorsal surface to enhance one's grip, necessary for improved performance. A football player would slip this cylindrical shaped embodiment onto his arm, covering most or all of the forearm area. This embodiment could be made of natural rubber or natural rubber latex.

The circumference of this embodiment could be about 5 centimeters, being able to expand to about 8 or 9 centimeters. More generally, the circumference should be of sufficient size to fit snugly around the forearm of a user.

For a receiver, this and other embodiments would also allow the player to increase receptions and decrease fumbles, by being able to better cope with added stress factors, factors which would otherwise make for an unstable overall grip.

An embodiment that could offer greater consistency and enhanced performance would comprise of a grip enhancing cover that could temporarily cover the elbow pad that a football player currently uses. This embodiment—as an elbow pad cover—could comprise of a grip-enhancing design such as several grooves throughout the arm area surface. By allowing the player to continue to use his current padding for protection and preferred comfort while providing a new grip enhancing cover, this embodiment would enhance a player's ability to better absorb impact from the ground or from a defender—without losing control of the ball.

Additionally, this embodiment would minimize the possibility of the ball moving, once in the receivers grasp because, among other things, grip capability has now been enhanced throughout the arm. This embodiment could be crafted with a blend of polyester and LYCRA spandex for a tight fit. The circumference of this embodiment could be, for example, about 3 centimeters or more at each end while having a wider circumference in the middle portion, to allow for the embodiment to temporarily cover the existing, conventional elbow pad. Such as, for example, having a middle circumference starting at about 1.5 times wider than at each open end. This particular embodiment could be one tubular member cover, covering the wrist, forearm, elbow and bicep areas—essentially temporarily covering an entire arm pad with a grip enhancing cover. This grip enhancer might comprise of a latex coating with non-linear grooves. Other similar embodiments might only extend from the wrist through the elbow area, allowing the biceps to flex easier (being uncovered and therefore unencumbered), if a player prefers.

Embodiments could also significantly improve the performance of running backs or any player who runs with a ball. One embodiment of the present invention, comprising a reusable grip enhancing sports sleeve for the wrist area, would allow a player to significantly increase his ability to control or cradle a ball when running. This embodiment could be placed on the wrists to help stabilize control, thereby supplementing a grip of any glove that might be currently available and in use. This embodiment could also be used as a grip enhancer around the elbow area.

Specifically, two wrist enhancers might be used; one could be placed just below the elbow area and the other just above the elbow area, allowing a player to almost literally grab one end of the football with the elbow. Clearly, this would create a much greater, more stable overall grip because one would now have grip enhancers that one could use to increase ones grip on both ends of the football, with a glove on the hand holding one end of the football, and the grip enhancers on the elbow area holding the other end of the football. The grip enhancers could comprise of PVC dots throughout the surface area of the wrist embodiment, and the embodiment could be made of nylon and rubber, and be of sufficient size to fit snugly around the wrist of a user. These, and other embodiments, could also prove useful for quarterbacks who have a number of fumbles during a season.

Other sports, such as Rugby, could benefit from many of the described embodiments for many of the same reasons.

Embodiments of the present invention can offer significant and substantial benefits by offering the ability to better control a ball in select areas of the arm. For example, embodiments could be placed on primarily only the forearm area, allowing the player to have significantly enhanced control over a ball, much like a glove can help a players' hand better control a ball. In addition, these forearm sport sleeve embodiments offer new and surprising results when used in the sport of volleyball: they allow a player to impart much more spin on the volleyball—an added feature which could substantially impact the sport. This ability to impart significant spin on the ball could make it easier to control the ball upon contact, to strike a ball, to get the ball to a teammate, and to redirect the ball.

One particular sports sleeve embodiment could comprise of a reusable partial forearm sports sleeve. One could consider it very similar to the forearm cover previously explained except that this elongated grip member covers only part of the forearm. It could be made of materials similar to that of a typical glove, and offering similar benefits to that of a glove as well. Specifically, it could be made of a stretch, moisture-resistant fiber, with grooves along most of one side (allowing the player to impart more spin on the ball), and elastic material on the other side. As a result, one would now have significantly more ball control during volleyball practice or game play. After the activity was completed, one could then simply take off this embodiment, and store it for future play. It would have a common circumference throughout the embodiment.

In general, the grip enhancing sport sleeve embodiments of the present invention can generally be used in conjunction with any type of arm task activity or sports play. As discussed, these embodiments offer an individual with the opportunity to increase overall arm task performance. Maintaining or increasing overall control, for example, can provide many benefits to a user of these, and other embodiments.

Among the many benefits of the arm task enhance embodiments are they:

Allow an individual to maintain or increase control of a ball or object

Provide the unique solution for players who desire better grip capabilities only in select areas Provide a player with the ability to convey grip ability that can more evenly extend out further than just the hand.

Offer a more stabilizing overall grip of a ball or object by conveying grip enhancers to select locations of the arm.

Additionally, these embodiments can provide:

Improved performance in arm task execution

Improve overall grip

Improve stability of overall grip throughout the grip of a ball

More control

More consistency

Less ball mishandles

Allow athletes to use their current preferred pads and coupling them with grip enhancing covers These are among the many benefits of the present invention and is not to be construed as limitation of the benefits nor their legal equivalents Although the description of the present invention only discussed a few embodiments, it is understood that other non-sport and sport activities might benefit as well from the present invention and its legal equivalents. In addition, only some embodiments have been discussed and in no way is intended to limit all the various embodiments and other embodiments that the present invention provides, such as but not limited to, different designs. For example, embodiments can easily be developed for easy opening, where a part of the back of the forearm opens up, and is tightened using VELCRO (Velcro is a registered trademark). Additionally, these embodiments can be used by men and women, boys and girls, playing any position in sport, as well as those whose dominant hand is the right hand or the left.

BRIEF DESCRIPTIONS OF THE DRAWING

It is expressly understood that the following descriptions and drawing are for illustration purposes only, and in no way are intended to limit the scope of the present invention and its various embodiments.

DETAILED DESCRIPTION OF THE DRAWINGS

It is expressly understood that the drawings are for the purpose of illustration and description only and are not intended as a definition of the limits of the invention.

Figure 1:
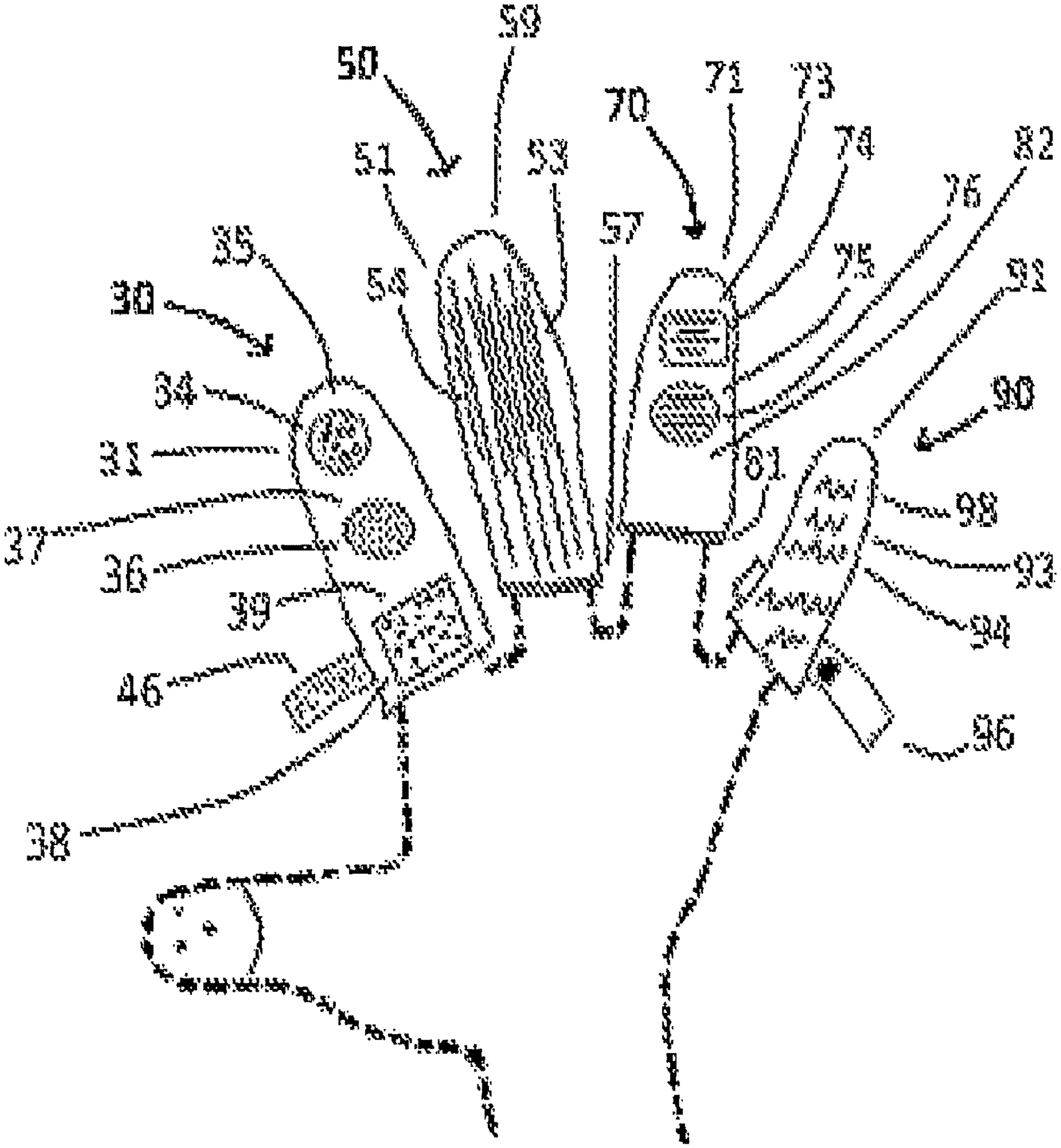
FIG. 1 is a drawing of several finger cot embodiments on the left hand of a user, showing the palmar surfaces.
Figure 2:
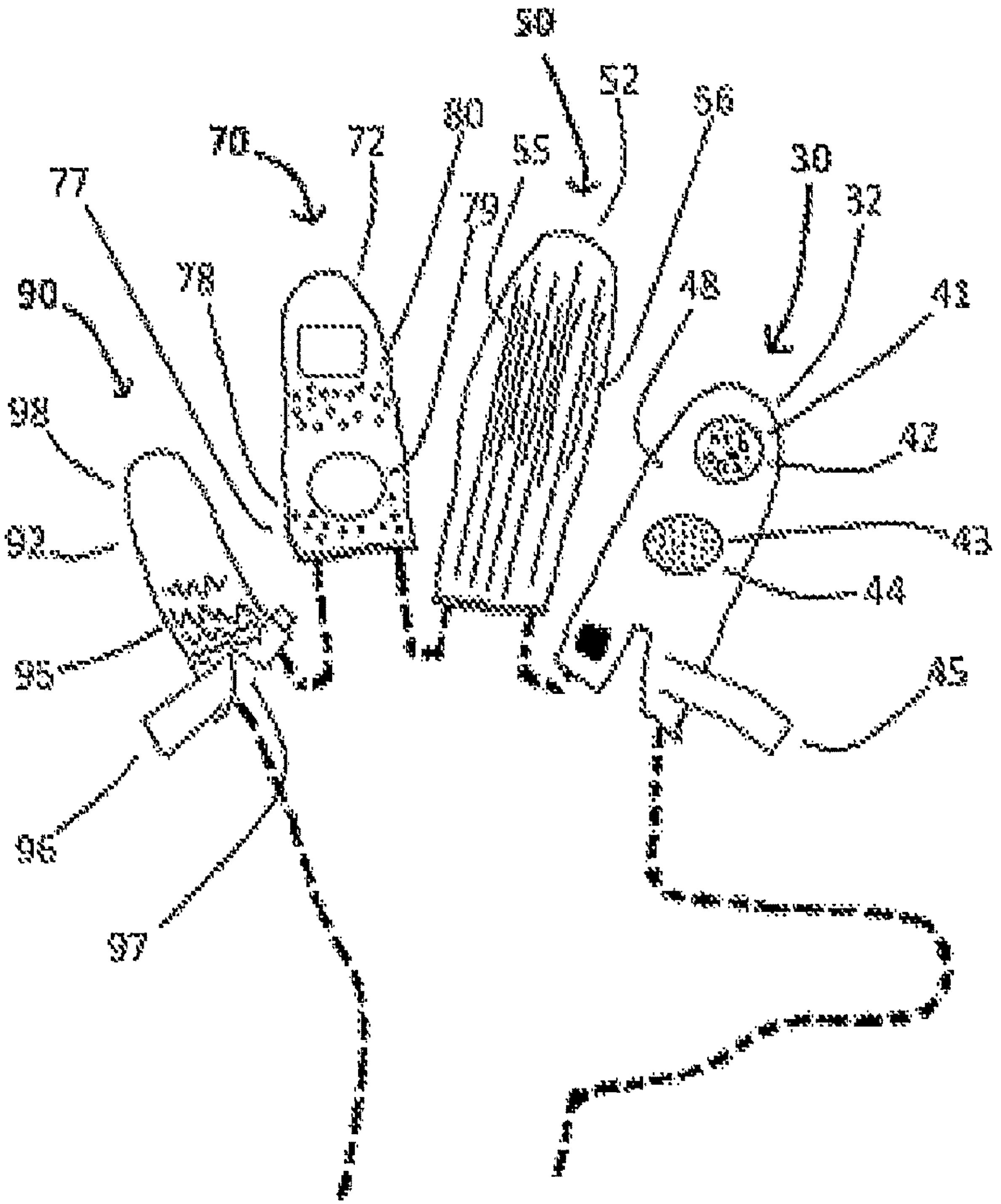
FIG. 2 is a drawing showing the dorsal surfaces of the embodiments in FIG. 1.

Referring now to FIG. 1 and FIG. 2, the present invention is shown as various grip-enhancing tubular members for placement around a user's digital segment. These embodiments, or finger cots, have a first end and a second end, the first end is closed and the second end is open and adapted to allow a user to place his or her finger inside the tubular member, or sports finger cot embodiment.

Shown on a user's left hand are four separate finger cot embodiments 30, 50, 70, and 90. Each embodiment could be used independently or in combinations. These embodiments should have a circumference large enough to be able to fit tightly around select areas of a finger, but do not extend to overlay a second finger.

One finger cot embodiment is shown and designated as 30. The palmar view 31 of the finger cot is drawn in FIG. 1, and the dorsal view 32 of the same finger cot is drawn in FIG. 2. It is adapted to overlay the entire distal, middle and proximal phalanges of a user 30, and offer a grip enhancing means to enhance a user's ability of controlling a ball or an object by providing a higher coefficient of friction than what the skin of a user might otherwise provide, preferably a Durometer A Static Coefficient of Friction of at least 1. More preferably, a Durometer A Static Coefficient of Friction of at least 1.5. The circumference of the embodiment is of substantial size to allow a user to fit the embodiment snugly on a digital segment of a user, such as a user's forefinger. The palmar and dorsal portions are essentially the same size.

The palmar portion (or front) can be constructed primarily of any flexible, resilient material aforementioned, for example, a latex or synthetic latex 31. It offers a grip enhancing means, such as PVC dots, for added grip support in controlling a ball or object. Specifically, the palmar portion overlaying a user's distal phalanx comprises of a circular panel 34. Formed on the panel is a plurality of PVC dot projections 35 of at least three hundred micrometers. The panel can be composed of any panel forming materials aforementioned, such as a neoprene material 34, and is affixed to the finger cot by any standard method, such as by stitching. The panel extends to overlay most of the distal phalanx area of the palmar portion 35. The palmar portion overlaying a user's middle phalanx comprises of an oval panel 36. Formed on the panel is a plurality of PVC dot projections 37 of at least two hundred micrometers. The panel can be composed of any panel forming material aforementioned, such as a vinyl material 36, for example, and is affixed to the finger cot by any standard method, such as by stitching. The panel extends to overlay most of the palmar portion overlaying the middle phalanx of a user 37 but does not extend beyond the middle phalanx. The palmar portion overlaying a user's proximal phalanx comprises of a rectangular panel 38. Stamped on the panel is a plurality of PVC dot projections 39 of at least about four hundred micrometers, thus creating a grip enhancing means. Furthermore, each of the projections are shaped in the form of tiny hearts 39. The panel may be composed of any panel forming material aforementioned, such as a latex material 38, and is affixed to the finger cot by any standard method, such as by stitching. The panel extends to overlay most of the palmar portion overlaying the proximal phalanx of a user but does not extend beyond the proximal phalanx area. The embodiment is adapted to fit snugly over a user's finger.

The dorsal portion (or back) can be constructed primarily of the same materials forming the palmar portion, a latex or synthetic latex or may be formed of a second material, depending on user preferences and other considerations aforementioned. Provided along the dorsal portion is a grip enhancing means, such as PVC dots, for example for added grip support in controlling a ball or object. Specifically, the dorsal portion overlaying a user's distal phalanx comprises of a circular panel 41. Formed on the panel is a plurality of PVC dot projections 42 of at least three hundred micrometers. The panel can be composed of any panel forming materials aforementioned, such as a neoprene material 41, and is affixed to the finger cot by any standard method, such as by stitching. The panel extends to overlay most of the distal phalanx area of the dorsal portion. The dorsal portion overlaying a user's middle phalanx comprises of an oval panel 43. Formed on the panel is a plurality of PVC dot projections 44 of at least two hundred micrometers. The panel can be composed of any panel forming material aforementioned, such as a vinyl material 43, for example, and is affixed to the finger cot by any standard method, such as by stitching. The panel extends to overlay most of the dorsal portion overlaying the middle phalanx of a user but does not extend beyond the middle phalanx.

The dorsal portion overlaying a user's proximal phalanx may also comprise of a grip enhancing means, said grip enhancing means may be formed by projections, depressions, coatings aforementioned or by providing a panel over the dorsal portion overlaying a user's proximal phalanx.

The finger cot embodiment may also have an expandable securement opening means 44 at an open end adapted to receive the user's hand. This may comprise of a securement opening means such as but not limited to a strap which mechanically engages a strap 45 capture mechanism to secure the finger cot such as a synthetic hook and loop fastening interface which adheres when pressed together, commonly using VELCRO. In this case the strap could overlay a small slit 47 or opening along the embodiment's dorsal portion to allow the finger cot to enclose a digital segment of a user, such as on a user's forefinger, for example. Alternatively, the opening securement means may comprise of other standard used mechanisms of allowing a user to apply and disengage the finger cot, such as an elastic band material along the open end of the finger cot. The opening securement means may alternatively comprise an elastomeric band fixed around the open ends of the embodiments. Embodiments may also have combinations of both a strap capture mechanism and an elastomeric band. The expandable securement opening means may be formed integral with the finger cot or may be attached to the finger cot by standard methods, such as by sewing. The strap 45 can generally be constructed of the same material forming the finger cot.

A moisture absorbent material 46 may be provided along the dorsal portion of the finger cot, allowing a user to wipe off perspiration commonly on a user's face during active sports play. The moisture absorbent material may be secured anywhere along the dorsal surface or on the securement opening means, such as affixed to the top surface of a strap 46. The moisture absorbent material may be formed of any moisture absorbent material aforementioned, such as, for example, about 1/12 inch terry cloth 46 stitched onto the substantially the entire top surface of a strap.

Additionally, embodiments such as this may be coated with a water repellant substance 48, such as a synthetic resin, for example, especially useful during rainy weather game situations. The water repellant is applied to the entire embodiment.

This embodiment, and all its described features, may of course be adapted to overlay a user's thumb, middle finger, ring finger or pinkie finger.

A second finger cot embodiment is shown as 50, and is adapted to overlay a user's entire distal and middle phalanges, and at least about fifty percent of the proximal phalanx 50. The palmar view 51 of the finger cot is drawn in FIG. 1, and the dorsal view 52 of the same finger cot is drawn in FIG. 2. This embodiment is adapted to overlay the entire distal, middle and proximal phalanges of a user 50, and offers a grip enhancing means to enhance a user's ability of controlling a ball or an object by providing a higher coefficient of friction than what the skin of a user might otherwise provide, preferably a Durometer A Static Coefficient of Friction of at least 1. More preferably, a Durometer A Static Coefficient of Friction of at least 1.5. The circumference of this embodiment is of substantial length to enclose a digital segment of a user.

The palmar portion can be constructed primarily of any of the materials forming the finger cot as aforementioned, for example, a natural or synthetic rubber 50, thus mirroring, in many respects, what wearing a glove would feel like and accomplish. It offers a grip enhancing means, such as, for example, of elongated projections, for added grip support in controlling a ball or object. Specifically, the palmar portion overlaying a user's middle finger comprises of a series of alternating linear 53 and non-linear 54 patterned lines. The linear lines are at least three hundred micrometers in height, and extend along the palmar portion overlaying the user's distal, middle, and proximal phalanges. These linear lines are formed of any material aforementioned, such as, for example of a latex substance. The non-linear lines are at least two hundred micrometers in height, and extend to overlay a user's distal and middle phalange, but do not extend along the palmar portion overlaying a user's proximal phalanx. The linear and non-linear lines may of course, be integrally formed on this and other embodiments, or may alternatively be applied to the embodiments. Shown here, the linear and non-linear lines are integrally formed on the embodiment and are therefore constructed of the same material as the finger cot.

The dorsal portion of the embodiment may be constructed of the same material as the material forming the palmar portion, such as synthetic rubber, or may be comprised of different material depending on user preferences and other considerations aforementioned. The dorsal surface of this embodiment also offers a grip enhancing means, such as, for example, of elongated depressions. Specifically, the dorsal portion overlaying a user's middle finger comprises of a series of alternating linear 55 and non-linear 56 patterned lines. The linear lines are at least three hundred micrometers in height, and extend along the dorsal portion overlaying the user's distal, middle, and proximal phalanges. These linear lines are formed of any material aforementioned, such as, for example of a latex substance. The non-linear lines are at least two hundred micrometers in height, and extend to overlay a user's distal and middle phalange, but do not extend along the dorsal portion overlaying a user's proximal phalanx. The linear and non-linear lines may of course, be integrally formed on this and other embodiments, or may alternatively be applied to the embodiments. Shown here, the linear and non-linear lines are integrally formed on the embodiment and are therefore constructed of the same material as the finger cot.

Shown also is a securement opening means 57 along the open end of the finger cot, and which may comprise of standard used mechanisms of allowing a user to apply and disengage the finger cot, such as an elastomeric band material 57 along the open end of the finger cot. The opening means may alternatively comprise any securement opening means aforementioned. The elastomeric band may be composed of rubber, and may be affixed to the finger cot by any standard methods, such as by stitching. The palmar and dorsal portions are essentially the same size.

Applied to the finger cot is a moisture repellent 59, such as, for example, a synthetic resin, which better adapts the finger cot for use in active outdoor sports activities. The moisture repellant is applied to the entire outer surface of the finger cot by any standard methods, such as by spraying.

This embodiment, and all its described features, may of course be adapted to overlay a user's thumb, forefinger, ring finger or pinkie finger.

A third finger cot embodiment is shown as 70, and is adapted to overlay a user's entire distal and middle phalanges, but does not extend to cover more than fifty percent of a user's proximal phalanx.

The palmar view 71 of the finger cot is drawn in FIG. 1, and the dorsal view 72 of the same finger cot is drawn in FIG. 2. It is adapted to overlay the entire distal, middle and proximal phalanges of a user 70, and offer a grip enhancing means to enhance a user's ability of controlling a ball or an object by providing a higher coefficient of friction than what the skin of a user might otherwise provide, preferably a Durometer A Static Coefficient of Friction of at least 1. More preferably, a Durometer A Static Coefficient of Friction of at least 1.5. The circumference of the embodiment is of substantial length to fit snugly around a digital segment of a user. The palmar portion and the dorsal portion are of essentially the same dimensions in length and width.

The finger cot embodiment may be constructed of any materials aforementioned, such as a polyester and elastic combination 70 for added flexibility and maneuverability. It offers a grip enhancing means, such as, for example, of elongated depressions for added grip support in controlling a ball or object. Specifically, the palmar portion overlaying a user's distal phalanx comprises of a rectangular panel 73. Formed on the panel is a plurality of vertical line depressions 74 of at least two hundred micrometers in depth. The panel can be composed of any panel forming materials aforementioned, such as, for example, a neoprene material 73, and is affixed to the finger cot by any standard method, such as by stitching. The panel extends to overlay most of the distal phalanx area of the palmar portion but does not extend beyond the distal phalanx. The palmar portion overlaying a user's middle phalanx comprises of an oval panel 75. Formed on the panel is a plurality of vertical line depressions 76 of about three hundred micrometers in depth. The panel can be composed of any panel forming materials aforementioned, such as a vinyl material 75, for example, and is affixed to the finger cot by any standard method, such as by stitching. The panel extends to overlay most of the middle phalanx area of the palmar portion but does not extend beyond the middle phalanx. The embodiment is adapted to fit over a user's digital segment.

The dorsal portion of this embodiment may be constructed of the same material as the material forming the palmar portion, such as polyester 72, or may be comprised of different material, depending on user preferences and other considerations aforementioned. The dorsal surface of this embodiment also offers a grip enhancing means, such as, for example circular depressions. Specifically, the dorsal portion overlaying a user's proximal phalanx comprises of a series of depressions in the form of circles 77. These circles are at least about two hundred micrometers in depth, and extend to overlay the user's proximal phalanx. These circles are integrally formed on the dorsal surface and are further coated with a latex substance 78, for example, to provide an even higher coefficient of friction along the dorsal surface. This is especially important for users playing the sport of golf using the conventional interlocking grip method. By providing a grip enhancing means along the dorsal portion of the embodiment a user gives the interlocked forefinger a place to better grip the pinkie finger, which has the pinkie embodiment.

Shown also is an aperture 79 which leaves exposed a user's middle interphalangeal joint. The aperture allows a user to more easily flex and maneuver his or her finger during active sports play.

Shown also are microrecesses 80 along the dorsal surface overlaying a user's middle phalanx, for enhanced moisture management capabilities. These microrecesses are generally about 0.120 millimeters in diameter.

Shown also is a securement opening means 81 along the open end of the finger cot, and which may comprise of standard used mechanisms of allowing a user to apply and disengage the finger cot, such as an elastomeric band material along the open end of the finger cot. The opening means may alternatively comprise any securement opening means aforementioned. The elastomeric band may be composed of rubber, and may be affixed to the finger cot by any standard methods, such as by stitching. The palmar and dorsal portions are essentially the same size.

Additionally, embodiments such as this may be coated with a water repellant substance 82, such as a synthetic resin, for example, especially useful during harsh weather situations. The water repellant is applied to the entire embodiment.

This embodiment, and all its described features, may of course be adapted to overlay a user's thumb, forefinger, middle finger or pinkie finger.

Another example of a finger cot embodiment is shown as 90, and is adapted to overlay a user's entire distal, middle and proximal phalanges. It is made of nylon, and offers yet a slightly different grip enhancing means. The embodiment is adapted to fit snugly over a user's finger.

The palmar view 91 of the finger cot is drawn in FIG. 1, and the dorsal view 92 of the same finger cot is drawn in FIG. 2. It is adapted to overlay the entire distal, middle and proximal phalanges of a user and offer a grip enhancing means to enhance a user's ability of controlling a ball or an object by providing a higher coefficient of friction than what the skin of a user might otherwise provide, preferably a Durometer A Static Coefficient of Friction of at least 1. More preferably, a Durometer A Static Coefficient of Friction of at least 1.5. The circumference is wide enough to fit snug on a digital segment of a user.

The palmar portion of the embodiment can be constructed primarily of, for example, nylon 91 or rayon. It offers a grip enhancing means, such as, for example, of elongated depressions, for added grip support in controlling a ball or object. Specifically, substantially all of the palmar portion overlaying a user's pinkie finger comprises of a series of non-linear patterned lines in the form of grooves 93. The non-linear lines are at least two hundred micrometers in depth, are integrally formed on the finger cot, and extend to overlay the user's distal, middle, and proximal phalanges. Shown here, the non-linear lines are molded onto the finger cot. The grooves are further coated with latex 94, to create an even higher coefficient of friction along the finger cot outer surface.

The dorsal portion of the embodiment may be constructed of the same material as the material forming the palmar portion, such as nylon 92, or may be comprised of different material, depending on user preferences and other considerations aforementioned. The dorsal surface of this embodiment also offers a grip enhancing means, such as, for example, of elongated depressions. Specifically, substantially all of the dorsal portion overlaying a user's proximal phalanx comprises of a series of non-linear patterned lines in the form of grooves 95. These non-linear lines are at least two hundred micrometers in depth, and extend to overlay the user's proximal phalanx. These non-linear lines are integrally formed on the dorsal surface and are further coated with a latex substance 94, for example, to provide an even higher coefficient of friction along the dorsal surface. This is especially important for user's playing the sport of golf using the conventional interlocking grip method. By providing a grip enhancing means along the embodiment's dorsal portion, a user give the interlocked forefinger a place to better grip the pinkie finger, which has the pinkie embodiment. Shown here, the non-linear lines are molded onto the finger cot.

Finger cot embodiments may also have an expandable securement opening means 96 at an open end adapted to receive a user's digital segment. This may comprise of a securement opening means such as but not limited to a strap which mechanically engages a strap capture mechanism 96 to secure the finger cot such as a synthetic hook and loop fastening interface which adheres when pressed together, commonly using VELCRO. In this case the strap could overlay a small slit or opening 97 along the embodiment's dorsal portion to allow the finger cot to widen when a user places a digital segment of a user, such as on a user's pinkie finger, for example. The dorsal portion is essentially the same size as the palmar portion.

The strap can generally be constructed of any suitable standard materials, such as a flexible plastic, and may be affixed to the open end of the finger cot by any standard methods such as by stitching.

Additionally, embodiments such as this may be coated with a moisture repellant substance 98, such as a synthetic resin, for example. The moisture repellant is applied to the entire embodiment.

A moisture absorbent material may be provided along the dorsal portion of the finger cot, allowing a user to wipe off perspiration, a common occurrence during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, about 1/16 inch terry cloth or absorbent foam stitched onto the substantially the entire top surface of a strap.

This embodiment, and all its described features, may of course be adapted to overlay a user's thumb, forefinger, middle finger, or ring finger, thus simply only altering the finger general structure configuration.

These finger cot embodiments, individually or in combination, offer the ability in one respect, to essentially separate a conventional glove into its different components and then selectively choose which components to wear. This can be especially important for those individuals who need to retain heightened sensitivities in part of the hand, but need grip support in another part of the same hand. Using gloves instead of finger embodiments for these individuals would also be an unnecessary waste of materials.

Figure 3:
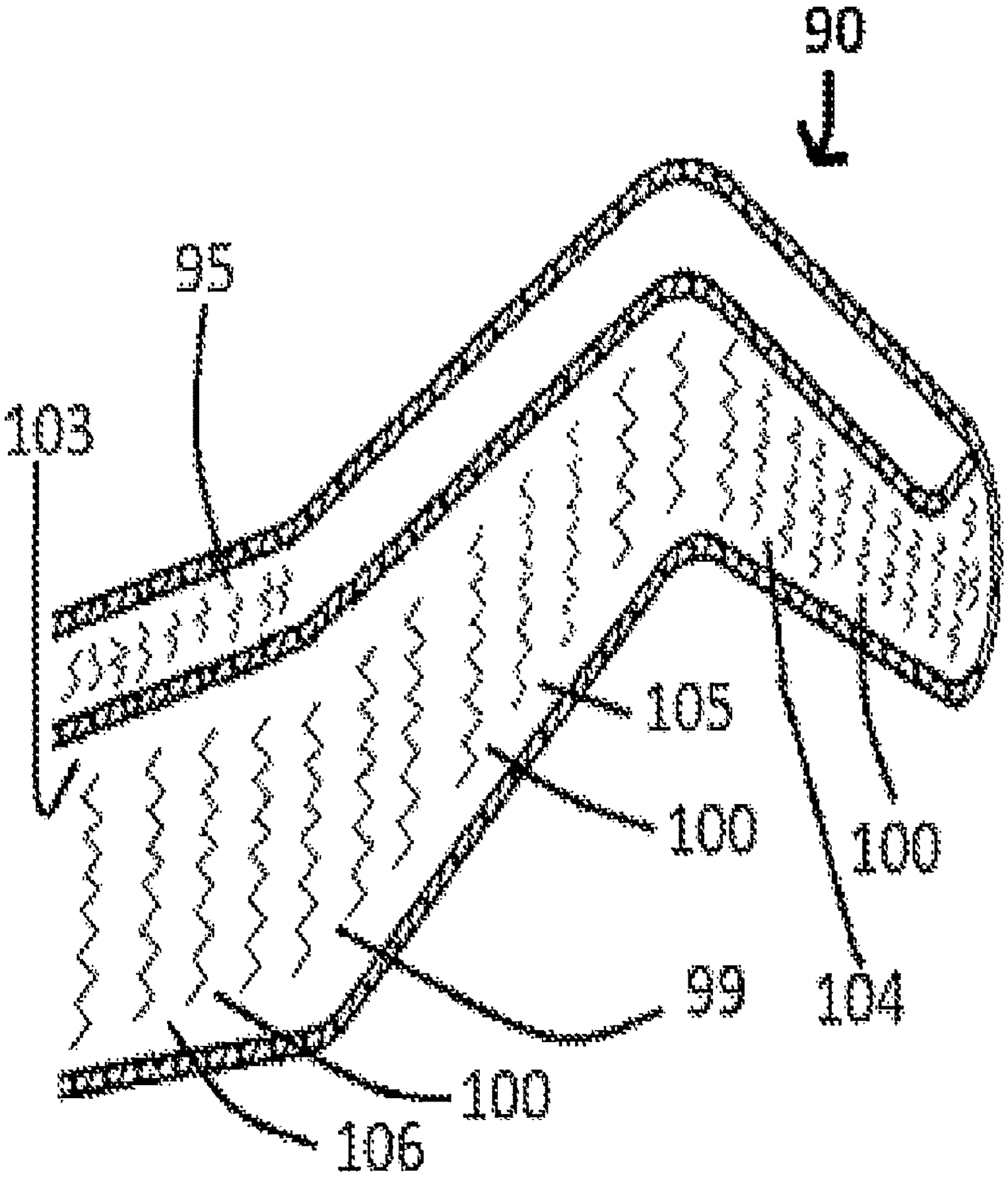
FIG. 3 and FIG. 4 are drawings showing both sides of a finger cot embodiment.
Figure 4:
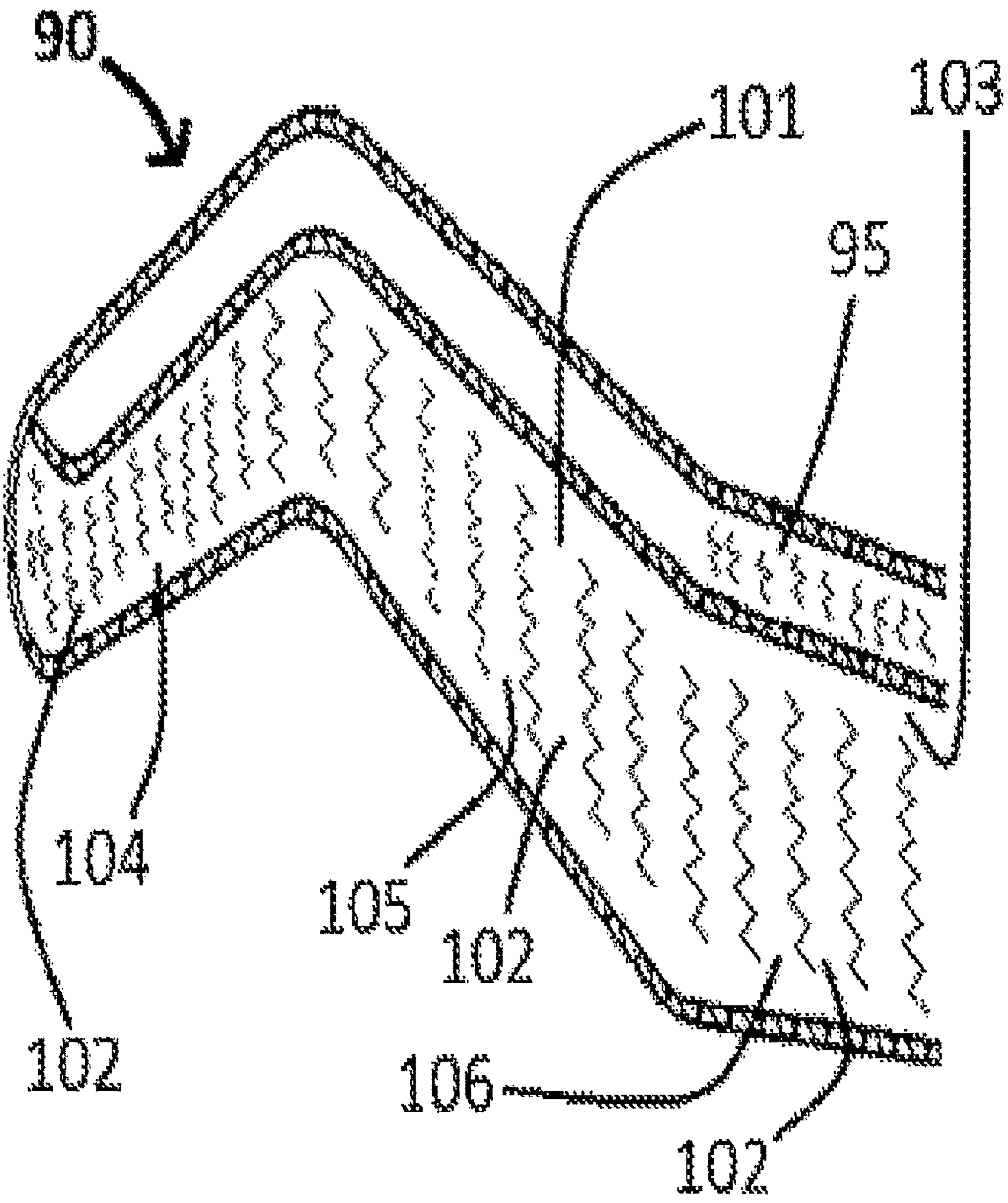

FIG. 3 and FIG. 4 show two opposing sides of a finger cot embodiment, as shown in FIG. 1, over a user's pinkie finger 90. The first side 99, in this embodiment, is adjacent to a user's forefinger, and is made of nylon. The first side offers a grip enhancing means, such as, for example, of elongated depressions, for added grip support in coordinating both hands while swinging a golf club using the conventional overlapping grip method. Specifically, substantially all of the first side overlaying a user's entire distal 104, middle 105 and proximal 106 phalanges comprises of a series of non-linear patterned lines in the form of grooves 100. The non-linear lines are at least about two hundred micrometers in depth, and extend throughout the first side 99 of the finger cot. These non-linear lines are integrally formed on this embodiment and would thus be constructed of the same material forming the finger cot. The non-linear lines can be formed by any standard methods, such as stamping or molding the grooves onto the finger cot. The embodiment is adapted to fit snugly over a user's digital segment, such as a pinkie finger.

The second side 101, in this embodiment and is made of nylon. The second side offers a grip enhancing means, such as, for example, of elongated depressions, for added grip support in coordinating both hands while swinging a golf club using the conventional overlapping grip method. Specifically, substantially all of the second side overlaying a user's entire distal 104, middle 105 and proximal 106 phalanges comprises of a series of non-linear patterned lines in the form of grooves 102. The non-linear lines are at least about two hundred micrometers in depth, and extend throughout the second side of the finger cot. These non-linear lines are integrally formed on this embodiment and would thus be constructed of the same material forming the finger cot. The non-linear lines can be formed by any standard methods, such as stamping or molding the grooves onto the finger cot.

Also shown is a liner 103. The lining material may be comprised of standard lining materials, such as a smooth, flexible knitted fabric. The liner may also comprise of flexible and elastomeric material such as spandex or LYCRA. Other possible materials include a knit of polyester or simply the same material forming the tubular member. A soft cellular plastic could also be preferred. Additionally, the liner may provide added features to offer warmth and comfort such as by comprising of a fleece material 103, for example, especially useful when competing in rather harsh environments.

Figure 5:
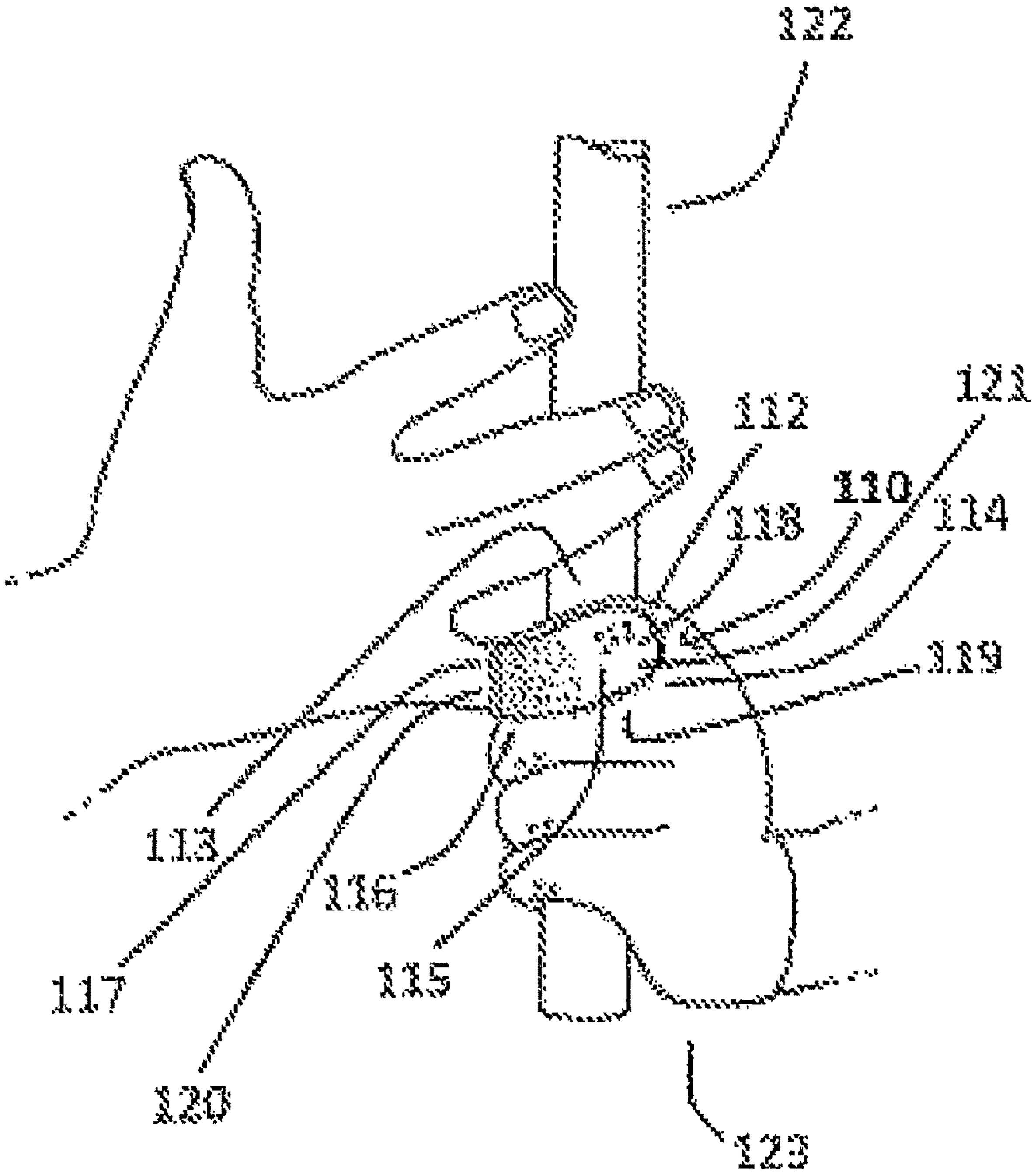
FIG. 5 is a drawing of someone using a finger cot embodiment while gripping a golf club using the conventional overlapping grip method.

FIG. 5 illustrates how finger cot embodiments, including the embodiment described in 90, will find use and success in the sport of Golf. Shown for example, is another finger cot embodiment 110, and is adapted to overlay a user's entire distal phalanx and middle phalanx, and at least seventy percent of the proximal phalanx.

This finger cot embodiment has a first end and a second end, the first end is closed and the second end is open and adapted to allow enclose a substantial portion of a user's digital segment, such as a pinkie finger. The palmar and dorsal portions are essentially the same size.

The finger cot embodiment may be constructed any materials aforementioned, such as a polyurethane mesh combination 110 for added flexibility and maneuverability. It offers a grip enhancing means, such as, for example, of projections for added grip support in controlling a ball or object. Specifically, a grip enhancing means in the form of bead projections 112 overlaying a user's distal and middle phalanges is provided along the palmar as well as the first side 113 and second side 114 of the finger cot surface. The bead projections may be integrally formed and thus formed of the same materials forming the finger cot, or may be formed of a different material, such as PVC, and applied to the finger cot surface by any standard methods, such as by molding. The bead projections on the palmar surface are generally of the same heights as the bead projections on the first side and the second side of the finger cot, generally at least about two hundred micrometers in height.

Provided along the dorsal surface are microrecesess 115, for moisture management purposes. The microrecesses may be disposed throughout the finger cot surface area, preferably along the dorsal surface area overlaying a user's distal phalanx 115.

A moisture absorbent material 116 may be provided along the dorsal portion of the finger cot, allowing a user to wipe off perspiration commonly on a user's face during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, about ⅛ inch terry cloth 116 stitched onto the substantially the entire dorsal surface overlaying a user's proximal and middle phalanges 116.

The dorsal portion 118 of this embodiment may be constructed of the same material as the material forming the palmar portion 119, such as polyester, or may be comprised of different material, depending on user preferences and other considerations aforementioned. For example, the finger cot embodiment is formed substantially of one material molded generally of one material, thus no need to affix a palmar portion with a dorsal portion.

Shown also is a securement opening means 117 along the open end of the finger cot, and which may comprise of standard used mechanisms of allowing a user to apply and disengage the finger cot, such as an elastomeric band material 120 along the open end of the finger cot. The securement opening means may alternatively comprise of any securement opening means aforementioned. The elastomeric band may be composed of rubber, and may be affixed to the finger cot by any standard methods, such as by stitching.

Additionally, embodiments such as this may be coated with a moisture repellant substance 121, such as a synthetic resin, for example, especially useful during game play. The moisture (or water) repellant is applied to the entire embodiment.

This embodiment, and all its described features, may of course be adapted to overlay a user's thumb, forefinger, middle finger or ring finger.

Drawn is a golfer using a finger cot embodiment while gripping a golf club 122. The user is gripping a golf club using the traditional overlapping grip method. Furthermore, the user has a conventional glove 123 on his weak hand and has the finger cot embodiment on his strong hand's pinkie finger. As can be seen, the overlapping pinkie finger has substantially increased gripping capabilities. During the downswing of the golf club, the user can now better grip the gloved weak hand with the grip enhanced pinkie finger, using the finger cot embodiment on the strong hand by using the grip enhancing means along the embodiment's palmar portion as well as on the first and second side portions. The result will be increased swing coordination and control between the user's two hands.

Figure 6:
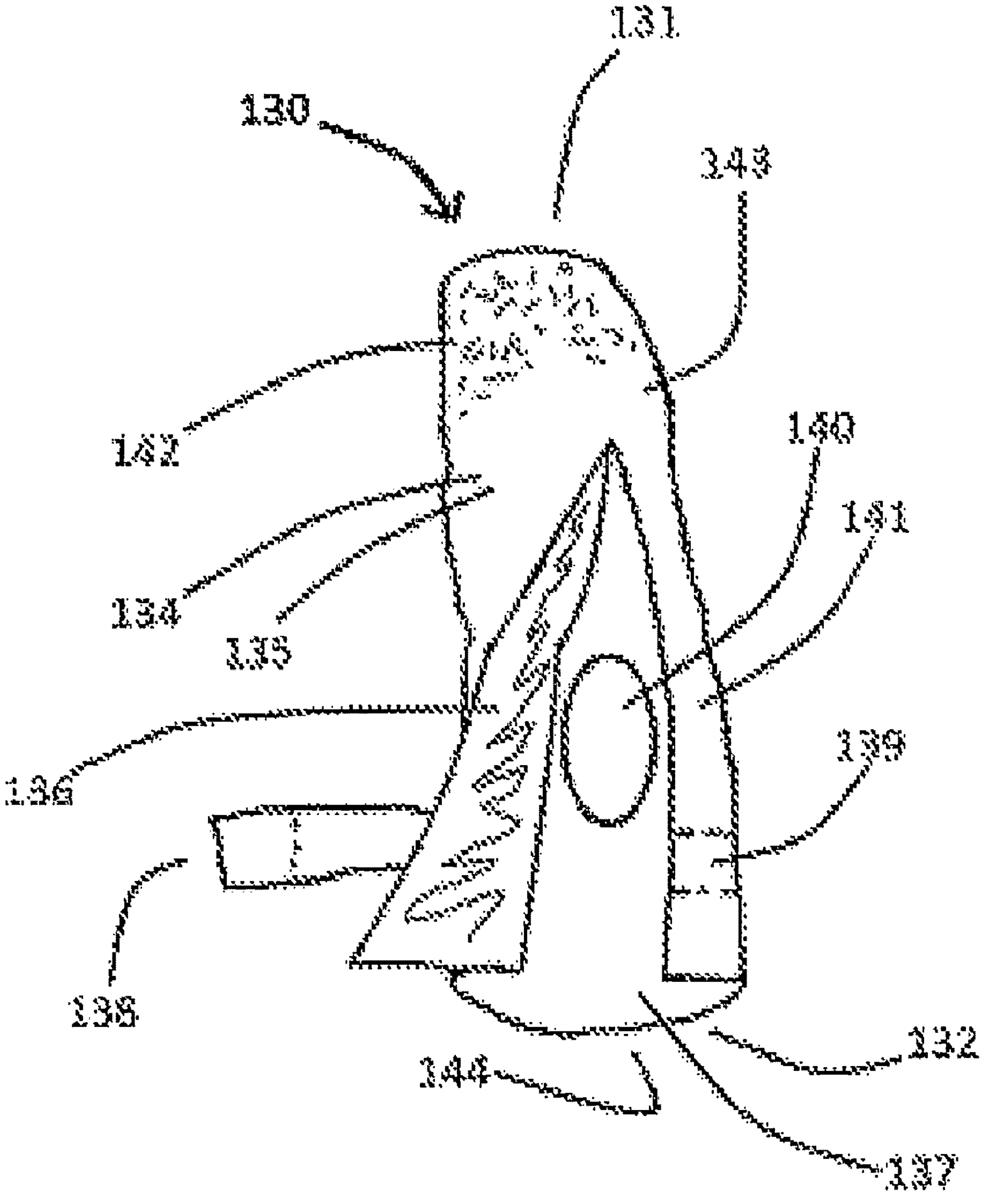
FIG. 6 is drawing showing another finger cot embodiment, with an aperture on the palmar surface, and a shock absorbing member on the dorsal side of the embodiment.
Figure 7:
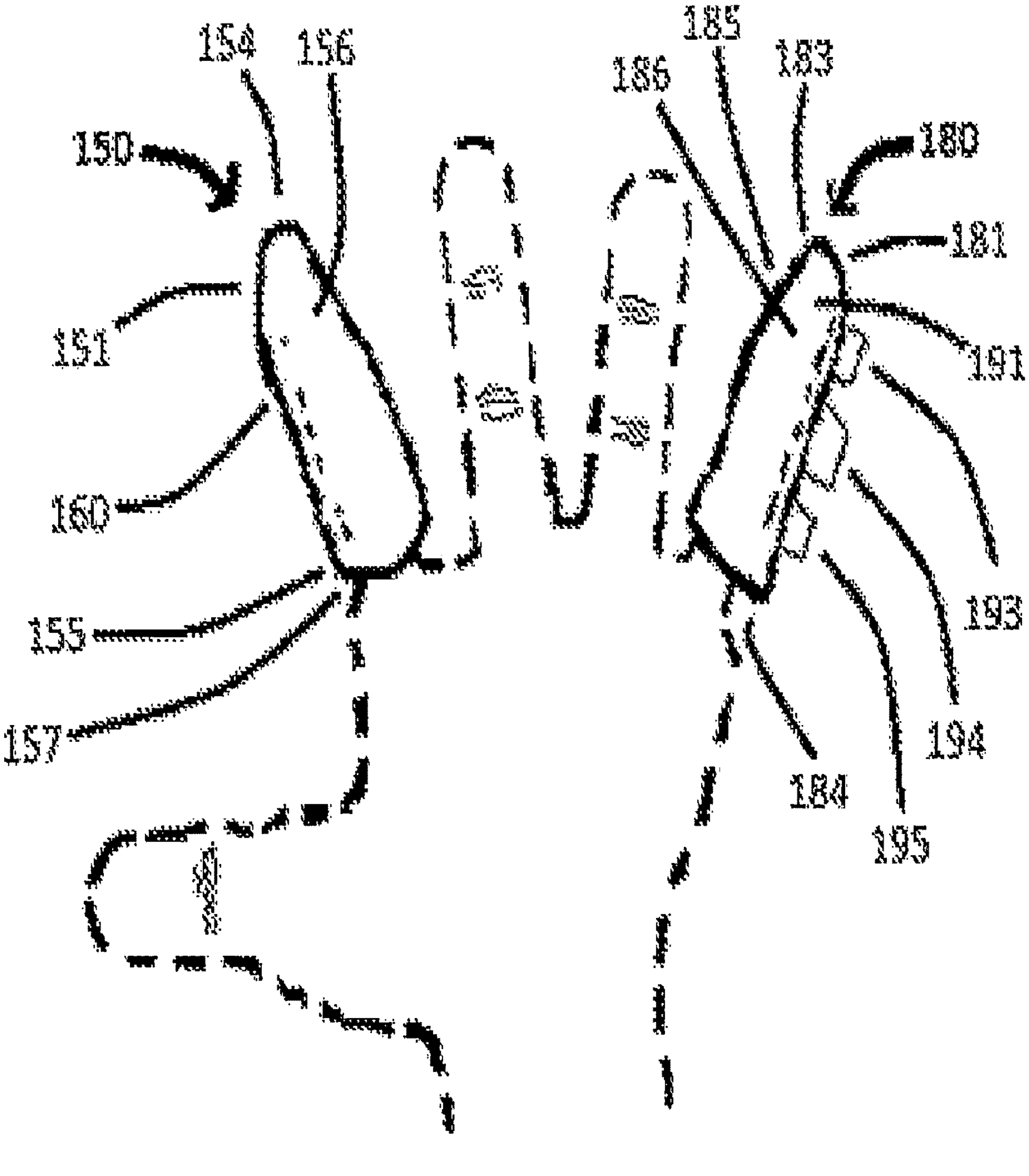
FIG. 7 is drawing of two finger cot embodiments on the left hand of a user, showing the palmar surfaces.
Figure 8:
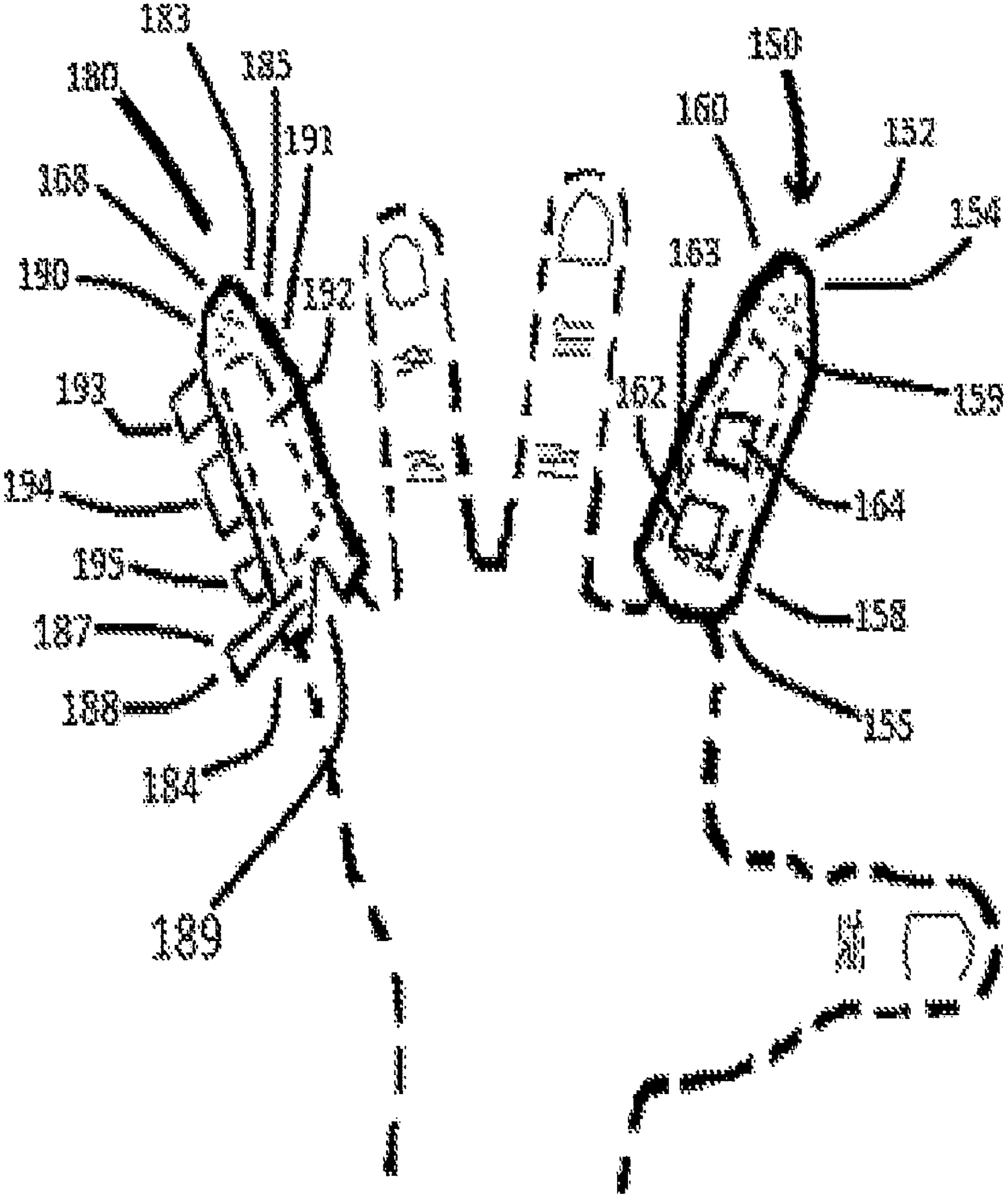
FIG. 8 is a drawing showing the dorsal surface of the embodiments in FIG. 6
Figure 9:
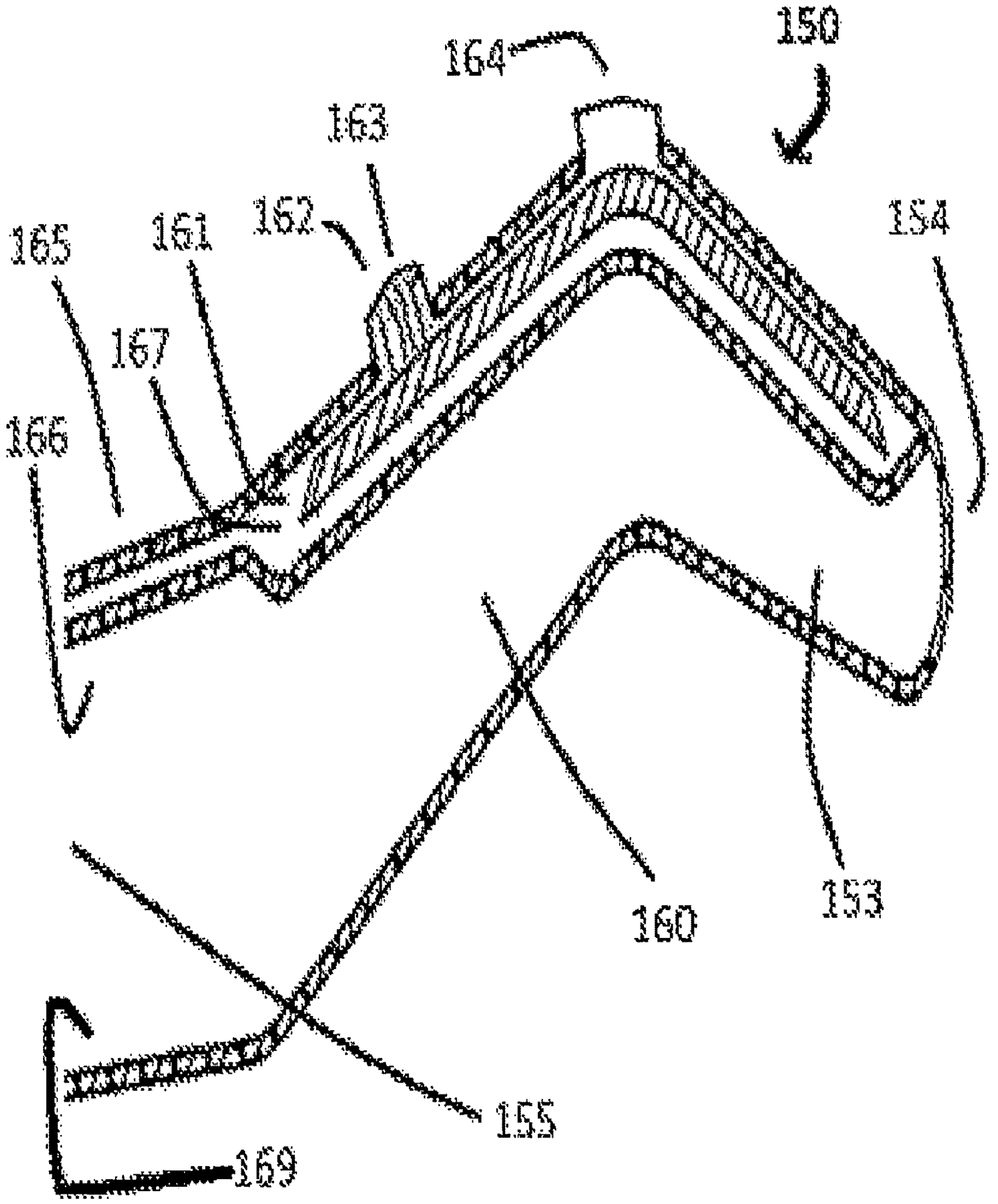
FIG. 9 is a side view drawing of a finger cot embodiment showing a liner and shock absorbing members.
Figure 10:
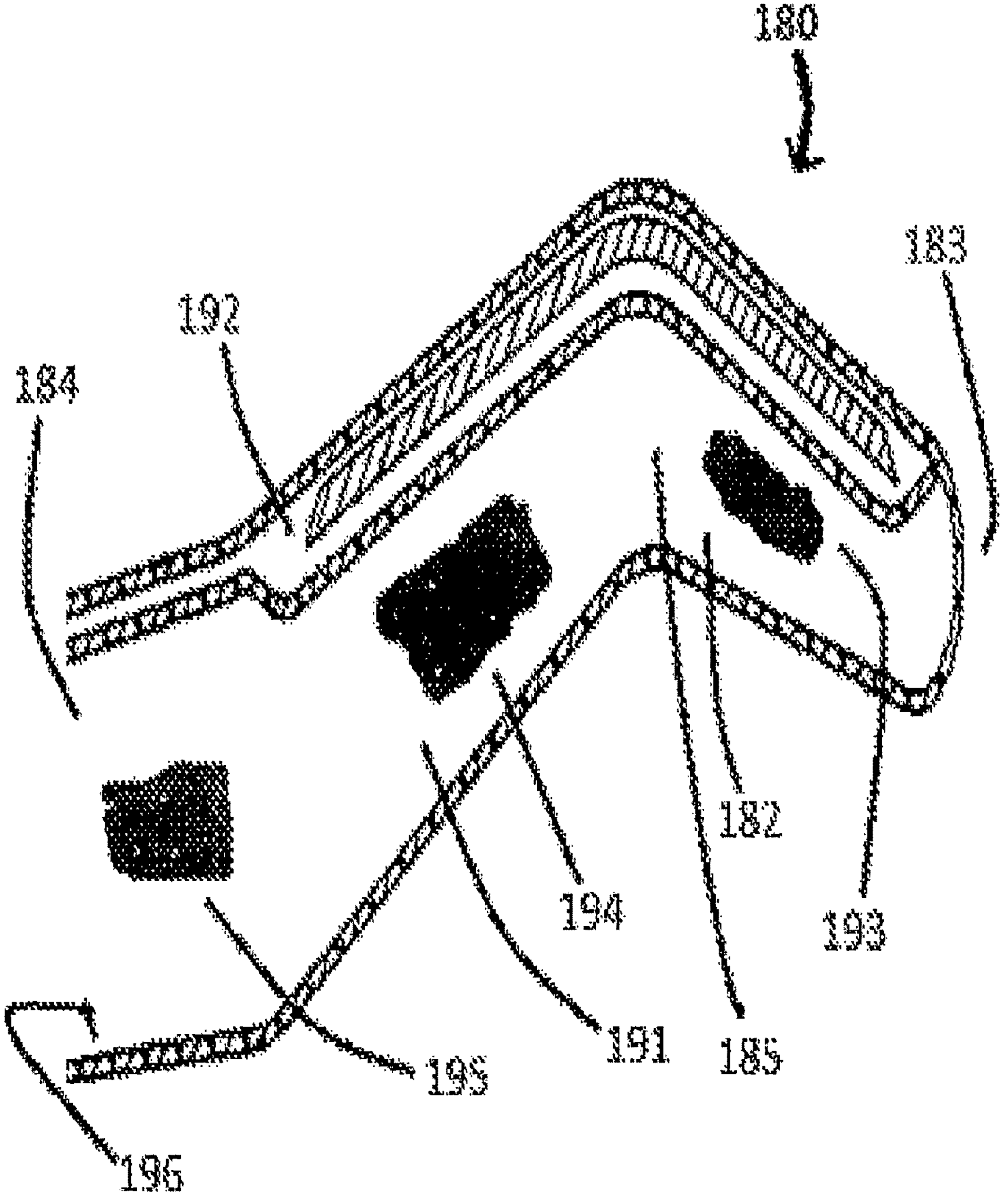
FIG. 10 is another side view drawing of a finger cot embodiment showing a liner and a shock absorbing member.

FIG. 6 of the present invention shows another finger cot embodiment 130 similar to those illustrated in FIG. 1.

This finger cot embodiment has a first end 131 and a second end 132, the first end is closed and the second end is open and adapted to enclose at least a substantial portion of a user's digital segment. More specifically, this embodiment is adapted to overlay a user's entire distal middle phalanges and at least seventy percent of the proximal phalanx 130, of say a thumb digital segment, for example.

The dorsal portion 134 of this embodiment may be constructed of the same material as the material forming the palmar portion, such as synthetic leather 135, or may be comprised of different material, depending on user preferences and other considerations aforementioned. For example, this finger cot embodiment is formed substantially of one material and molded generally of one material, thus no need to affix a palmar portion with a dorsal portion.

This embodiment shows a shock absorbing member 136, which is composed of material which is compressible and bendable to protect a user from injury or to protect an injury. The shock absorbing member of the embodiment may be formed of a thin layer of foam 136, for example, of at least about six hundred micrometers. More preferably, the layer of foam is at least about one millimeter thick. The shock absorbing member may generally be affixed to the finger cot dorsal surface or may be integrally formed within the finger cot structure. The shock absorbing member may be provided throughout its dorsal portion 134, on only part of its dorsal portion, or along any of the embodiment's two sides. The shock absorbing member may then be affixed to the finger cot by any standard means, such as by adhesion.

Embodiments may also comprise of slit 137 beginning at one side of the open end and extending a part of the length of the finger cot. The embodiment also provides an expandable securement opening means 138 along the finger cot's open end. The slit makes it easier for, say a golfer to quickly remove the embodiment, as he's walking towards a putting green. The expandable securement opening means allows a user to fasten and/or tighten the embodiment. This particular embodiment shows a strap 138 with VELCRO, that attaches to the other side of the opening that possesses the VELCRO receiving end 139. Other modifications could offer a small brace such that the strap could wrap around before reattaching to the VELCRO receiver. The expandable securement opening means may be formed of the same material forming the finger cot or may be any suitable material, such as a flexible plastic 138, and affixed to the open end of the embodiment by any standard method such as by stitching. The VELCRO may also be affixed by any standard methods, such as by adhesion.

Shown is also an aperture 140 along the palmar surface 144 adapted to expose a user's phalanx, such as a user's middle phalanx area. The aperture resides along the palmar portion and does not extend to leave exposed more than one phalanx of a user's finger.

Additionally, embodiments such as this may be coated with a water repellant substance 141, such as a synthetic resin, for example, especially useful during harsh game situations. The water repellant is applied to the entire embodiment.

A moisture absorbent material 142 may be provided along the dorsal portion of the finger cot, allowing a user to wipe off perspiration commonly on a user's face during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, at least about 1/16 inch terry cloth 142 stitched onto the substantially the finger cot's entire dorsal surface overlaying a user's proximal phalanx 143.

Referring now to FIG. 7, FIG. 8, FIG. 9 and FIG. 10, shown are palmar views, dorsal views and cross-sectional side views of two finger cot embodiments, illustrated on a user's left hand. These embodiments have a circumference of substantial size to fit tightly around select areas of a finger, but do not extend to overlay a second finger.

The first finger cot embodiment is shown and designated as 150. The palmar view 151 of the finger cot is drawn in FIG. 7, the dorsal view 152 of the same finger cot is drawn in FIG. 8, and the side view 153 of the same finger cot is drawn in FIG. 9. This finger cot embodiment has a first end 154 and a second end 155, the first end is closed and the second end is open and adapted to receive a user's digital segment. More specifically, for example, this embodiment may be adapted to overlay the entire distal, middle and proximal phalanges of a user's forefinger. The palmar and dorsal portions are essentially the same size.

This embodiment, and all its described features, may of course be adapted to overlay a user's thumb, middle finger, ring finger or pinkie finger.

The palmar portion (or front) can be constructed primarily of any flexible, resilient material aforementioned, for example, a leather or synthetic leather. It offers a grip enhancing means in the form of a coating or compound, for added grip support in controlling a ball or object. Specifically, the palmar portion overlaying a user's distal phalanx comprises of a latex coating 156.

The dorsal portion (or back) of the finger cot can be constructed primarily of the same materials forming the palmar portion, a leather or synthetic leather for example or may be formed of a second material, depending on user preferences and other considerations aforementioned, such as nylon.

This finger cot embodiment may also have an expandable securement opening means 157 at the open end adapted to receive the user's digital segment. This may comprise of a securement opening means such as but not limited to a strap which mechanically engages a strap capture mechanism to secure the finger cot such as a synthetic hook and loop fastening interface which adheres when pressed together, commonly using VELCRO. Alternatively, the securement opening means may comprise of other standard used mechanisms of allowing a user to apply and disengage the finger cot, such as an elastic band material 158 along the open end of the finger cot, such as an elastomeric band fixed around the open end of the embodiment. Embodiments may also have combinations of both a strap capture mechanism and an elastomeric band. The expandable securement opening means may be formed integral with the finger cot or may be attached to the finger cot by standard methods, such as by sewing.

A moisture absorbent material 159 may be provided along the dorsal portion of the finger cot, allowing a user to wipe off perspiration commonly on a user's face during active sports play. The moisture absorbent material may be secured anywhere along the dorsal surface or on the securement opening means. The moisture absorbent material may be formed of any moisture absorbent material aforementioned, such as, for example, about 1/12 inch terry cloth or foam stitched onto the dorsal surface area overlaying a user's distal phalanx.

Additionally, embodiments such as this may be coated with a water repellant substance 160, such as a synthetic resin, for example, especially useful during harsher weather game situations. The water repellant is applied to the entire embodiment.

Embodiments may also preferably comprise of a shock-absorbing member along any portion of the dorsal surface.

This embodiment has a first shock-absorbing member along substantially all of the dorsal surface overlaying the user's forefinger. This shock-absorbing member is in the pattern of a rectangle 161, may be formed of any shock absorbing materials aforementioned such as an elongated cloth pad 161, and may be configured as a one pad segment, thus defining the boundaries of the first shock absorbing member by the length and width of the finger cot's dorsal surface.

This embodiment has a second layer shock-absorbing member along the dorsal portion overlaying a user's proximal phalanx, extending out as a protrusion 162 along the proximal phalanx area. This second shock-absorbing member may be in the pattern of a square 162, and may be configured as a one pad segment. Other embodiments may prefer to offer additional separate padding segments, for example, with a second pad overlaying only the middle phalanx of a user, and a third pad overlaying only the distal phalanx of a user.

The length of the second layer shock-absorbing member is further restricted to the length of a protrusion 163 along the proximal phalanx on the finger cot and, as mentioned, the dorsal surface area of the finger cot—allowing for the shock-absorbing member to extend circumferentially along the sides of the finger cot but not extending onto the palmar surface of the finger cot, therefore not extending over about one hundred and eighty degrees of the digital segment. Users may of course prefer any combination of the aforementioned.

The shock absorbing members provide the user with added protection from the abrasion such as from hitting said fingers on the ground or while the quarterback rushes with the football.

Additionally, the embodiment is configured such that a second protrusion 164 exists along the dorsal surface overlaying a user's proximal interphalangeal joint. This protrusion is does not contain a second shock-absorbing member thus providing the user with added flexibility capabilities along the interphalangeal joint, especially beneficial if the dorsal segment is generally constructed with a more durable material, such as a leather latex combination finger cot embodiment.

The shock-absorbing members may comprise any type of cloth fabric, like a cushion, or foam, such as an open cell foam. The shock-absorbing member need not be very thick, say beginning from about six hundred micrometers or so, to two inches or more. The thickness of pads for example may vary on several factors, of course, such as degree of preferred protection (e.g., the more a quarterback likes to rush with the football, the thicker padding he may desire) as well as the location of the pads (e.g., padding on only the side of the finger cot where many quarterback finger injuries occur). Each shock-absorbing member may comprise of one foam pad or a plurality of small pads to maximize flexibility.

Multiple layered shock-absorbing members may also be offered. The second (or multiple) layer may preferably be of the same material but also may be thicker or more resilient to better protrude.

The shock-absorbing members may be stitched on or may be integral to the finger cot. This can be done by standard methods. The illustration shows the shock-absorbing member integrally formed on the finger cot. For example, the dorsal segment of the finger cot comprises preferably a flexible, integrally molded member which has a tougher outer protective membrane 165 and a smoother hand-contacting inner membrane 166, such as a liner membrane 166 and being connected together around the peripheral edge of the member. The inner membrane is generally flat and outer membrane has a plurality of discreet shock-absorbing protective protrusions.

For example, the shock-absorbing member may comprise a thick layer of resilient plastic foam material, such as ¾ inch polyethylene foam sheet 167, which is interposed between outer membrane 165 and inner membrane 166 to provide a composite laminated sheet which is then molded. The outer membrane is of a suitable plastic material such as vinyl sheet material with a stretch nylon backing. The inner membrane is preferably of double knit polyester or other suitable textile material to minimize abrasion on a user's finger. The composite laminate sheet can then be molded to form the spacing between protrusions, by pressing outer membrane toward inner membrane. The dimensions of the compartments would be of sufficient manner to house the pads.

As mentioned, the shock-absorbing members may alternatively be affixed to the dorsal surface of the finger cot. Methods have previously been discussed such as, for example, encasing the shock-absorbing members of this embodiment with the same material forming the finger cot, then attaching the casings to the dorsal surface such as along the dorsal surface overlaying a user's proximal phalanx, by any standard methods such as by stitching.

Embodiments may also comprise of a liner 169 whereby the shock-absorbing member lies between the dorsal portion and the liner of the dorsal segment. Preferably, the liner is fixed to the dorsal segment interior using methods known in the art, such as stitching to fix the shock-absorbing members to the tubular member.

A second finger cot embodiment is shown and designated as 180. The palmar view 181 of the finger cot is drawn in FIG. 7, the dorsal view 168 of the same finger cot is drawn in FIG. 8, and the side view 182 of the same finger cot is drawn in FIG. 10. This embodiment has a first end 183 and a second end 184, the first end is closed and the second end is open and adapted to receive a user's digital segment. More specifically, for example, this embodiment may be adapted to overlay the entire distal, middle and proximal phalanges of a user's pinkie finger. The palmar and dorsal portions are essentially the same size.

This embodiment, and all its described features, may of course be adapted to overlay a user's thumb, forefinger, middle finger, or ring finger.

The palmar portion (or front) can be constructed primarily of any flexible, resilient material aforementioned, for example, a leather or synthetic leather 185. It offers a grip enhancing means in the form of a coating or compound, for added grip support in controlling a ball or object. Specifically, the palmar portion overlaying a user's distal phalanx comprises of a latex coating 186.

The dorsal portion (or back) of the finger cot can be constructed primarily of the same materials forming the palmar portion, a leather or synthetic leather for example or may be formed of a second material, depending on user preferences and other considerations aforementioned, such as nylon.

The finger cot embodiment may also have an expandable securement opening means 187 at the open end adapted to receive the user's digital segment, such as a user's pinkie finger. This may comprise of a securement opening means such as but not limited to a strap which mechanically engages a strap capture mechanism to secure the finger cot such as a synthetic hook and loop fastening interface 188 which adheres when pressed together, commonly using VELCRO. In this case the strap could overlay a small slit 189 or opening along the embodiment's dorsal portion to allow the finger cot to widen when a user places a digital segment of a user, such as on a user's pinkie finger, for example. Alternatively, the securement opening means may comprise of other standard used mechanisms of allowing a user to apply and disengage the finger cot, such as an elastic band material along the open end of the finger cot.

The expandable securement opening means may be formed integral with the finger cot or may be attached to the finger cot by standard methods, such as by sewing. If desired, the expandable opening means may comprise a strap as part of the securement opening means at the open end of the finger cot body for fastening the tubular member body secure about a user's finger. The strap may have two pads of cohesive-adhesive material for releasably securing the strap 188, for example. The strap as well as the open end may be sewn onto the finger cot. The securement opening means may be unitary with the tubular member body and may include VELCRO fasteners, buttons, and the like or other suitable closure means thereon.

The strap can generally be constructed of the same material forming the finger cot or of any standard materials, such as a flexible plastic, rubber, or SPANDEX material.

A moisture absorbent material 190 may be provided along the dorsal portion of the finger cot, allowing a user to wipe off perspiration commonly on a user's face during active sports play. The moisture absorbent material may be secured anywhere along the dorsal surface or on the securement opening means, such as affixed to the dorsal surface area overlaying a user's distal phalanx. The moisture absorbent material may be formed of any moisture absorbent material aforementioned, such as, for example, about 1/12 inch terry cloth stitched onto the dorsal surface of the embodiment 190.

Additionally, embodiments such as this may be coated with a moisture repellant substance 191, such as a synthetic resin, for example, especially useful during harsher game day situations. The moisture repellant is applied to the entire embodiment.

This embodiment further provides a first shock-absorbing member along substantially all of the dorsal surface overlaying the user's distal phalanx and at least seventy percent of a user's middle phalanx. The first shock-absorbing member overlaying the dorsal portion may be in the pattern of a rectangle 192 for example, and may be configured as a one pad segment. The length of the shock-absorbing member is further restricted to the length of the finger cot's dorsal portion—allowing for the shock-absorbing member to extend circumferentially along the sides of the finger cot but generally not extending onto the palmar surface of the finger cot.

This embodiment offer a second shock absorbing member 193 along is side of the finger cot overlaying a user's distal phalanx but does not extend to overlay a second phalanx, in the form of a uniform foam pad. This embodiment offer a third shock absorbing member 194 along is side of the finger cot overlaying a user's middle phalanx but does not extend to overlay a second phalanx, in the form of a uniform foam pad. This embodiment offer a fourth shock absorbing member 195 along is side of the finger cot overlaying a user's proximal phalanx but does not extend to overlay a second phalanx, in the form of a uniform foam pad By not covering any of a user's finger joints, for example, you may maintain flexibility and motion in the pinkie finger.

As mentioned, the shock-absorbing member may be affixed to the tubular member by any standard methods of attachment, such as by stitching or adhesion. For example, it can be in the form of pouches or attachments to the tubular member, such as on the side of the finger cot and then bonding these pouches to the back of the tubular member, using heat sealing or other methods.

As illustrated, this shock-absorbing member along the dorsal portion is integral with the material that form the tubular member, and may be applied to select areas of the tubular member by standard methods and forms of attachment methods such as, for example, by the dorsal portion comprising of a vinyl sheet material with a stretch nylon backing and the liner 196 made of a knit of polyester. The liner is positioned along the inner surface of the dorsal portion of the tubular member whereby the padded layer or layers would be inserted and then sealed. The cushions may also be secured to the tubular member by conventional stitching.

The liner can be interposed between the shock-absorbing member and the interior of the tubular member, and separates the shock-absorbing member from the user's digital segment, such as disclosed above, allowing easy insertion of the user's finger. Preferably, the liner is fixed to the dorsal segment interior using methods known in the art, such as stitching, to affix the shock-absorbing member to the tubular member. The padding can be interposed between the dorsal portion and the liner. The liner secures the shock-absorbing member between the user's digital segment and the dorsal segment. Of course, other methods of attachment that are known in the art may be used, such as by chemical bonding.

The shock-absorbing member will give the user added protection from the abrasion from hitting a user's fingers against the helmet of an opponent, for example. The shock-absorbing member of the present invention offer the unique ability of being able to protect an injury while maintaining grip capabilities in select areas by offering padded layer or layers, a significant and substantial advancement to prior art, such as bandages and BAND-AID, thus providing a solution to a long-felt need of being able to protect a quarterback's throwing hand.

The paddings can also be made of a thicker neoprene material, of at least ½ inch, or of any other shock absorbing materials aforementioned.

Figure 11:
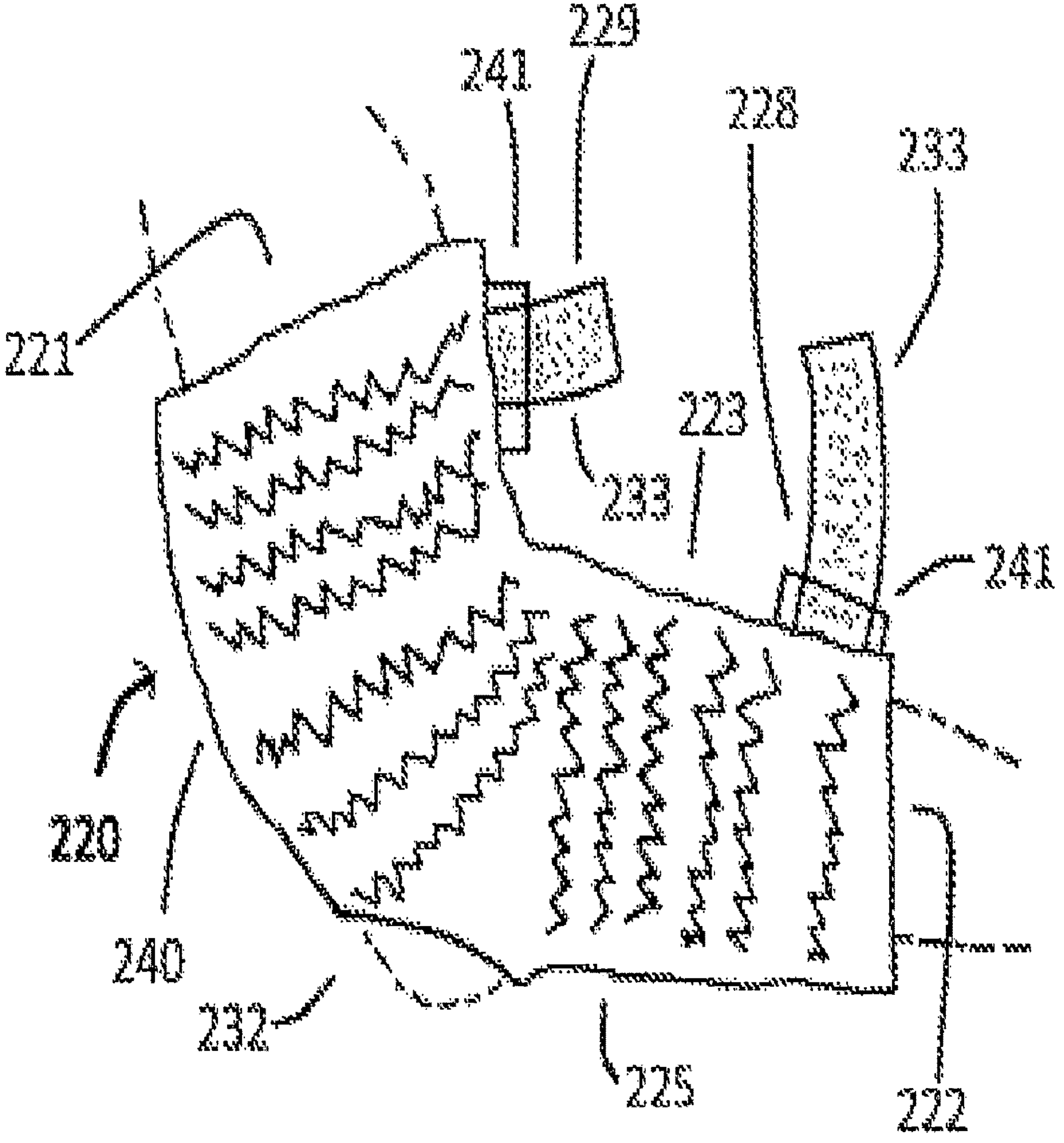
FIG. 11 is a drawing showing the palmar side of a sports sleeve embodiment on the arm of a user.
Figure 12:
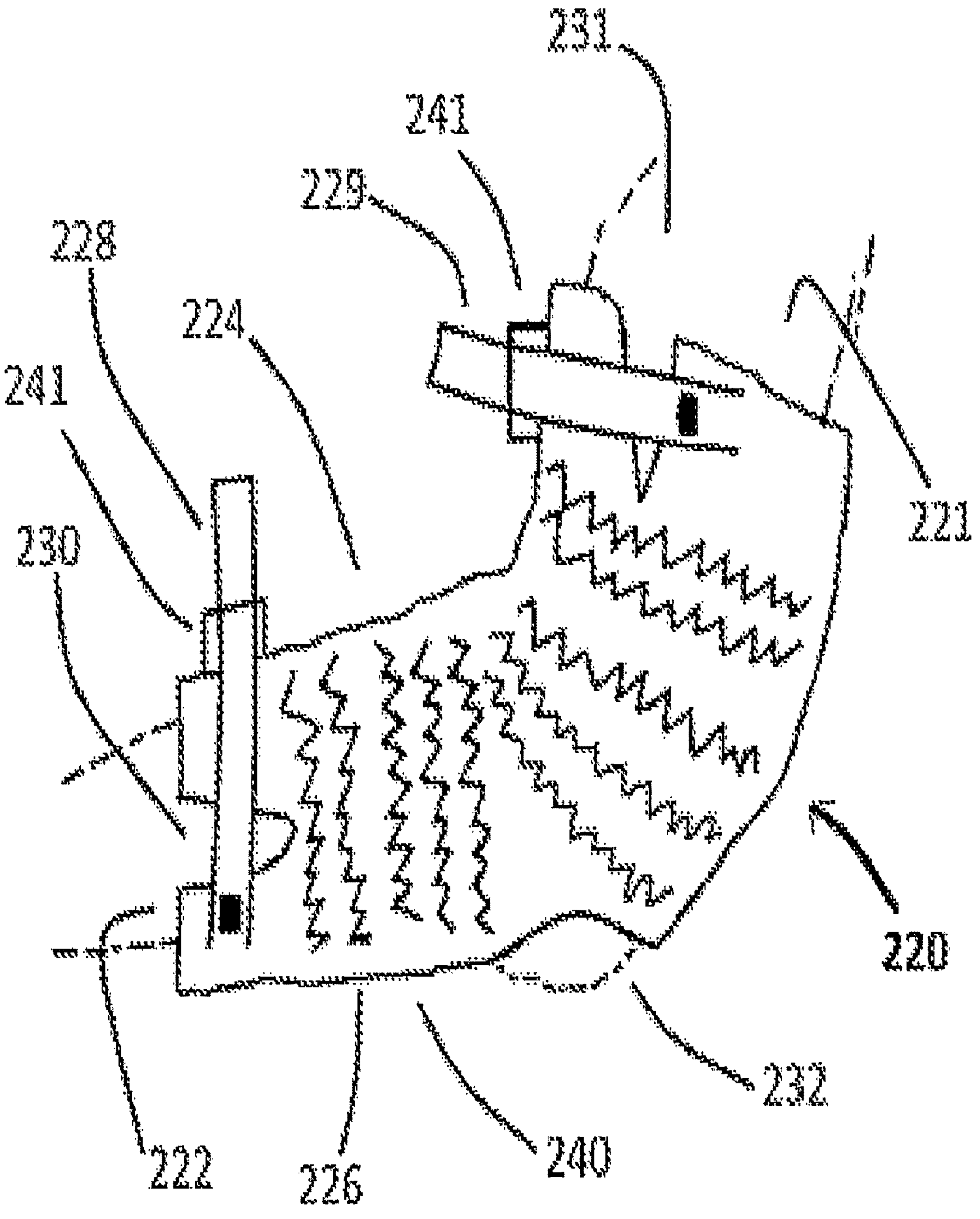
FIG. 12 is a drawing showing the dorsal side of the sports sleeve embodiment in FIG. 11.

In FIG. 11 and FIG. 12, the present invention, is shown as a tubular member, or sports sleeve 220, having a first open end 221 and a second open end 222 opposite the first end, and adapted to fit snugly around most of the arm of a user. FIG. 11 shows the palmar outer surface 223, while FIG. 12 shows the dorsal outer surface 224 of the embodiment represented in FIG. 11.

This particular tubular member sports sleeve could be formed of any tubular member material aforementioned, such as, for example of synthetic leather and nylon 220 to offer moisture and perspiration resistance. Most of a user's bicep, elbow and forearm area is covered by the sports sleeve embodiment. The palmar and dorsal portions of this embodiment are essentially the same size The sports sleeve offers a grip enhancing means in the form of depressions, throughout the entire outer surface area of the palmar 225 and dorsal portions 226 of the embodiment. Specifically, non-linear grooves 225, 226 are provided for added grip support in controlling a ball or object by providing a higher coefficient of friction than what the skin of a user might otherwise provide, preferably a Durometer A Static Coefficient of Friction of at least 1. More preferably, a Durometer A Static Coefficient of Friction of at least 1.5. The circumference of this embodiment is of sufficient dimensions to snugly receive a user's arm.

Thus since the embodiment covers most of the arm area it provides the user, such as a football player, with a more stable overall control of a football than just by using the skin of the arm while running with and cradling a football.

The sports sleeve embodiment may also have an expandable securement opening means at an open end adapted to receive the user's arm. This may comprise of a securement opening means such as but not limited to a strap which mechanically engages a strap capture mechanism to secure the sports sleeve such as, for example, a synthetic hook and loop fastening interface which adheres when pressed together, commonly using VELCRO, with a metallic or plastic brace 241 to loop around. In this case, the embodiment provides two separate securement opening means 228, 229, in the form of straps. A strap is provides along each open end of the embodiment, each overlaying a small slit 230, 231 or opening along the embodiment's dorsal portion to allow the sports sleeve to widen when a user places the embodiment around the user's arm. Alternatively, or in addition, the securement opening means may comprise of other standard used mechanisms of allowing a user to apply and disengage the sports sleeve, such as an elastic band material along an open end of the sports sleeve. Embodiments may also have combinations of both a strap capture mechanism and an elastomeric band. The expandable securement opening means may be formed integral with the sports sleeve or may be attached to the sports sleeve by standard methods, such as by sewing.

The strap can be constructed of the same material forming the embodiment or may comprise of a standard elastic formed strap, such as a flexible plastic or rubber combination.

Shown also is an aperture 232 along the dorsal surface, exposing a user's elbow, thus providing added flexibility while using the embodiment.

This embodiment overlays approximately about fifty percent of a user's bicep and about seventy-five percent of a user's forearm; essentially all of a user's elbow area is covered, with the exception of the portion exposed by the aperture along the elbow area.

A moisture absorbent material 233 may be provided along the dorsal portion of the sports sleeve, allowing a user to wipe off perspiration, a common occurrence during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, about 1/16 inch terry cloth 233 or absorbent foam stitched onto the substantially the entire top surface of a strap. Shown here, the embodiment provides two separate straps 228, 229, each affixed with terry cloth along the surface area 233, by any standard method of attachment, such as by stitching.

Additionally, embodiments such as this may be coated with a moisture repellant substance 240, such as a synthetic resin, for example, especially useful during rainy weather game situations. The moisture repellant is applied to the entire embodiment.

This embodiment, and all its described features, may of course be adapted to extend to overlay all of a user's bicep area and/or wrist area, of course.

Figure 13:
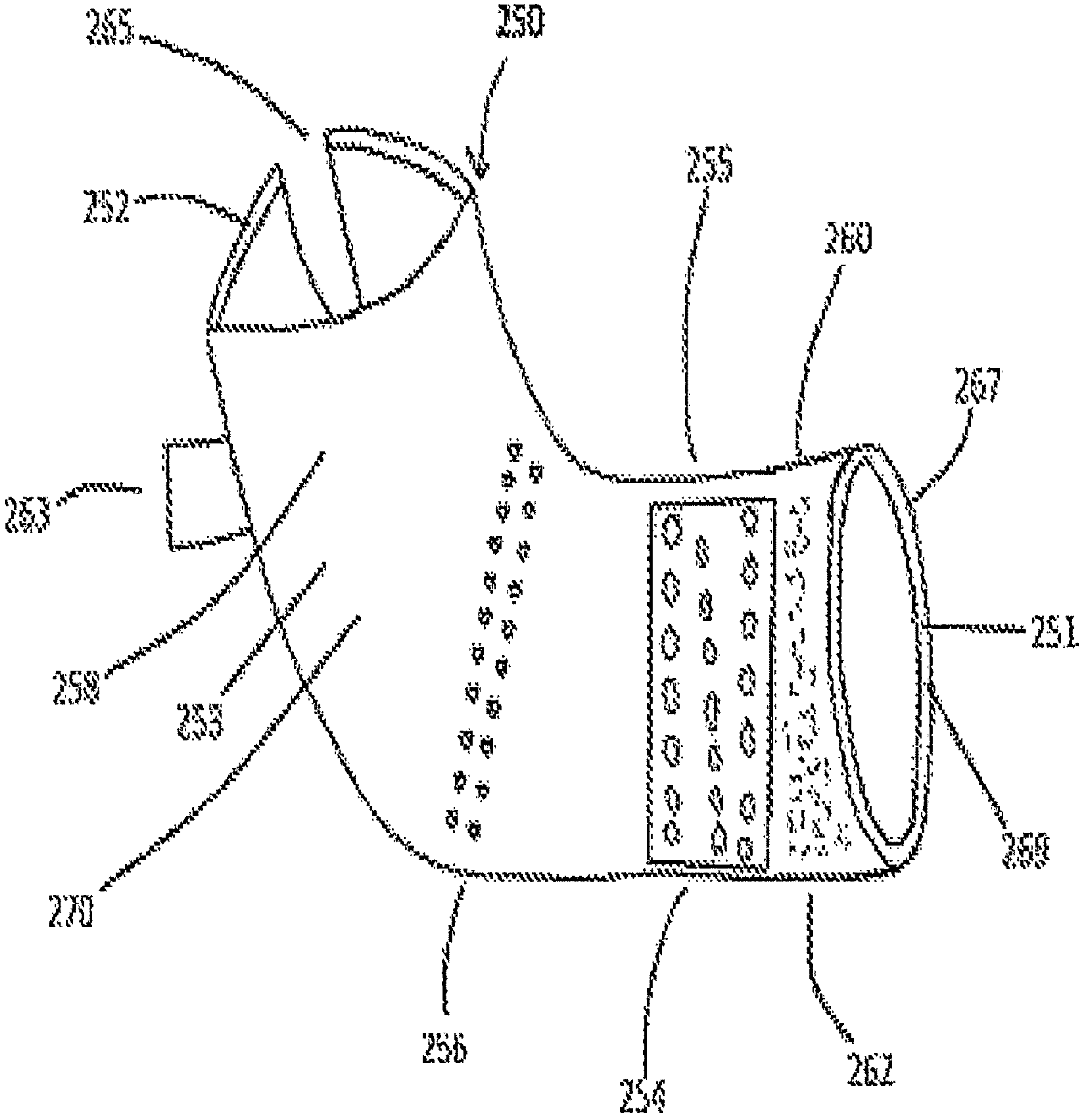
FIG. 13 is drawing showing the palmar side of another sports sleeve embodiment.
Figure 14:
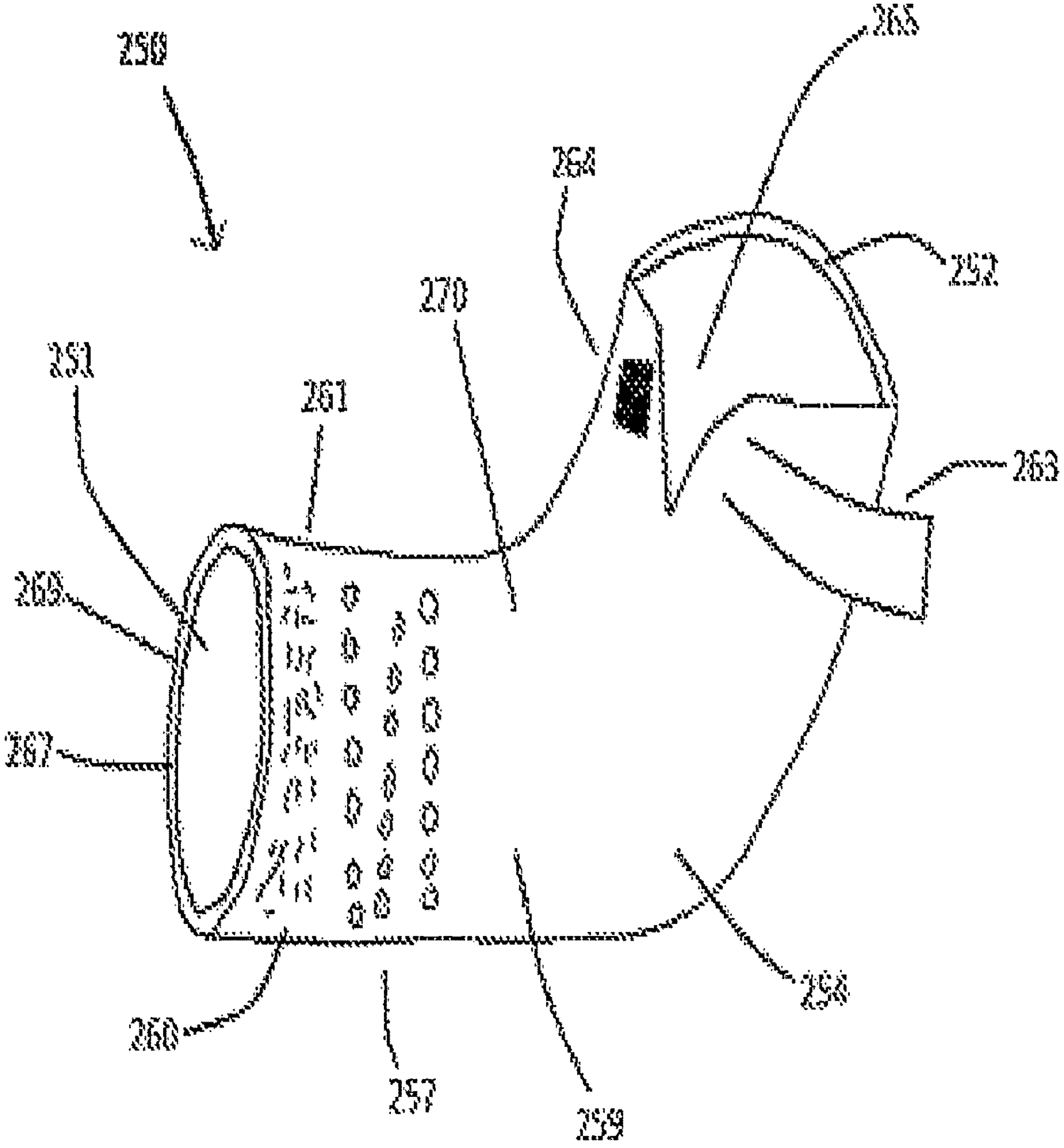
FIG. 14 is a drawing showing the dorsal side of the sports sleeve embodiment in FIG. 13.

In FIG. 13 and FIG. 14, the present invention, is shown as a tubular member, or sports sleeve 250, having a first open end 251 and a second open end 252 opposite the first end, and adapted to fit snugly around essentially the entire arm of a user. FIG. 13 shows the palmar surface 253, while FIG. 14 shows the dorsal surface 254 of the embodiment represented in FIG. 13.

This particular tubular member sports sleeve could be formed of any tubular member material aforementioned, such as, for example, a more durable material forming the palmar portion such as synthetic leather 250, and a more elastic material forming the dorsal portion such as rubber or spandex to provide added flexibility and arm movement. This embodiment is adapted to overlay essentially the entire bicep, elbow and forearm areas, including the wrist of a user. The circumference of the embodiment is wide enough to fit snug on the arm.

This sports sleeve embodiment offers a grip enhancing means along the palmar and dorsal surface, for added grip support in controlling a ball or object by providing a higher coefficient of friction than what the skin of a user might otherwise provide, preferably a Durometer A Static Coefficient of Friction of at least 1. More preferably, a Durometer A Static Coefficient of Friction of at least 1.5.

Specifically, the palmar portion overlaying a user's arm comprises of a rectangular panel 254. Formed on the panel is a grip enhancing means in the form of a plurality of vinyl circular projections 255 of at least about three hundred micrometers. The panel can be composed of any panel forming materials aforementioned, such as a vinyl material 254, and is affixed to the sports sleeve by any standard method, such as by stitching. The panel extends to overlay approximately about twenty-five percent of the palmar portion of the embodiment, but may be adapted to overlay the entire palmar portion of the arm embodiment.

Formed on the palmar surface is a second grip enhancing means. Specifically, two rows of projections 256, such as PVC heart shapes 256, are molded onto the palmar surface of the embodiment.

In addition, formed on the dorsal surface of the embodiment is a third grip enhancing means. Specifically, for example, three rows of projections 257, such as neoprene dots, are molded onto the dorsal surface, overlaying approximately about twenty-five percent of the dorsal surface, but may be configured to extend to overlay the entire dorsal surface of the embodiment.

In addition, the palmar and dorsal surfaces are coated with a fourth grip enhancing means. Specifically, for example, about fifty percent of the palmar surface 258 and twenty-five percent of the dorsal surface 259 is coated with neoprene.

A moisture absorbent material 260 may be provided along the surface of the sports sleeve, allowing a user to wipe off perspiration, a common occurrence during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, at least about 1/20 inch terry cloth 260 stitched onto the surface area of the embodiment, such as, for example, along the dorsal portion 261 and palmar portion 262 overlaying a user's wrist. Shown here, terry cloth is affixed throughout the dorsal and palmar surface area of the embodiment that overlays a user's wrist, and may be affixed by any standard method of attachment, such as by stitching.

The arm sports sleeve embodiment may also have an expandable securement opening means 263 at an open end adapted to receive the user's arm. This may comprise of a securement opening means such as but not limited to a strap which mechanically engages a strap capture mechanism to secure the sports sleeve such as, for example, a synthetic hook and loop fastening interface which adheres when pressed together, commonly using VELCRO. In this case, a strap and VELCRO mechanism 264 is provides along one open end of the embodiment, overlaying a small slit 265 or opening along the embodiment's dorsal portion to allow the sports sleeve to widen when a user places the embodiment around the user's arm. Alternatively, or in addition, the securement opening means may comprise of other standard used mechanisms of allowing a user to apply and disengage the sports sleeve, such as an elastic band material 266 along the second open end of the sports sleeve. The expandable securement opening means may be formed integral with the sports sleeve or may be attached to the sports sleeve by standard methods, such as by sewing.

The strap can generally be constructed of the same material forming the embodiment. This embodiment, and all its described features, may of course be adapted to extend to overlay a user's bicep or wrist area. The palmar and dorsal portions of this embodiment are essentially the same size.

Also shown is a liner 267. The lining material may be comprised of standard lining materials, such as a smooth, flexible knitted fabric. The liner may also comprise of flexible and elastomeric material such as spandex or LYCRA 267. Other possible materials include a knit of polyester or simply the same material forming the tubular member sports sleeve. A soft cellular plastic could also be preferred. Additionally, the liner may provide added features to offer warmth and comfort such as by comprising of a fleece material, for example, especially useful when competing in rather harsh conditions. This embodiment further provides a liner that is infused with aloe 269, thus providing additional therapeutic benefits.

Additionally, embodiments such as this may be coated with a moisture repellant substance 270, such as SCOTCH GUARD, for example, especially useful during harsh game situations. The moisture repellant is applied to the entire embodiment.

Figure 15:
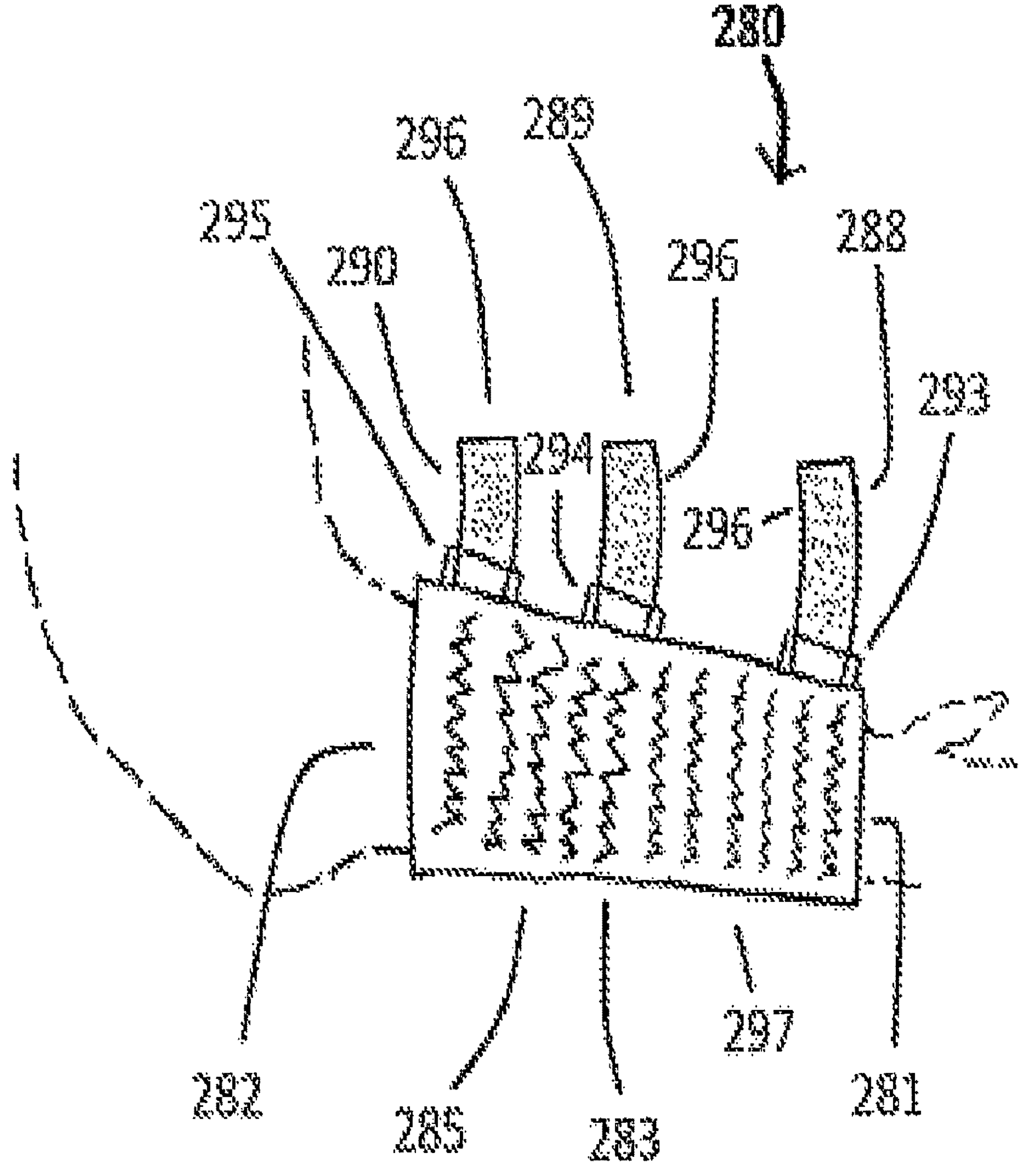
FIG. 15 is a drawing showing the palmar side of a sports sleeve embodiment on the forearm of a user.
Figure 16:
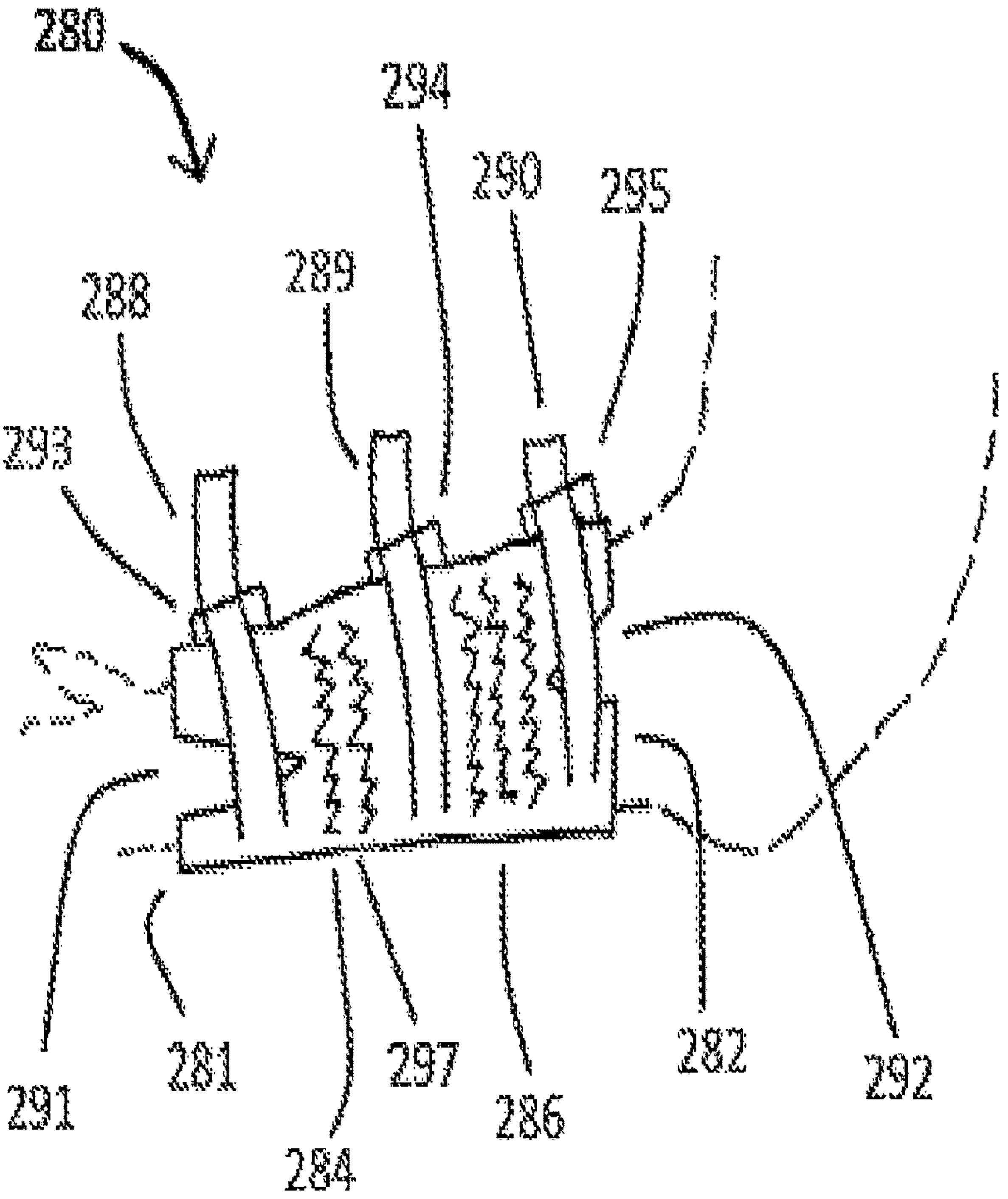
FIG. 16 is a drawing showing the dorsal side of the forearm sports sleeve embodiment in FIG. 15.

In FIG. 15 and FIG. 16, the present invention, is shown as a tubular member, or sports sleeve 280, having a first open end 281 and a second open end 282 opposite the first end, and adapted to fit snugly around the forearm of a user but does not extend to overlay more than the forearm of a user. FIG. 15 shows the palmar surface 283, while FIG. 16 shows the dorsal surface 284 of the embodiment represented in FIG. 15. The palmar and dorsal portions of this embodiment are essentially the same size. This embodiment has a circumference of substantial dimensions to receive a user's forearm, snugly.

This particular tubular member sports sleeve could be formed of any tubular member material aforementioned, such as, for example of cabretta leather and spandex to offer moisture and perspiration resistance 280. Most of the forearm area of a user is covered, but does not extend to cover more than a user's forearm.

The forearm sports sleeve offers a grip enhancing means in the form of depressions, throughout the entire outer surface area of the palmar portion 285 and dorsal portion 286 of the embodiment. Specifically, non-linear grooves 285, 286 are provided, offering increased control and grip when using the forearm embodiment.

Thus since the embodiment covers most of the forearm area it provides the user, such as a volleyball player, with a more stable overall control of a volleyball upon impact than just by using the skin of the forearm for impact.

This sports sleeve embodiment may also have an expandable securement opening means at an open end adapted to receive the user's hand. This may comprise of a securement opening means such as but not limited to a strap which mechanically engages a strap capture mechanism to secure the sports sleeve such as, for example, a synthetic hook and loop fastening interface which adheres when pressed together, commonly using VELCRO. In this case, the embodiment provides three separate securement opening means, in the form of straps capture mechanisms 288, 289, 290. A strap capture mechanism is provided along a first open end 288 as well as along a second open end 290, each overlaying a small slit 291, 292 or opening along the embodiment's dorsal portion to allow the sports sleeve to widen when a user places the embodiment around the user's forearm. A third securement opening means 289 in the form of a strap capture mechanism is provided at about the middle of the embodiment, further creating a tight fit around a user's forearm. Alternatively, the opening means may comprise of other standard used mechanisms of allowing a user to apply and disengage the sports sleeve, such as an elastic band material along an open end of the sports sleeve. Embodiments may also have combinations of both a strap capture mechanism and an elastomeric band. The expandable securement opening means may be formed integral with the sports sleeve or may be attached to the sports sleeve by standard methods, such as by sewing.

The strap can generally be constructed of the same material forming the embodiment. The embodiment also illustrates how braces 293, 294, 295 may be provided so that a user may wrap the strap around the brace for an even tighter securement. The braces may be formed of any standard material, such as plastic, rubber or metal materials.

A moisture absorbent material 296 may be provided along the dorsal portion of the sports sleeve, allowing a user to wipe off perspiration commonly on a user's face during active sports play. The moisture absorbent material may be secured anywhere along the dorsal surface or on the securement opening means, such as affixed to the top surface of each strap 296. The moisture absorbent material may be formed of any moisture absorbent material aforementioned, such as, for example, about ⅛ inch terry cloth 296 stitched onto the substantially the entire top surface of each strap. Shown here, the embodiment provides three separate straps, each affixed with terry cloth along the surface area, by any standard method of attachment, such as by stitching.

Additionally, embodiments such as this may be coated with a moisture repellant substance 297, such as SCOTT GUARD, for example, especially useful in game situations where perspiration can often be at issue. The moisture repellant is applied to the entire embodiment.

This embodiment, and all its described features, may of course be adapted to extend to overlay a user's bicep or wrist area.

Figure 17:
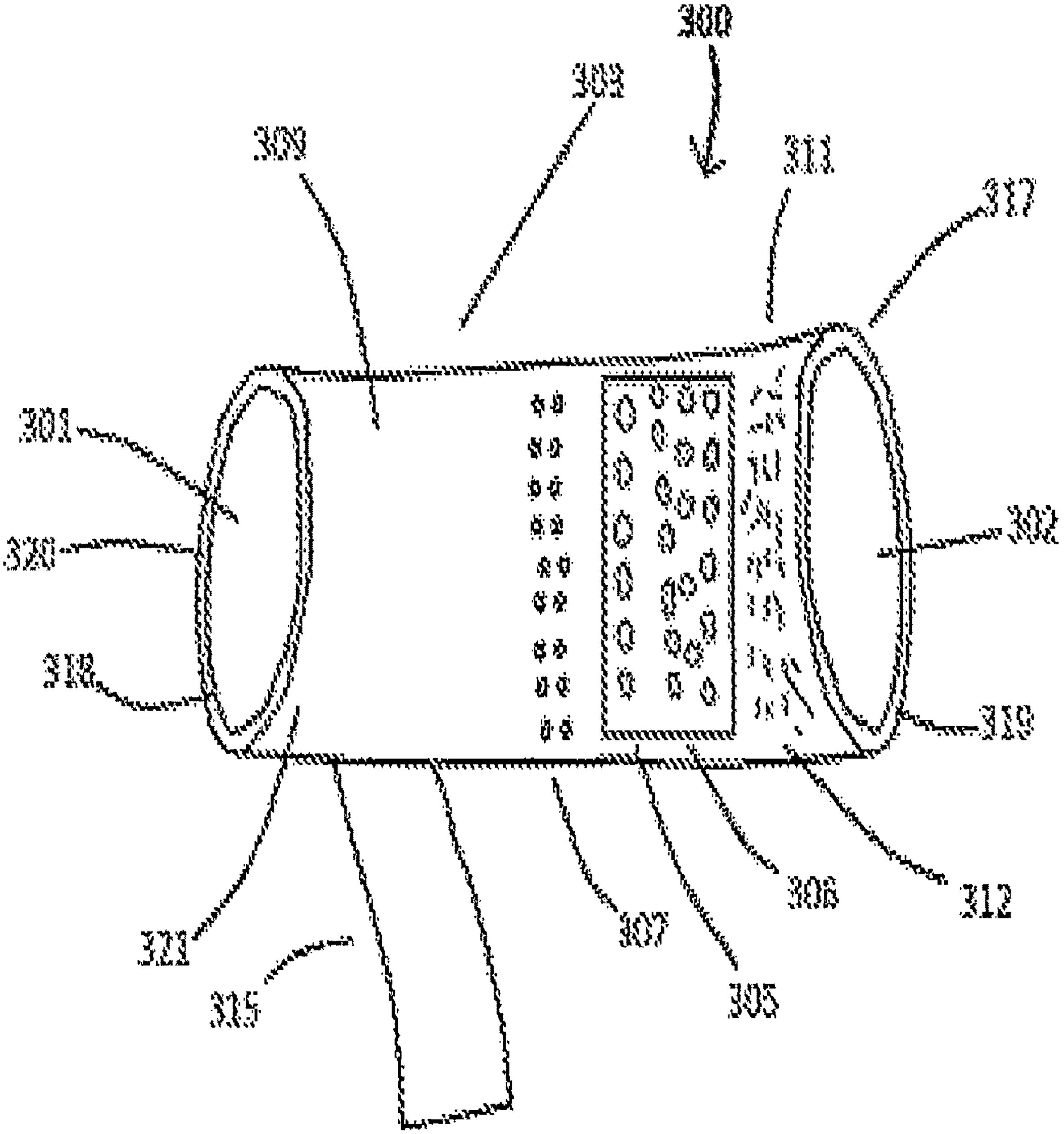
FIG. 17 is a drawing showing the palmar side of another sports sleeve embodiment.
Figure 18:
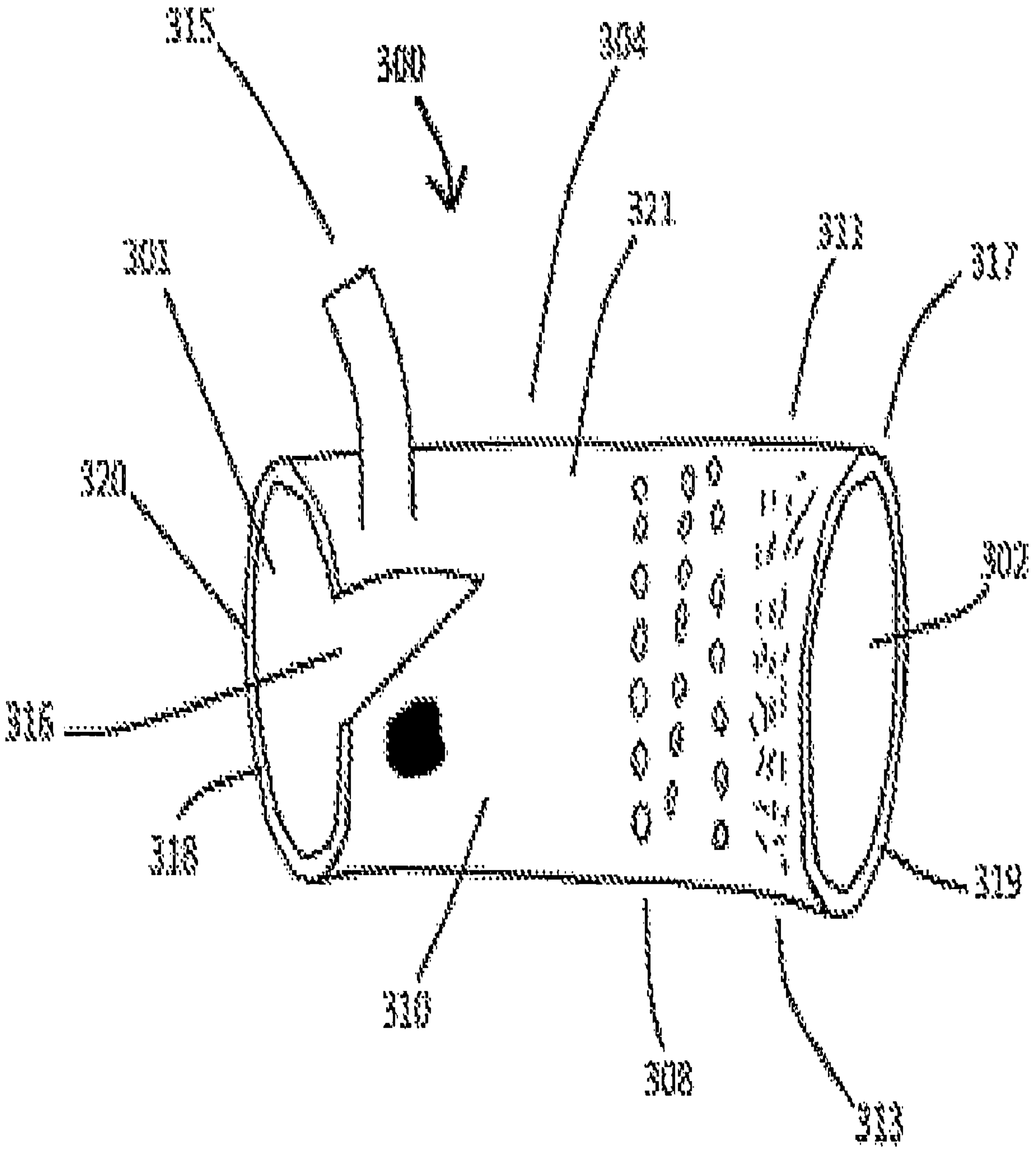
FIG. 18 is a drawing showing the dorsal side of the sports sleeve embodiment in FIG. 17.

In FIG. 17 and FIG. 18, the present invention, is shown as a tubular member, or sports sleeve 300, having a first open end 301 and a second open end 302 opposite the first end, and adapted to have a circumference of substantial size to fit the embodiment snugly around the forearm of a user. FIG. 17 shows the palmar surface 303, while FIG. 18 shows the dorsal surface 304 of the embodiment represented in FIG. 17. The palmar and dorsal portions of this embodiment are essentially the same size.

This particular tubular member sports sleeve could be formed of any tubular member material aforementioned, such as, for example of a rubber and spandex to offer moisture and perspiration resistance 300. The entire forearm area of a user is covered and extends to cover the wrist area, but does not extend to cover a user's bicep or hand.

The forearm sports sleeve offers a grip enhancing means along the palmar and dorsal surface, for added grip support in controlling a ball or object by providing a higher coefficient of friction than what the skin of a user might otherwise provide, preferably a Durometer A Static Coefficient of Friction of at least 1. More preferably, a Durometer A Static Coefficient of Friction of at least 1.5.

Specifically, the palmar portion overlaying a user's forearm comprises of a rectangular panel 305. Formed on the panel is a plurality of projections 306, such as, for example PVC dots projections of at least about three hundred micrometers. The panel can be composed of any panel forming materials aforementioned, such as a neoprene material 305, and is affixed to the sports sleeve by any standard method, such as by stitching. The panel extends to overlay approximately about twenty-five percent of the embodiment's palmar portion, but may be adapted to overlay the entire palmar portion of the forearm embodiment. Formed on the palmar surface is a second grip enhancing means. Specifically, two rows of projections 307, such as PVC beads, are molded onto the palmar surface of the embodiment. In addition, formed on the dorsal surface is a third grip enhancing means for the embodiment. Specifically, for example, three rows of projections 308, such as neoprene dots, are molded onto the dorsal surface, overlaying approximately about twenty-five percent of the dorsal surface of the embodiment, but may be configured to extend to overlay the entire dorsal surface of the embodiment. In addition, the palmar and dorsal surfaces are coated with a fourth grip enhancing means. Specifically, for example, about fifty percent of the palmar surface 309 and twenty-five percent of the dorsal surface 310 is coated with latex.

A moisture absorbent material 311 may be provided along the dorsal portion of the sports sleeve, allowing a user to wipe off perspiration commonly on a user's face during active sports play. The moisture absorbent material may be secured anywhere along the dorsal surface or on the securement opening means, such as affixed to the top surface of a strap. The moisture absorbent material may be formed of any moisture absorbent material aforementioned, such as, for example, of at least about 1/20 inch terry cloth 311 stitched onto the dorsal surface area of the embodiment, such as, for example, along the dorsal portion overlaying a user's wrist. Shown here, terry cloth is affixed throughout the dorsal 313 and palmar surface 312 area that overlays a user's wrist, and may be affixed by any standard method of attachment, such as by stitching.

The forearm sports sleeve embodiment may also have an expandable securement opening means 315 at an open end adapted to receive the user's hand. This may comprise of a securement opening means such as but not limited to a strap which mechanically engages a strap capture mechanism to secure the sports sleeve such as, for example, a synthetic hook and loop fastening interface which adheres when pressed together, commonly using VELCRO. In this case, a strap and capture VELCRO mechanism 315 is provided along the open end of the embodiment, and is overlaying a small slit or opening 316 along the embodiment's dorsal portion to allow the sports sleeve to widen when a user places the embodiment around the user's forearm. In addition, the securement opening means may comprise of other standard used mechanisms of allowing a user to apply and disengage the sports sleeve, such as an elastic band material 317 along the second open end of the sports sleeve, such as an elastomeric band fixed around an open end of the embodiment. The expandable securement opening means may be formed integral with the sports sleeve or may be attached to the sports sleeve by standard methods, such as by sewing. The strap and capture mechanism can generally be constructed of the same material forming the embodiment or of any securement opening means materials aforementioned.

Also shown is a liner 318. The lining material may be comprised of standard lining materials, such as a smooth, flexible knitted fabric 318. The liner may also comprise of flexible and elastomeric material such as spandex or LYCRA. Other possible materials include a knit of polyester or simply the same material forming the tubular member sports sleeve. A soft cellular plastic could also be preferred. Additionally, the liner may provide added features to offer warmth and comfort such as by comprising of a fleece material 319, for example, especially useful when competing in harsher conditions. This embodiment further provides a liner that is infused with aloe 320, thus providing additional therapeutic benefits.

Additionally, embodiments such as this may be coated with a water repellant substance 321, such as a synthetic resin, for example, especially useful during active outdoor game play. The water repellant is applied to the entire embodiment.

This embodiment, and all its described features, may of course be adapted to extend to overlay a user's bicep or wrist area.

Figure 19:
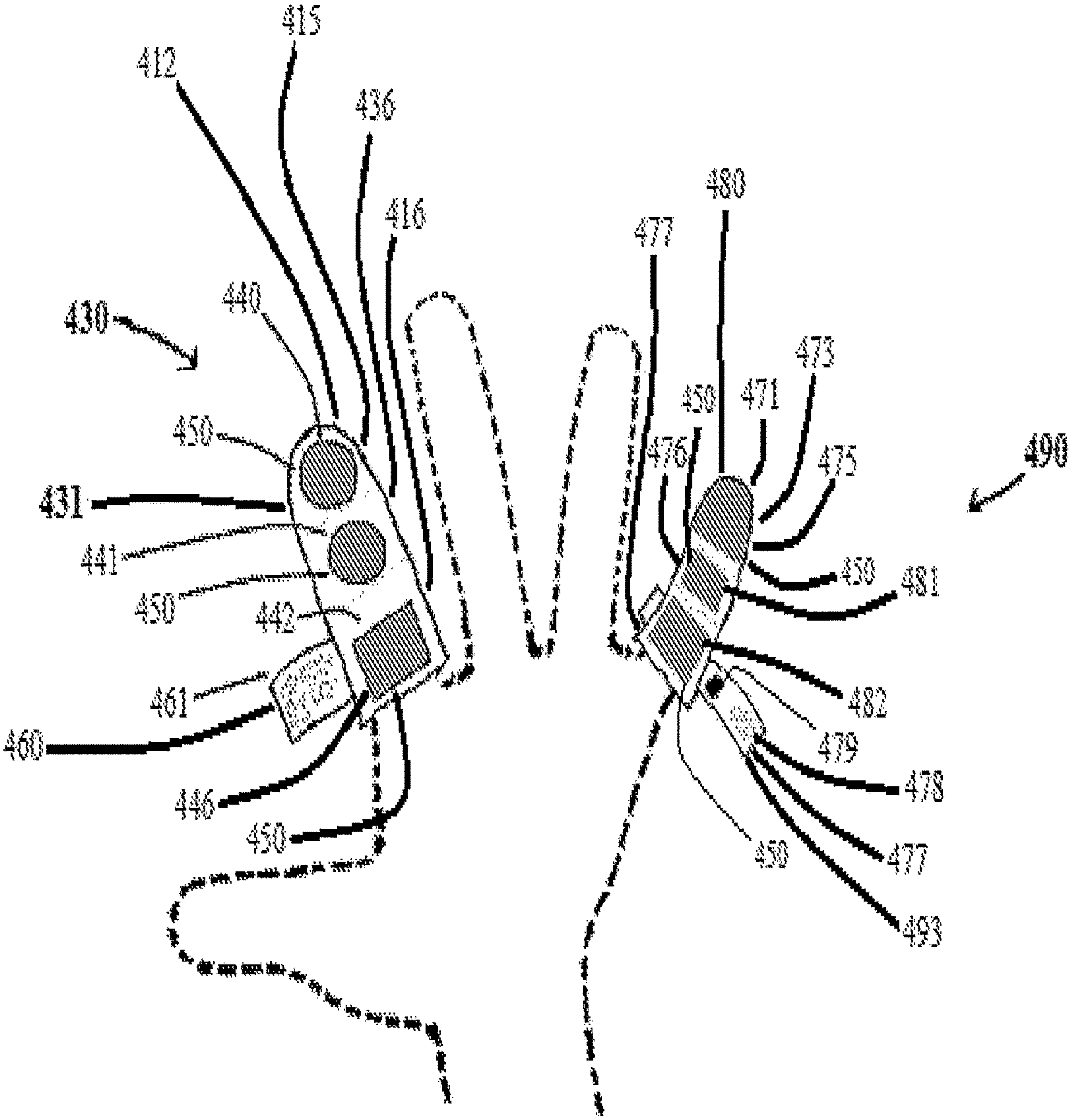
FIG. 19 is a drawing of finger cot embodiments on the left hand of the user, showing the palmar surfaces.
Figure 20:
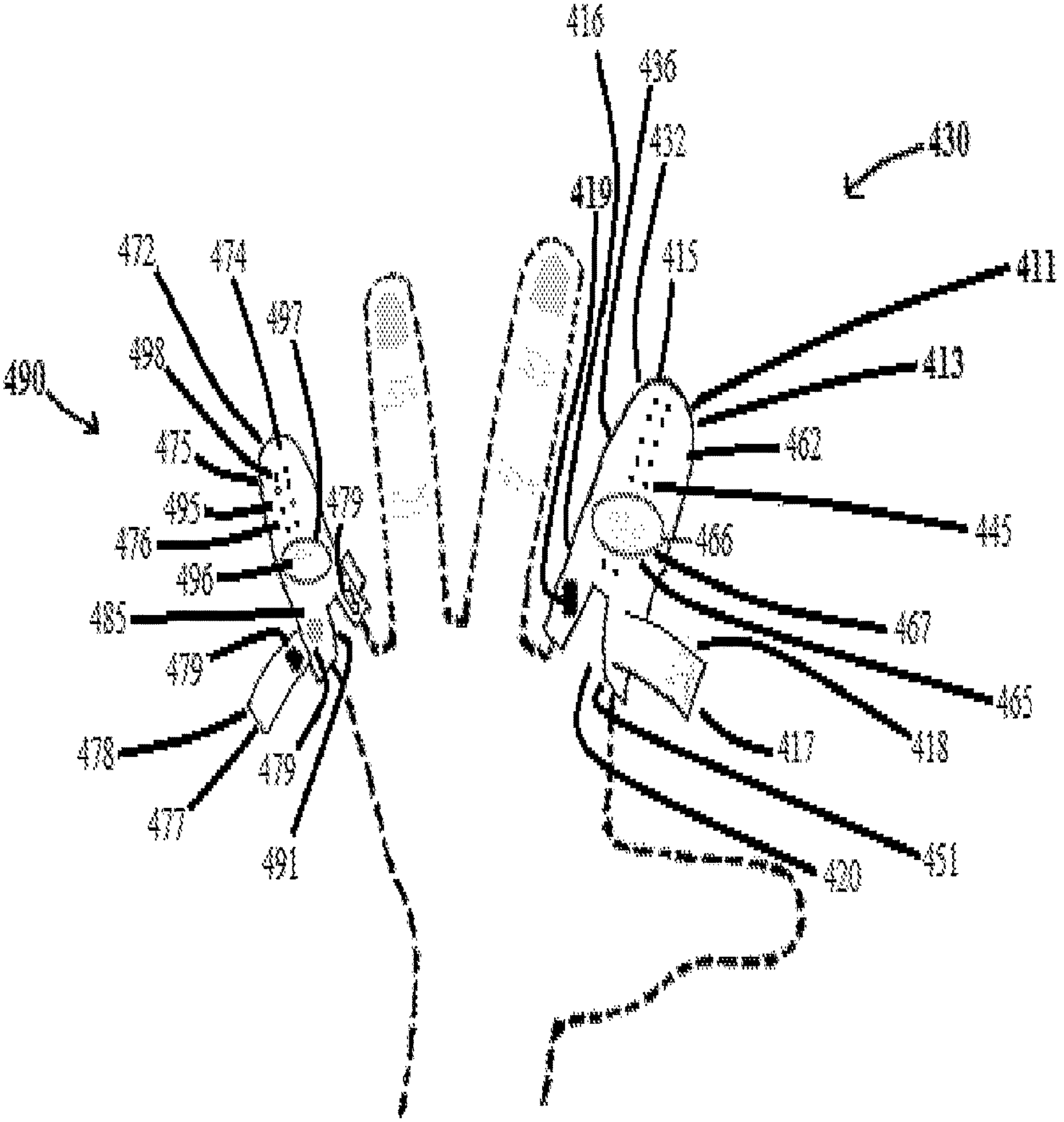
FIG. 20 is a drawing showing the dorsal surfaces of the embodiments in FIG. 19.

Referring now to FIG. 19 and FIG. 20, the present invention is shown as various grip-enhancing finger cot embodiments with a panel formed of a tackified material. As aforementioned, the finger cot tubular member embodiments of the present invention all have a body adapted to fit around a digital segment of a human hand, and are adapted to overlay at least one phalanx of a user's finger without overlying another finger of the user's hand. The finger cot embodiments shown on FIG. 19 and FIG. 20 all have a palmar portion that cover the palm side of the finger, and a dorsal portion that covers the back of the user's finger. More specifically, the finger cot embodiments 430, 490 all have a closed first end comprising a distal portion material that overlays the distal phalanx, and a second end comprising a proximal portion material that overlays the proximal phalanx of the user's finger when the embodiment is worn. The distal portion includes the finger cot distal end, and the proximal portion includes the finger cot proximal end.

These finger cot embodiments all have a first grip enhancing panel on the distal portion of the finger cot palmar portion. The first grip enhancing panel is made of a high grip tackified leather material, and is of substantial size to cover essentially the entire palm side of the distal phalanx of wearer's digital segment when the finger cot is worn.

Shown on a user's left hand are two separate finger cot embodiments 430 and 490. Each embodiment could be used independently or in combinations. These embodiments have a circumference large enough to be able to fit tightly around select areas of a digital segment, but do not extend to overlay a second digital segment.

One finger cot embodiment is shown and designated as 430. The palmar view 431 of the finger cot is drawn in FIG. 19, and the dorsal view 432 of the same finger cot is drawn in FIG. 20. This finger cot has a body adapted to fit snugly around a forefinger of a human hand, said body is of substantial size to overlay at least one phalanx of the digital segment without overlying another digital segment of the wearer's hand. The forefinger finger cot body has a palmar portion 412 and a dorsal portion 413. The forefinger finger cot body also has a distal end, said distal end is closed to enclose the user's digital segment. The forefinger finger cot body also has a proximal end which has an opening adapted to receive the digital segment of the user. The forefinger finger cot body longitudinally extends from said distal end to said proximal end.

The forefinger finger cot body also has a distal portion 415 which is of substantial size and positioned to overlay essentially the entire distal phalanx of the wearer's digital segment but does not extend to overlay beyond the distal phalanx. The forefinger finger cot body distal portion includes a distal end as well as a first grip enhancing panel 440 disposed on the palmar portion of the distal portion 415.

The forefinger finger cot body also has a middle portion 436 which is of substantial size and positioned to overlay essentially the entire middle phalanx of the wearer's digital segment. The forefinger finger cot body middle portion includes a second grip enhancing panel 441 disposed on the palmar portion of the forefinger finger cot body middle portion and is of substantial size and positioned overlay a middle phalanx of the user's digital segment but does not extend beyond the middle phalanx when the finger cot is worn.

The forefinger finger cot body also has a proximal portion 416 which is of substantial size and positioned to overlay a proximal phalanx of the wearer's digital segment.

The forefinger finger cot body middle portion longitudinally extends between the forefinger finger cot body distal portion and the forefinger finger cot body proximal portion.

The forefinger finger cot body proximal portion includes the proximal end as well as a third grip enhancing panel 442. The third grip enhancing panel is disposed on the palmar portion of the proximal portion and is adapted to overlay the proximal phalanx of the user's digital segment but does not extend beyond the proximal phalanx portion when the finger cot is worn. The proximal end is open to receive the user's digital segment, and also includes an expandable securement opening means 417 comprising of a strap 418 and hook and loop fasteners 419 so that the user can manually engage and disengage the finger cot. The proximal end also includes a slit along the dorsal side whereby the strap can extend over the slit 420.

The forefinger finger cot first grip enhancing panel 440, second grip enhancing panel 441 and third grip enhancing panel 442 are each formed of a high grip tackified leather material 450 and can be created and secured to the forefinger finger cot by any standard mechanism, such as stitching. The grip enhancing panels enhance a user's ability of controlling a ball or an object by providing a higher coefficient of friction than what the skin of a user might otherwise provide, preferably a Coefficient of Friction of at least 2.0. More preferably, a Coefficient of Friction of at least 2.5. It is important to note that the first grip enhancing panel, the second grip enhancing panel and the third grip enhancing panel each only overlay one phalanx of the user's digital segment. This unique structural feature allows the user to flex and bend the digital segment unhindered as the tackified leather material is smooth but bulky and inhibits significant bending.

The dorsal portion (or back) can be constructed primarily of the same materials forming the palmar portion, such as a leather or synthetic leather for example.

The finger cot embodiment also has an expandable securement opening means 417 at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit 420 or opening along the embodiment's dorsal portion to allow the finger cot to enclose a digital segment of a user, such as on a user's forefinger, for example. In addition, the opening securement means comprises an elastomeric band 451 fixed around the open ends of the embodiments. The expandable securement opening means may be formed integral with the finger cot or may be attached to the finger cot by standard methods, such as by sewing. The strap 418 can generally be constructed of the same material forming the finger cot.

A moisture absorbent material 460 is provided along the dorsal portion of the finger cot, allowing a user to wipe off perspiration commonly on a user's face during active sports play. The moisture absorbent material may be secured anywhere along the dorsal surface or on the securement opening means, such as affixed to the top surface of a strap, and does not extend to the finger cot palmar portion. The moisture absorbent material may be formed of any moisture absorbent material aforementioned, such as, for example, about 1/12 inch terry cloth 461 stitched onto the substantially the entire top surface of a strap.

Additionally, embodiments such as this may be coated with a water repellant substance 462, such as a synthetic resin, for example, especially useful during rainy weather game situations. The water repellant is applied to the entire embodiment.

Shown also is an aperture 465 which leaves exposed a user's interphalangeal joint 466. The aperture allows a user to more easily flex and maneuver his or her finger during active sports play, particularly when bending and flexing the digital segment during game play. The edge of the aperture is stitched 467 to prevent fraying along the aperture.

Shown also are microrecesses 445 along the dorsal surface overlaying a user's middle phalanx, for enhanced moisture management capabilities. These microrecesses are generally about 0.120 millimeters in diameter.

A second finger cot embodiment is shown and designated as 490. The palmar view 471 of the finger cot is drawn in FIG. 19, and the dorsal view 472 of the same finger cot is drawn in FIG. 20. This finger cot has a body adapted to fit snugly around a pinkie finger of a human hand, said body is of substantial size to overlay at least one phalanx of the digital segment without overlying another digital segment of the user's hand. The pinkie finger finger cot body has a palmar portion 473 and a dorsal portion 474. The pinkie finger finger cot body also has a distal end, said distal end is closed to enclose the user's digital segment. The pinkie finger finger cot body also has a proximal end which has an opening adapted to receive the digital segment of the user. The pinkie finger finger cot body longitudinally extends from said distal end to said proximal end.

The pinkie finger finger cot body also has a distal portion 475 which is of substantial size and positioned to overlay essentially the entire distal phalanx of the user's digital segment but does not extend to overlay beyond the distal phalanx. The pinkie finger finger cot body distal portion includes a distal end as well as a first grip enhancing panel 480 disposed on the palmar portion of the distal portion.

The pinkie finger finger cot body also has a middle portion 476 which is of substantial size and positioned to overlay essentially the entire middle phalanx of the user's digital segment. The pinkie finger finger cot body middle portion includes a second grip enhancing panel 481 disposed on the palmar portion of the pinkie finger finger cot body middle portion and is of substantial size and positioned overlay a middle phalanx of the user's digital segment but does not extend beyond the middle phalanx when the finger cot is worn.

The pinkie finger finger cot body also has a proximal portion 477 which is of substantial size and positioned to overlay a proximal phalanx of the user's digital segment.

The pinkie finger finger cot body middle portion longitudinally extends between the pinkie finger finger cot body distal portion and the pinkie finger finger cot body proximal portion.

The pinkie finger finger cot body proximal portion includes the proximal end as well as a third grip enhancing panel 482. The third grip enhancing panel is disposed on the palmar portion of the proximal portion and is adapted to overlay the proximal phalanx of the user's digital segment but does not extend beyond the proximal phalanx portion when the finger cot is worn. The proximal end is open to receive the user's digital segment, and also includes an expandable securement opening means 477 comprising of a strap 478 and hook and loop fasteners 479 so that the user can manually engage and disengage the finger cot. The proximal end also includes a slit along the dorsal side whereby the strap can extend over the slit 491.

The pinkie finger finger cot first grip enhancing panel 480, second grip enhancing panel 481 and third grip enhancing panel 482 are each formed of a high grip tackified leather material 450 and can be created and secured to the pinkie finger finger cot by any standard mechanism, such as stitching. The grip enhancing panels enhance a user's ability of controlling a ball or an object by providing a higher coefficient of friction than what the skin of a user might otherwise provide, preferably a Coefficient of Friction of at least 2.0. More preferably, a Coefficient of Friction of at least 2.5. It is important to note that the first grip enhancing panel, the second grip enhancing panel and the third grip enhancing panel each only overlay one phalanx of the user's digital segment.

The dorsal portion of the pinkie finger finger cot may be constructed of the same material as the material forming the palmar portion, such as nylon 485 or leather material.

The pinkie finger finger cot also has an expandable securement opening means at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit 491 or opening along the embodiment's dorsal portion to allow the finger cot to enclose a digital segment of a user, such as on a user's forefinger, for example. In addition, the opening securement means comprises an elastomeric band 492 fixed around the open ends of the embodiments. The expandable securement opening means may be formed integral with the finger cot or may be attached to the finger cot by standard methods, such as by sewing. The strap can generally be constructed of the same material forming the finger cot.

A moisture absorbent material 493 is provided along the dorsal portion of the finger cot, allowing a user to wipe off perspiration commonly on a user's face during active sports play. The moisture absorbent material may be secured anywhere along the dorsal surface or on the securement opening means, such as affixed to the top surface of a strap, and does not extend to the finger cot palmar portion. The moisture absorbent material may be formed of any moisture absorbent material aforementioned, such as, for example, about 1⁄12 inch terry cloth 494 stitched onto the substantially the entire top surface of a strap.

Additionally, embodiments may be coated with a water repellant substance 495, such as a synthetic resin, for example, especially useful during rainy weather game situations. The water repellant is applied to the entire embodiment.

Shown also is an aperture 496 which leaves exposed a user's interphalangeal joint 497. The aperture allows a user to more easily flex and maneuver his or her finger during active sports play. The edge of the aperture is stitched to prevent fraying along the aperture.

Shown also are microrecesses 498 along the dorsal surface overlaying a user's middle phalanx, for enhanced moisture management capabilities. These microrecesses are generally about 0.120 millimeters or so in diameter.

These finger cot embodiments, individually or in combination, offer the ability in one respect, to essentially separate a conventional glove into its different components and then selectively choose which components to wear. This can be especially important for those individuals who need to retain heightened sensitivities in part of the hand, but need grip support in another part of the same hand. Using gloves instead of finger embodiments for these individuals would also be an unnecessary waste of materials.

The grip enhancing panels formed of a tackified leather material can be created by coating or impregnating tackifiers including tackifier resins, such as rosins and their derivatives, terpenes, aliphatic, cycloaliphatic and aromatic resin, and any of a variety of hydrocarbon-type resins, tackifier coatings, tackified materials onto a leather or synthetic leather material. Creating a grip enhancing grip panel formed of a tackified leather can be created, for example, by impregnating a leather 450 with a tackifier resin and then affixing said material forming the panel onto the rest of the palmar portion of the glove body. This particular configuration provides for maximum grip capabilities for a user, such as a golfer. Alternatively, a grip enhancing panel formed of a tackified leather material may be created by spraying a tackifier coating, such as POWR TAC SPRAY-ON TACKIFIER onto a genuine leather material and subsequently affixing the newly formed grip enhancing panel onto the finger cot body palmar portion.

Figure 21:
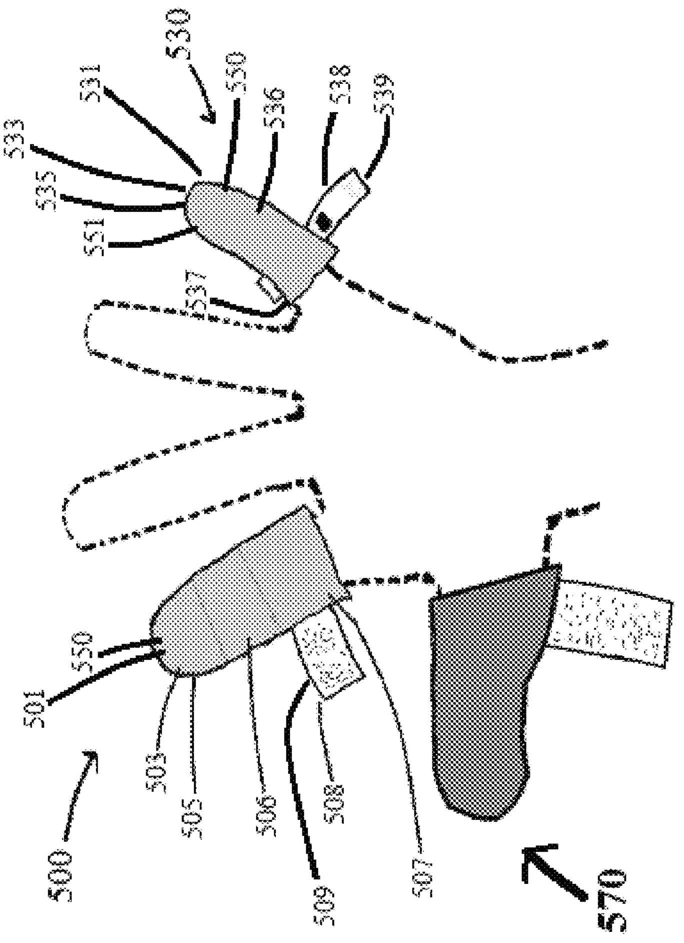
FIG. 21 is a drawing of finger cot embodiment on the left hand of the user, showing the palmer surfaces.
Figure 22:
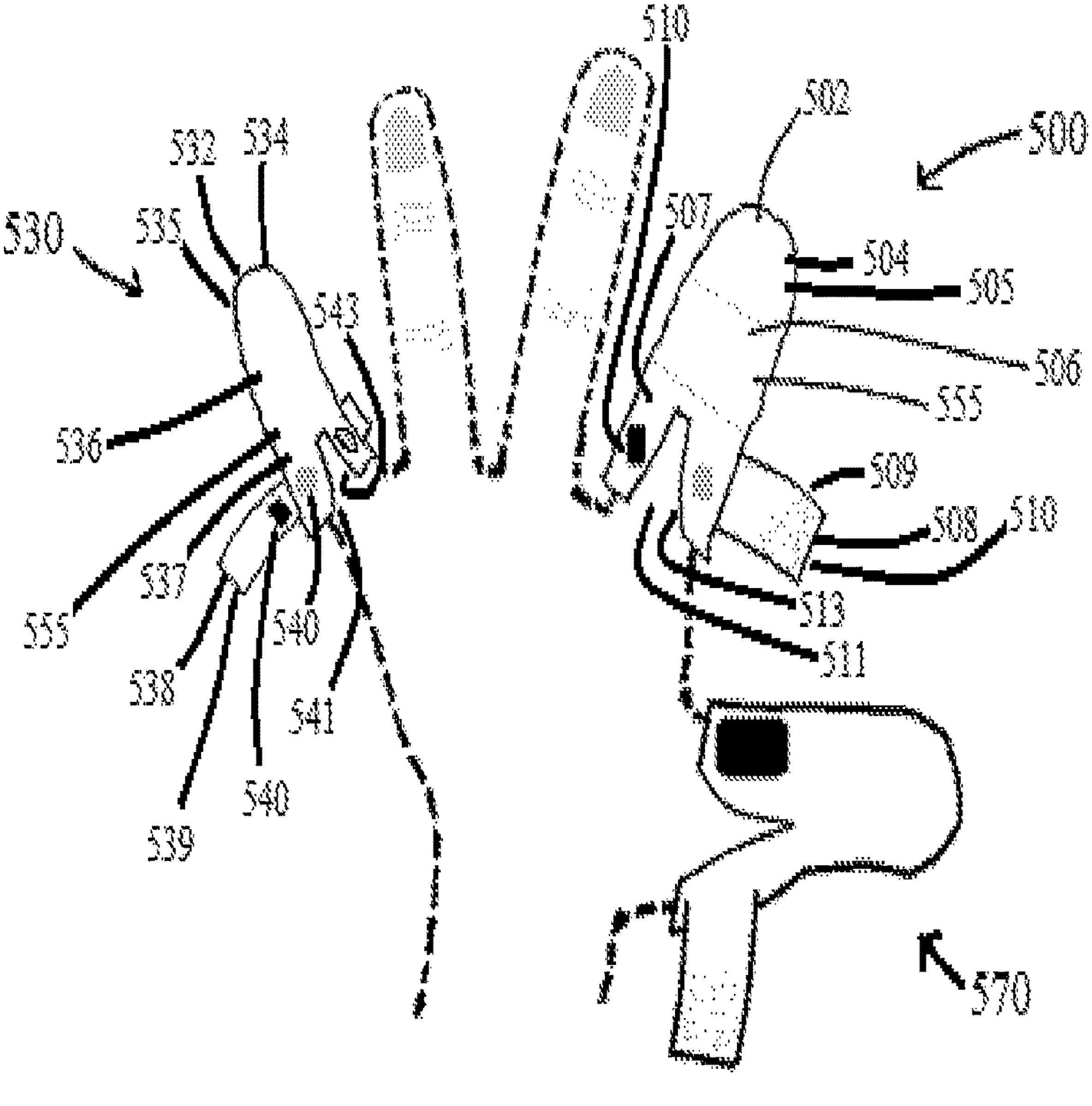
FIG. 22 is a drawing showing the dorsal surfaces of the embodiments in FIG. 21.

Referring now to FIG. 21 and FIG. 22, the present invention is shown as various grip-enhancing finger cot embodiments with only one panel formed of a tackified material on the palmar portion of the finger cot body. As aforementioned, the finger cot tubular member embodiments of the present invention all have a body adapted to fit around a digital segment of a human hand, and are adapted to overlay at least one phalanx of a user's finger without overlying another finger of the user's hand. The finger cot embodiments shown on FIG. 21 and FIG. 22 all have a palmar portion that cover the palm side of the finger, and a dorsal portion that covers the back of the user's finger. More specifically, the finger cot embodiments 500, 530, 570 all have a closed first end comprising a distal portion material that overlays the distal phalanx, and a second end comprising a proximal portion material that overlays the proximal phalanx of the user's finger when the embodiment is worn. The distal portion includes the finger cot distal end, and the proximal portion includes the finger cot proximal end.

These finger cot embodiments all have a high grip tackified leather material 550 forming essentially the entire palmar portion of these finger cot embodiments. The high grip tackified leather material and is of substantial size to cover essentially the entire palm side of the distal phalanx, middle phalanx and proximal phalanx of wearer's digital segment when the finger cot is worn. The dorsal portion of these finger cot embodiments are formed of an elastic material, having a higher expanding capability than the tackified leather material forming the palmar portion.

Shown on a wearer's left hand are separate finger cot embodiments 500, 530 and 570. Each embodiment could be used independently or in combinations. These embodiments have a circumference large enough to be able to fit tightly around select areas of a digital segment, but do not extend to overlay a second digital segment.

One finger cot embodiment is shown and designated as 500. The palmar view 501 of the finger cot is drawn in FIG. 21, and the dorsal view 502 of the same finger cot is drawn in FIG. 22. This finger cot has a body adapted to fit snugly around a forefinger of a human hand, said body is of substantial size to overlay at least one phalanx of the digital segment without overlying another digital segment of the user's hand. The forefinger finger cot body has a palmar portion 503 and a dorsal portion 504. The forefinger finger cot body also has a distal end, said distal end is closed to enclose the user's digital segment. The forefinger finger cot body also has a proximal end which has an opening adapted to receive the digital segment of the user. The forefinger finger cot body longitudinally extends from said distal end to said proximal end.

The forefinger finger cot body also has a distal portion 505 which is of substantial size and positioned to overlay essentially the entire distal phalanx of the user's digital segment. The forefinger finger cot body distal portion includes a distal end. The distal portion includes a dorsal portion that covers the back of the digital segment, and a palmar portion that covers the front (palmar) of the digital segment.

The forefinger finger cot body also has a middle portion 506 which is of substantial size and positioned to overlay essentially the entire middle phalanx of the user's digital segment. The middle portion includes a dorsal portion that covers the back of the digital segment, and a palmar portion that covers the front (palmar) of the digital segment.

The forefinger finger cot body also has a proximal portion 507 which is of substantial size and positioned to overlay a proximal phalanx of the user's digital segment. The proximal portion section includes a dorsal portion that covers the back of the digital segment, and a palmar portion that covers the front (palmar) of the digital segment.

The forefinger finger cot body middle portion longitudinally extends between the forefinger finger cot body distal portion and the forefinger finger cot body proximal portion.

The forefinger finger cot body proximal portion includes the proximal end which is open to receive the user's digital segment, and also includes an expandable securement opening means 508 comprising of a strap 509 and hook and loop fasteners 510 so that the user can manually engage and disengage the finger cot. The proximal end also includes a slit along the dorsal side whereby the strap can extend over the slit 511.

The entire forefinger finger cot palmar portion is essentially entirely formed of a high grip tackified leather material 550 and can be created and secured to the forefinger finger cot by any standard mechanism, such as stitching to the finger cot dorsal portion. The high grip tackified leather material enhances a user's ability of controlling a ball or an object by providing a higher coefficient of friction than what the skin of a user might otherwise provide, preferably a Coefficient of Friction of at least 2.0. More preferably, a Coefficient of Friction of at least 2.5. In other words, the entire palmar portion of the forefinger finger cot body distal portion is formed of a high grip tackified leather material, the entire palmar portion of the forefinger finger cot body middle portion is formed of a high grip tackified leather material, and the entire palmar portion of the forefinger finger cot body proximal portion is formed of a high grip tackified leather material. Preferably, the forefinger finger cot body palmar portion is one uniform high grip tackified leather that is therefore of substantial size to overlay the user's entire distal phalanx, entire middle phalanx and entire proximal phalanx. The high grip tackified leather material could then be affixed to the forefinger finger cot dorsal portion to form the forefinger finger cot body.

While the forefinger finger cot palmar portion is formed of a high grip tackified leather material, the dorsal portion of the forefinger finger cot body is constructed of high stretch material 555 such as nylon. The high stretch material provides a stretch capability to expand at least a factor two from its original length when stretched. Because the forefinger finger cot body palmar portion is formed of a tackified leather material, the palm side of the finger cot will create high grip capabilities with a tacky and durable surface. For this reason it is important that the forefinger finger cot body dorsal portion be high flexible and stretchable to allow the necessary degree of movement or flexing of the digital segment. This particular finger cot construction would also therefore not require an aperture on the body dorsal portion as the stretchiness of the dorsal portion allows the user to easily bend and flex the digital segment during active sports play when the finger cot is worn. As such, a material incapable of expanding and subsequently contracting at least one centimeter and back to its original position would not work as a dorsal portion material of the forefinger finger cot embodiment.

The finger cot embodiment also has an expandable securement opening means at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit 511 or opening along the embodiment's dorsal portion to allow the finger cot to enclose a digital segment of a user, such as on a user's forefinger, for example. In addition, the opening securement means comprises an elastomeric band 513 fixed around the open ends of the embodiments. The expandable securement opening means may be formed integral with the finger cot or may be attached to the finger cot by standard methods, such as by sewing. The strap can generally be constructed of the same material forming the finger cot.

A second finger cot embodiment is shown and designated as 530. The palmar view 531 of the finger cot is drawn in FIG. 21, and the dorsal view 532 of the same finger cot is drawn in FIG. 22. This finger cot has a body adapted to fit snugly around a pinkie finger of a human hand, said body is of substantial size to overlay at least one phalanx of the digital segment without overlying another digital segment of the user's hand. The pinkie finger finger cot body has a palmar portion 533 and a dorsal portion 534. The pinkie finger finger cot body also has a distal end, said distal end is closed to enclose the user's digital segment. The pinkie finger finger cot body also has a proximal end which has an opening adapted to receive the digital segment of the user. The pinkie finger finger cot body longitudinally extends from said distal end to said proximal end.

The pinkie finger finger cot body also has a distal portion 535 which is of substantial size and positioned to overlay essentially the entire distal phalanx of the user's digital segment. The pinkie finger finger cot body distal portion includes a distal end. The distal portion includes a dorsal portion that covers the back of the digital segment, and a palmar portion that covers the front (palmar) of the digital segment.

The pinkie finger finger cot body also has a middle portion 536 which is of substantial size and positioned to overlay essentially the entire middle phalanx of the user's digital segment. The middle portion includes a dorsal portion that covers the back of the digital segment, and a palmar portion that covers the front (palmar) of the digital segment.

The pinkie finger finger cot body also has a proximal portion 537 which is of substantial size and positioned to overlay a proximal phalanx of the user's digital segment. The proximal portion section includes a dorsal portion that covers the back of the digital segment, and a palmar portion that covers the front (palmar) of the digital segment.

The pinkie finger finger cot body middle portion longitudinally extends between the pinkie finger finger cot body distal portion and the forefinger finger cot body proximal portion.

The pinkie finger finger cot body proximal portion includes the proximal end which is open to receive the user's digital segment, and also includes an expandable securement opening means 538 comprising of a strap 539 and hook and loop fasteners 540 so that the user can manually engage and disengage the finger cot. The proximal end also includes a slit along the dorsal side whereby the strap can extend over the slit 541.

The entire pinkie finger finger cot palmar portion is essentially entirely formed of a high grip tackified leather material 550 and can be created and secured to the pinkie finger finger cot by any standard mechanism, such as stitching to the finger cot dorsal portion. The high grip tackified leather material enhances a user's ability of controlling a ball or an object by providing a higher coefficient of friction than what the skin of a user might otherwise provide, preferably a Coefficient of Friction of at least 2.0. More preferably, a Coefficient of Friction of at least 2.5. In other words, the entire palmar portion of the pinkie finger finger cot body distal portion is formed of a high grip tackified leather material, the entire palmar portion of the pinkie finger finger cot body middle portion is formed of a high grip tackified leather material, and the entire palmar portion of the pinkie finger finger cot body proximal portion is formed of a high grip tackified leather material. Preferably, the pinkie finger finger cot body palmar portion is one uniform high grip tackified leather that is therefore of substantial size to overlay the user's entire distal phalanx, entire middle phalanx and entire proximal phalanx. The high grip tackified leather material could then be affixed to the pinkie finger finger cot dorsal portion to form the pinkie finger finger cot body.

While the pinkie finger finger cot palmar portion is formed of a high grip tackified leather material, the dorsal portion of the pinkie finger finger cot body is constructed of high stretch material 555 such as nylon. The high stretch material provides a stretch capability to expand at least a factor two from its original length when stretched. Because the pinkie finger finger cot body palmar portion is formed of a tackified leather material, the palm side of the finger cot will create high grip capabilities with a tacky and durable surface. For this reason it is important that the pinkie finger finger cot body dorsal portion be high flexible and stretchable to allow the necessary degree of movement or flexing of the digital segment. This particular finger cot construction would also therefore not require an aperture on the body dorsal portion as the stretchiness of the dorsal portion allows the user to easily bend and flex the digital segment during active sports play when the finger cot is worn. As such, a material incapable of expanding and subsequently contracting at least one centimeter and back to its original position would not work as a dorsal portion material of the pinkie finger finger cot embodiment.

The finger cot embodiment also has an expandable securement opening means at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit 541 or opening along the embodiment's dorsal portion to allow the finger cot to enclose a digital segment of a user, such as on a user's forefinger, for example. In addition, the opening securement means comprises an elastomeric band 543 fixed around the open ends of the embodiments. The expandable securement opening means may be formed integral with the finger cot or may be attached to the finger cot by standard methods, such as by sewing. The strap can generally be constructed of the same material forming the finger cot.

These finger cot embodiments, individually or in combination, offer the ability in one respect, to essentially separate a conventional glove into its different components and then selectively choose which components to wear. This can be especially important for those individuals who need to retain heightened sensitivities in part of the hand, but need grip support in another part of the same hand. Using gloves instead of finger embodiments for these individuals would also be an unnecessary waste of materials.

The high grip tackified leather material can be created by coating or impregnating tackifiers including tackifier resins, such as rosins and their derivatives, terpenes, aliphatic, cycloaliphatic and aromatic resin, and any of a variety of hydrocarbon-type resins, tackifier coatings, tackified materials onto a leather or synthetic leather material. Creating a high grip tackified leather material can be created, for example, by impregnating a leather 551 with a tackifier resin and then affixing said material onto the dorsal portion of the finger cot body. This particular configuration provides for maximum grip capabilities for a user, such as a golfer. Alternatively, a high grip tackified leather material may be created by spraying a tackifier coating, such as POWR TAC SPRAY-ON TACKIFIER onto a genuine leather material and subsequently securing the newly formed tackified leather material onto the finger cot body to form the entire finger cot body palmar portion. As aforementioned, it is important that the finger cot body dorsal portion of the embodiments discussed in FIG. 21 and FIG. 22 is formed of a more elastic material than the leather forming the palmar portion. As such, a suitable material forming the finger cot body dorsal portion is a polyester and elastic combination such as NYLON for added flexibility and maneuverability. The finger cot body palmar and dorsal portions are essentially the same size in length and width.

Referring now to FIG. 23, FIG. 24, FIG. 25, and FIG. 26, the present invention is shown as various grip-enhancing finger cot embodiments that are free of stitches on the side of the finger cot to minimize abrasion of an opposing finger when gripping a golf club. As aforementioned, the finger cot tubular member embodiments of the present invention all have a body adapted to fit around a digital segment of a human hand, and are adapted to overlay at least one phalanx of a user's finger without overlying another finger of the user's hand. The finger cot embodiments shown on FIG. 23, FIG. 24, FIG. 25 and FIG. 26 all have a palmar portion that cover the palm side of the finger, a dorsal portion that covers the back of the user's finger, a first side and a second opposite the first side. More specifically, the finger cot embodiments 700, 770 all have a closed first end comprising a distal portion material that overlays the distal phalanx, a middle portion material that overlays the middle phalanx, and a second end comprising a proximal portion material that overlays the proximal phalanx of the user's finger when the embodiment is worn. The distal portion includes the finger cot distal end, and the proximal portion includes the finger cot proximal end.

These finger cot embodiments are all formed principally of a leather or synthetic leather 750 to maximize durability, particularly when playing the sport of golf.

Shown on a user's left hand are two separate finger cot embodiments 700 and 770. Each embodiment could be used independently or in combinations. These embodiments have a circumference large enough to be able to fit tightly around select areas of a digital segment, but do not extend to overlay a second digital segment.

One finger cot embodiment is shown and designated as 700. The palmar view 701 of the finger cot is drawn in FIG. 23, and the dorsal view 702 of the same finger cot is drawn in FIG. 24. This finger cot has a body adapted to fit snugly around a forefinger of a human hand, said body is of substantial size to overlay at least one phalanx of the digital segment without overlying another digital segment of the wearer's hand. The forefinger finger cot body has a palmar portion 703 and a dorsal portion 704. The forefinger finger cot body also has a distal end, said distal end is closed to enclose the user's digital segment. The forefinger finger cot body also has a proximal end which has an opening adapted to receive the digital segment of the user. The forefinger finger cot body longitudinally extends from said distal end to said proximal end.

The forefinger finger cot body also has a distal portion 705 which is of substantial size and positioned to overlay essentially the entire distal phalanx of the wearer's digital segment but does not extend to overlay beyond the distal phalanx. The forefinger finger cot body distal portion includes a distal end that is closed to enclose the digital segment when the finger cot is worn.

The forefinger finger cot body also has a middle portion 706 which is of substantial size and positioned to overlay essentially the entire middle phalanx of the wearer's digital segment.

The forefinger finger cot body also has a proximal portion 707 which is of substantial size and positioned to overlay a proximal phalanx of the wearer's digital segment and includes the proximal end that is open to receive the user's digital segment, and also includes an expandable securement opening means 708 comprising of a strap 709 and hook and loop fasteners 710 so that the user can manually engage and disengage the finger cot. The proximal end also includes a slit along the dorsal side whereby the strap can extend over the slit 711.

The forefinger finger cot body middle portion longitudinally extends between the forefinger finger cot body distal portion and the forefinger finger cot body proximal portion.

The forefinger finger cot body palmar portion is formed of a leather or synthetic leather material 750. In addition, the forefinger finger cot body dorsal portion is formed of a leather or synthetic leather material 751.

The finger cot embodiment also has an expandable securement opening means at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit 711 or opening along the embodiment's dorsal portion to allow the finger cot to enclose a digital segment of a user, such as on a user's forefinger, for example. In addition, the opening securement means comprises an elastomeric band 713 fixed around the open ends of the embodiments. The expandable securement opening means may be formed integral with the finger cot or may be attached to the finger cot by standard methods, such as by sewing. The strap can generally be constructed of the same material forming the finger cot.

A moisture absorbent material 714 is provided along the dorsal portion of the finger cot, allowing a user to wipe off perspiration commonly on a user's face during active sports play. The moisture absorbent material may be secured anywhere along the dorsal surface 715 or on the securement opening means, such as affixed to the top surface of a strap, and does not extend to the finger cot palmar portion. The moisture absorbent material may be formed of any moisture absorbent material aforementioned, such as, for example, about 1⁄12 inch terry cloth 714 stitched onto the finger cot body dorsal portion.

Additionally, embodiments such as this may be coated with a water repellant substance 716, such as a synthetic resin, for example, especially useful during rainy weather game situations. The water repellant is applied to the entire embodiment.

Shown also is an aperture 717 which leaves exposed a user's interphalangeal joint. The aperture allows a user to more easily flex and maneuver his or her finger during active sports play, particularly when bending and flexing the digital segment during game play. The edge of the aperture is stitched 718 to prevent fraying along the aperture.

Shown also are microrecesses 720 along the finger cot dorsal portion proximal portion, middle portion, and distal portion, for enhanced moisture management capabilities. These microrecesses are generally about 0.120 millimeters in diameter.

A second finger cot embodiment is shown and designated as 770. The palmar view 771 of the finger cot is drawn in FIG. 23, and the dorsal view 772 of the same finger cot is drawn in FIG. 24. This finger cot has a body adapted to fit snugly around a pinkie finger of a human hand, said body is of substantial size to overlay at least one phalanx of the digital segment without overlying another digital segment of the user's hand. The pinkie finger finger cot body has a palmar portion 773 and a dorsal portion 774. The pinkie finger finger cot body also has a distal end, said distal end is closed to enclose the user's digital segment. The pinkie finger finger cot body also has a proximal end which has an opening adapted to receive the digital segment of the user. The pinkie finger finger cot body longitudinally extends from said distal end to said proximal end.

The pinkie finger finger cot body also has a distal portion 775 which is of substantial size and positioned to overlay essentially the entire distal phalanx of the wearer's digital segment but does not extend to overlay beyond the distal phalanx. The pinkie finger finger cot body distal portion includes a distal end that is closed to enclose the digital segment when the finger cot is worn.

The pinkie finger finger cot body also has a middle portion 776 which is of substantial size and positioned to overlay essentially the entire middle phalanx of the wearer's digital segment.

The pinkie finger finger cot body also has a proximal portion 777 which is of substantial size and positioned to overlay a proximal phalanx of the wearer's digital segment and includes the proximal end that is open to receive the user's digital segment, and also includes an expandable securement opening means 778 comprising of a strap 779 and hook and loop fasteners 780 so that the user can manually engage and disengage the finger cot. The proximal end also includes a slit along the dorsal side whereby the strap can extend over the slit 781.

The pinkie finger finger cot body middle portion longitudinally extends between the pinkie finger finger cot body distal portion and the pinkie finger finger cot body proximal portion.

The pinkie finger finger cot body palmar portion is formed of a leather or synthetic leather material 750. In addition, the pinkie finger finger cot body dorsal portion is formed of a leather or synthetic leather material 751.

The finger cot embodiment also has an expandable securement opening means at an open end adapted to receive the user's hand. The securement opening means includes a strap which mechanically engages a strap capture mechanism to secure the finger cot such as a synthetic hook and loop fastening interface which adheres when pressed together, commonly using VELCRO. The strap is positioned to overlay a small slit or opening along the embodiment's dorsal portion to allow the finger cot to enclose a digital segment of a user, such as on a user's forefinger, for example. In addition, the opening securement means comprises an elastomeric band 783 fixed around the open ends of the embodiments. The expandable securement opening means may be formed integral with the finger cot or may be attached to the finger cot by standard methods, such as by sewing. The strap can generally be constructed of the same material forming the finger cot.

A moisture absorbent material 785 is provided along the dorsal portion of the finger cot, allowing a user to wipe off perspiration commonly on a user's face during active sports play. The moisture absorbent material may be secured anywhere along the dorsal surface or on the securement opening means, such as affixed to the finger cot body dorsal portion, and does not extend to the finger cot palmar portion. The moisture absorbent material may be formed of any moisture absorbent material aforementioned, such as, for example, about 1⁄12 inch terry cloth 785 stitched onto the substantially the top surface.

Additionally, embodiments such as this may be coated with a water repellant substance 787, such as a synthetic resin, for example, especially useful during rainy weather game situations. The water repellant may be applied to the entire embodiment.

Shown also is an aperture 790 which leaves exposed a user's interphalangeal joint. The aperture allows a user to more easily flex and maneuver his or her finger during active sports play, particularly when bending and flexing the digital segment during game play. The edge of the aperture is stitched 791 to prevent fraying along the aperture.

Shown also are microrecesses 792 along the finger cot dorsal portion proximal portion, middle portion, and distal portion, for enhanced moisture management capabilities. These microrecesses are generally about 0.120 millimeters or so in diameter.

These finger cot embodiments, individually or in combination, offer the ability in one respect, to essentially separate a conventional glove into its different components and then selectively choose which components to wear. This can be especially important for those individuals who need to retain heightened sensitivities in part of the hand, but need grip support in another part of the same hand. Using gloves instead of finger embodiments for these individuals would also be an unnecessary waste of materials.

Figure 23:
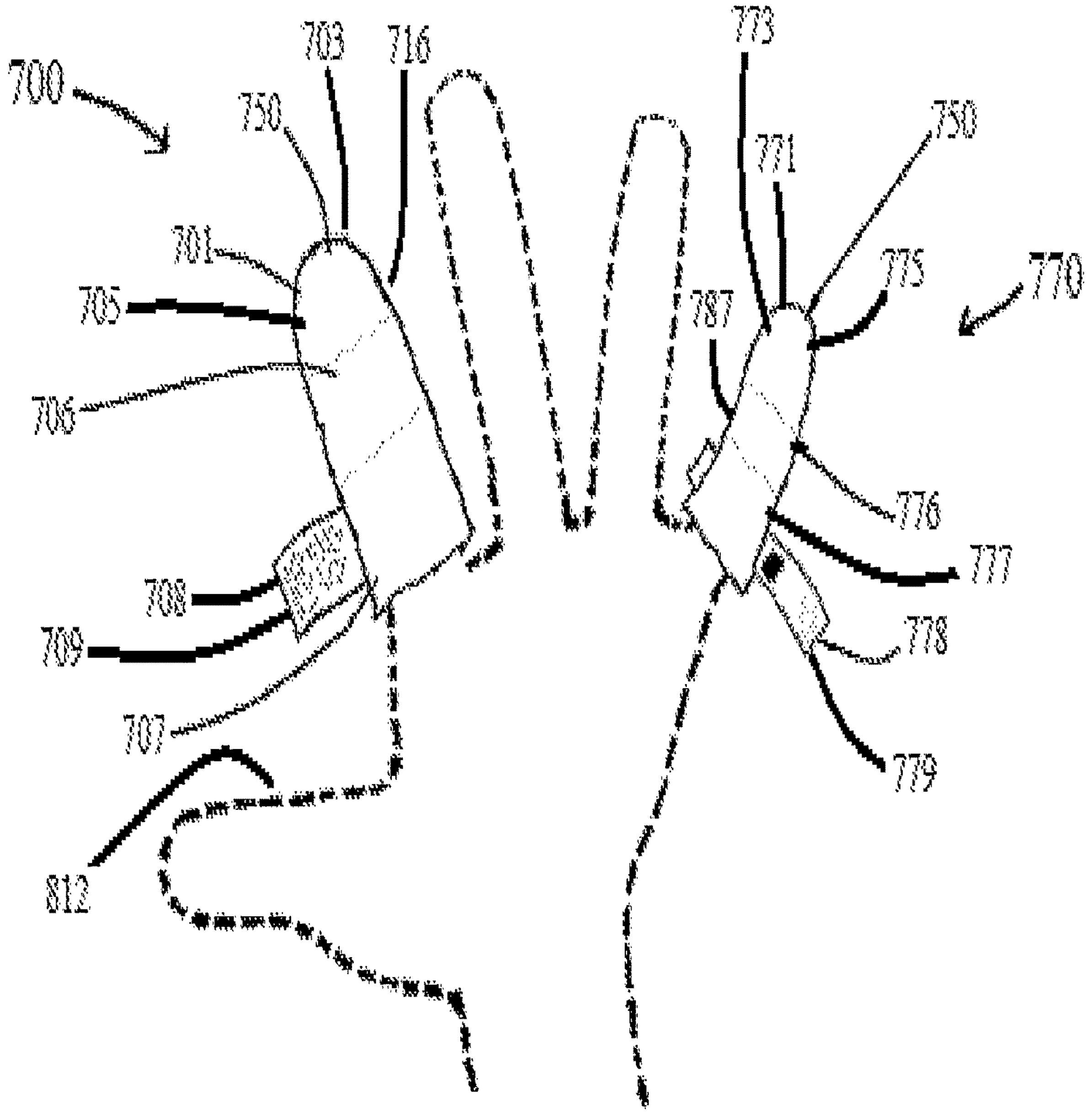
FIG. 23 is a drawing of several finger cot embodiments on the left hand of a user, showing the palmar surfaces.
Figure 24:
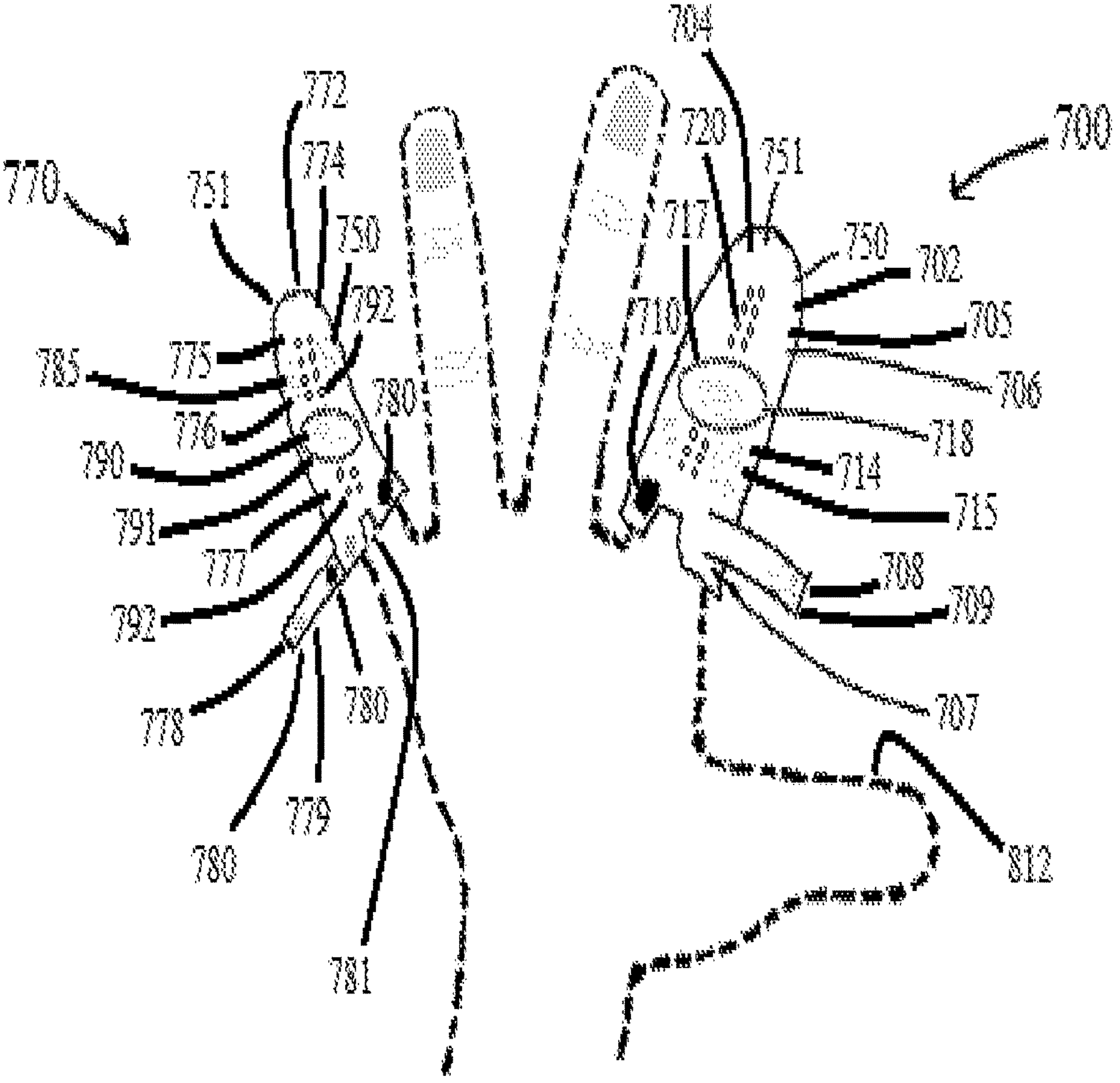
FIG. 24 is a drawing showing the dorsal surfaces of the embodiments in FIG. 23.
Figure 25:
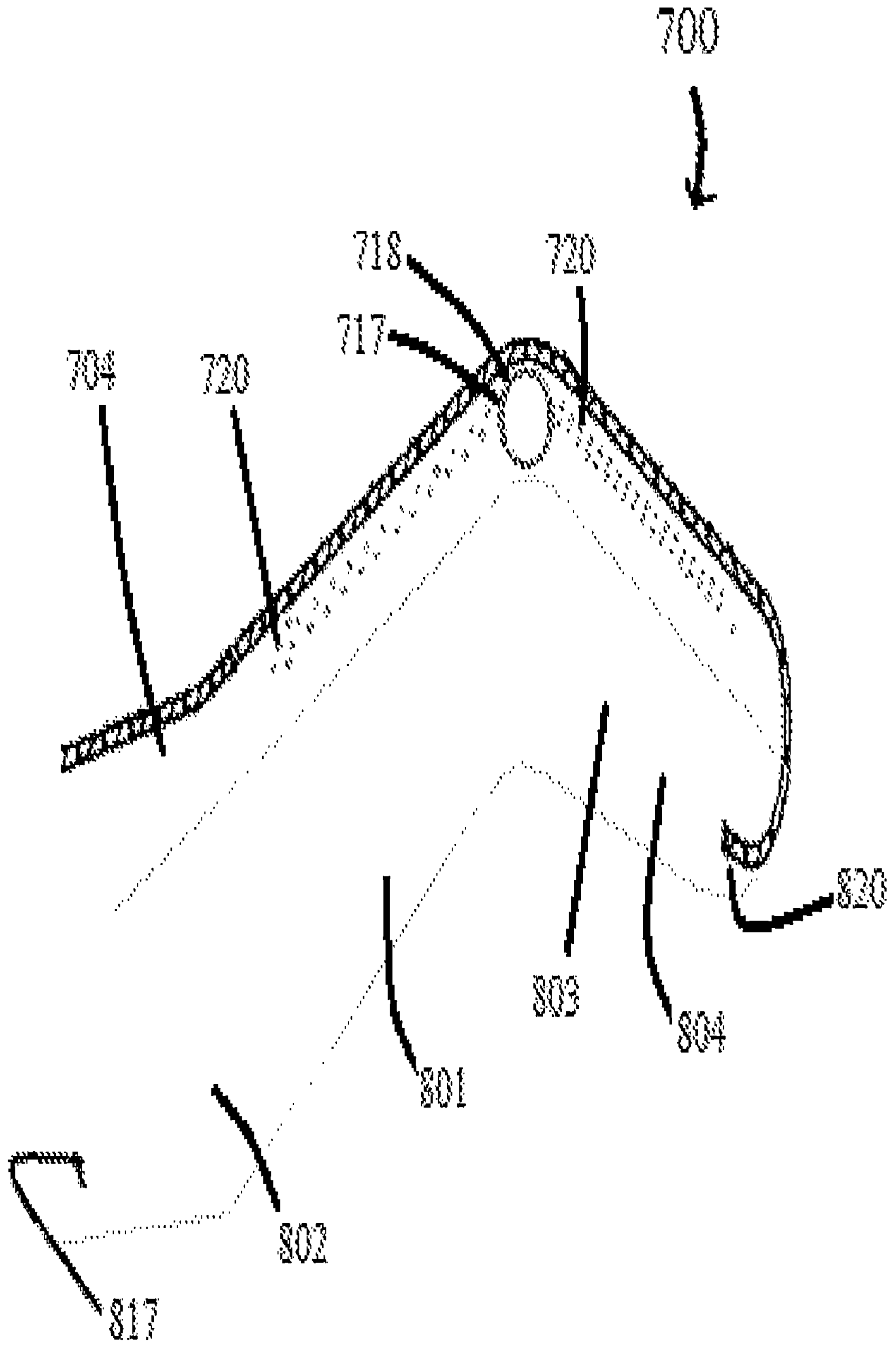
FIG. 25 and FIG. 26 are drawings showing both sides of the finger cot embodiments in FIG. 23.
Figure 26:
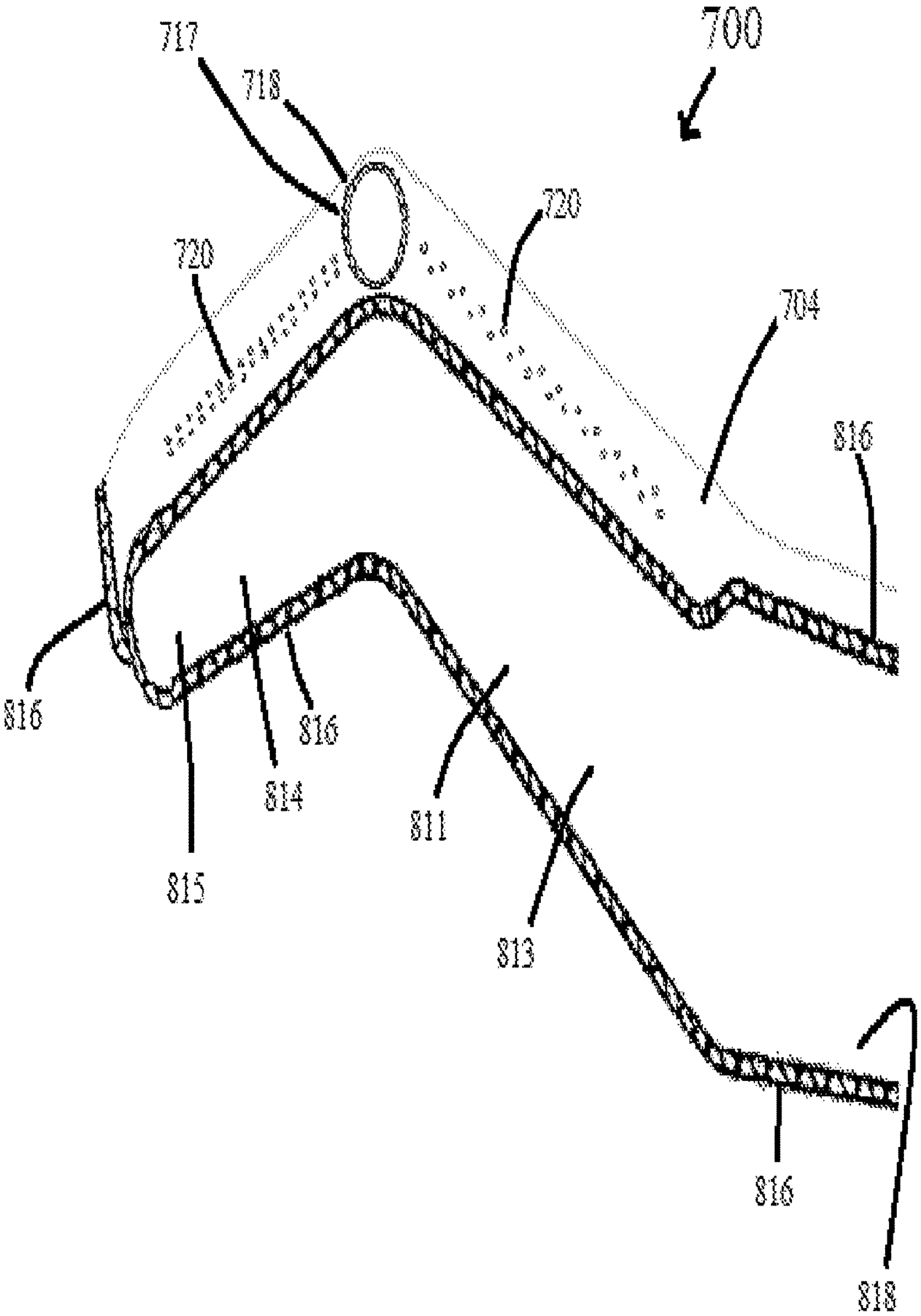

FIG. 25 and FIG. 26 show two opposing sides of a finger cot embodiment, as shown in FIG. 23 and FIG. 24, over a user's forefinger 700. The first side 801 in this embodiment is adjacent to a user's middle finger. The first side has a proximal portion 802 that overlays the user's proximal phalanx, a middle portion 803 that overlays the user's middle phalanx, and a distal portion 804 that overlays the distal phalanx when the finger cot is worn. The first side proximal portion is entirely free of stitches, and the first side middle portion is also entirely free of stiches. Constructing the finger cot embodiment in this unique way will provide exceptional benefits to users particular when using the finger cot embodiment on the user's ungloved strong hand when playing the sport of golf.

For example, as aforementioned, the standard way of swinging a golf club is by using a glove on the weak hand while keeping the strong hand ungloved to maximize tactile sensations during the golf swing. Using the finger cot embodiment on only the strong hand's forefinger will substantially increase grip now on the strong hand while leaving the rest of the strong hand ungloved to maintain necessary tactile sensitivities throughout the rest of the hand, especially along the palm. However, as the user increases use of the forefinger finger cot embodiment the constant rubbing between the forefinger finger cot first side with the skin of the adjacent middle finger can begin to swell, redden and degrade, even injury. The leather material is well known to be smooth which would not cause abrasion but if stitches are located on the first side, the stitches project out and inevitably make first and constant contact with the adjacent middle finger when gripping a golf club. As such, by uniquely designing the finger cot such that no stitches reside on the proximal portion first side and on the middle portion first side, the finger cot can increase the user's grip without causing unnecessary damage or injury to the user's hand. In addition, most of the distal portion first side is also free of any stitches. The distal portion may comprise of stitches but no more than half of the first side distal portion may comprise of any stitches, and certainly no stitches extend onto the first side middle portion or the first side proximal portion without interfering with the intended function of this embodiment.

The second side 811 is adjacent the user's thumb 812. The second side has a proximal portion 813 that overlays the user's proximal phalanx, a middle portion 814 that overlays the user's middle phalanx, and a distal portion 815 that overlays the distal phalanx when the finger cot is worn. The second side has stitches 816 along the edges of the proximal portion second side, the middle portion second side, and the distal portion second side. Stitches are also located along the finger cot distal end to enclose the digital segment.

Also shown is a liner 817. The lining material may be comprised of standard lining materials, such as a smooth, flexible knitted fabric. The liner may also comprise of flexible and elastomeric material such as spandex or LYCRA. Other possible materials include a knit of polyester or simply the same material forming the tubular member. A soft cellular plastic could also be preferred. Additionally, the liner may provide added features to offer warmth and comfort such as by comprising of a fleece material 818, for example, especially useful when competing in rather harsh environments.

I claim:

1. A finger cot comprising: a body adapted to fit around a digital segment of a human hand, wherein said body is adapted to overlay at least one phalanx of the digital segment without overlying another digital segment of the human hand, wherein the body comprises: a palmar portion; a dorsal portion; a distal end, wherein said distal end is closed; a proximal end comprising an opening adapted to receive said digital segment, wherein said body longitudinally extends from said distal end to said proximal end;

- a distal portion adapted to overlay a distal phalanx of the digital segment, wherein the distal portion comprises:
  - the distal end;
  - a first grip enhancing panel formed of a high grip tackified leather material disposed on the palmar portion of the distal portion; and,
  - microrecesses disposed on the dorsal portion of the distal portion;
- wherein said body comprises a middle portion adapted to overlay a middle phalanx of the digital segment, and wherein the middle portion comprises:
  - a second grip enhancing panel formed of a high grip tackified leather material disposed on the palmar portion of the middle portion;
- wherein said body comprises a proximal portion adapted to overlay a proximal phalanx of the digital segment,
- wherein the middle portion longitudinally extends between the distal portion and the proximal portion, and wherein the proximal portion comprises:
  - the proximal end; and
  - a third grip enhancing panel formed of a high grip tackified material disposed on the palmar portion of the proximal portion.

2. The finger cot as claimed in claim 1, wherein an exterior surface comprises a moisture repellant substance comprising a synthetic resin.

3. The finger cot as claimed in claim 1, wherein said first, second, or third grip enhancing panel residing along the finger cot palmar portion is adapted to provide a coefficient of friction of at least 2 when the finger cot is worn.

4. The finger cot, as claimed in claim 1, wherein said body comprises polyester and is elastic.

5. The finger cot as claimed in claim 1 wherein said proximal end of said finger cot body further comprises an expandable securement opening means comprising of a strap that is adapted to allow the user to apply and disengage the finger cot.

6. The finger cot as claimed in claim 1 further comprising a slit originating at said proximal end and adapted to allow the finger cot to widen when the user places the finger cot on to the user's digital segment;

- wherein said finger cot distal end further comprises a strap and a hook and loop fastening interface;

wherein said hook and loop fastening interface is adapted to engage said strap to secure the finger cot on a digital segment of the user's hand when the finger cot is worn;

wherein said strap is positioned such that it can extend across said slit and is adapted to allow the finger cot to enclose said user's digital segment.

7. The finger cot as claimed in claim 1, wherein the finger cot dorsal portion comprises an aperture positioned on the middle portion and proximal portion;

wherein said aperture is adapted to be of substantial size and is further positioned to expose an interphalangeal joint of the wearer's finger when the finger cot is worn.

8. The finger cot as claimed in claim 1, wherein said first grip enhancing panel does not extend onto the finger cot body middle portion;

wherein said second grip enhancing panel does not extend onto the finger cot body distal portion;

wherein said third grip enhancing panel does not extend onto the finger cot body middle portion.

9. A finger cot comprising: a body adapted to fit around a digital segment of a human hand, wherein said body is adapted to overlay at least one phalanx of the digital segment without overlying another digital segment of the human hand, wherein the body comprises:

a palmar portion;

a dorsal portion;

and a distal end;

wherein said distal end is closed;

wherein said body comprises a proximal end comprising an opening adapted to receive said digital segment, wherein said body longitudinally extends from said distal end to said proximal end;

wherein said body comprises a distal portion adapted to overlay a distal phalanx of the digital segment, wherein the distal portion comprises:

the distal end;

a first grip enhancing panel formed of a high grip tackified leather material disposed on the palmar portion of the distal portion;

wherein said body comprises a middle portion that is adapted to overlay a middle phalanx of the digital segment, and wherein the middle portion comprises:

a second grip enhancing panel formed of a high grip tackified leather material disposed on the palmar portion of the middle portion and is adapted to overlay a middle phalanx of the user's digital segment but does not extend beyond the middle phalanx when the finger cot is worn;

wherein said body comprises a proximal portion that is adapted to overlay a proximal phalanx of the digital segment;

wherein the middle portion longitudinally extends between the distal portion and the proximal portion, and wherein the proximal portion comprises:

the proximal end; and a third grip enhancing panel formed of a high grip tackified leather material disposed on the palmar portion of the proximal portion and is adapted to overlay the proximal phalanx of the user's digital segment but does not extend beyond the proximal phalanx area when the finger cot is worn;

and wherein said proximal end of said finger cot body further comprises an expandable securement opening means comprising a strap.

10. The finger cot as claimed in claim 9, wherein an exterior surface of said body comprises a moisture repellent substance.

11. The finger cot as claimed in claim 9, wherein said a strap is affixed to said dorsal portion at the finger cot distal end; and, wherein said finger cot further comprises a strap capture mechanism; and, wherein said strap is adapted to mechanically engage said strap capture mechanism, thereby allowing the user to secure the finger cot to the user's finger when the finger cot is worn.

12. The finger cot as claimed in claim 9, further comprising: a slit originating at said proximal end and is adapted to allow the finger cot to widen when the user places the finger cot on to the user's digital segment;

wherein said finger cot distal end further comprising a hook and loop fastening interface;

wherein said hook and loop fastening interface is adapted to engage said strap to secure the finger cot on a digital segment of the user's hand when the finger cot is worn;

wherein said strap is positioned such that it can extend across said slit and is adapted to allow the finger cot to enclose said user's digital segment.

13. The finger cot as claimed in claim 9, wherein the finger cot dorsal portion comprises an aperture positioned on the middle portion and proximal portion;

wherein said aperture is adapted to be of substantial size and is further positioned to expose an interphalangeal joint of the wearer's finger when the finger cot is worn.

14. The finger cot as claimed in claim 9, wherein said first grip enhancing panel does not extend onto the finger cot body middle portion;

wherein said second grip enhancing panel does not extend onto the finger cot body distal portion;

wherein said third grip enhancing panel does not extend onto the finger cot body middle portion.

15. A sports finger cot comprising: a body adapted to fit around a digital segment of a human hand, wherein said body is adapted to overlay at least one phalanx of the digital segment without overlying another digital segment of the human hand, wherein the body comprises:

a palmar portion;

a dorsal portion;

a distal end;

wherein said distal end is closed;

wherein said body comprises a proximal end comprising an opening adapted to receive said digital segment, wherein said body longitudinally extends from said distal end to said proximal end;

wherein said body comprises a distal portion adapted to overlay a distal phalanx of the digital segment, wherein the distal portion comprises:

the distal end;

a first grip enhancing panel formed of a high grip tackified leather material disposed on the palmar portion of the distal portion;

wherein said body comprises a middle portion adapted to overlay a middle phalanx of the digital segment, and wherein the middle portion comprises:

a second grip enhancing panel formed of a high grip tackified leather material disposed on the palmar portion of the middle portion and is adapted to overlay a middle phalanx of the user's digital segment but does not extend beyond the middle phalanx when the finger cot is worn; and, wherein said body comprises a proximal portion adapted to overlay a proximal phalanx of the digital segment, wherein the middle portion longitudinally extends between the distal portion and the proximal portion, and wherein the proximal portion comprises:

the proximal end;

and a third grip enhancing panel formed of a high grip tackified leather material disposed on the palmar portion of the proximal portion and is adapted to overlay the proximal phalanx of the user's digital segment but does not extend beyond the proximal phalanx area when the finger cot is worn; and, wherein said proximal end of said sports finger cot body further comprises an expandable securement opening means comprising of a strap.

16. The sports finger cot as claimed in claim 15, wherein said sports finger cot body comprises microrecesses disposed on the dorsal portion of the distal portion.

17. The sports finger cot as claimed in claim 15, wherein said sports finger cot body comprises microrecesses disposed on the dorsal portion of the middle portion.

18. The sports finger cot as claimed in claim 15, further comprising:

a slit originating at said proximal end and is adapted to allow the sports finger cot to widen when the user places the sports finger cot on to the user's digital segment;

wherein said sports finger cot distal end further comprising a hook and loop fastening interface;

wherein said hook and loop fastening interface is adapted to engage said strap to secure the sports finger cot on a digital segment of the user's hand when the sports finger cot is worn;

wherein said strap is positioned such that it can extend across said slit and is adapted to allow the sports finger cot to enclose said user's digital segment.

19. The sports finger cot as claimed in claim 15, wherein the sports finger cot dorsal portion comprises an aperture positioned on the middle portion and proximal portion;

said aperture is adapted to be of substantial size and is further positioned to expose an interphalangeal joint of the wearer's finger when the sports finger cots is worn.

20. The sports finger cot as claimed in claim 15, wherein said first grip enhancing panel does not extend onto the sports finger cot body middle portion;

wherein said second grip enhancing panel does not extend onto the sports finger cot body distal portion;

wherein said third grip enhancing panel does not extend onto the sports finger cot body middle portion.

* * * * *